(12) United States Patent
Wilson et al.

(10) Patent No.: US 12,285,170 B2
(45) Date of Patent: Apr. 29, 2025

(54) SURGICAL STAPLER CARTRIDGE HAVING CARTRIDGE RETENTION FEATURES

(71) Applicant: Cilag GmbH International, Zug (CH)

(72) Inventors: Nicholas A. Wilson, Montgomery, OH (US); Kevin M. Fiebig, Cincinnati, OH (US); Nicholas Fanelli, Morrow, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/588,240

(22) Filed: Feb. 27, 2024

(65) Prior Publication Data

US 2024/0382203 A1 Nov. 21, 2024

Related U.S. Application Data

(60) Provisional application No. 63/467,649, filed on May 19, 2023.

(51) Int. Cl.
*A61B 17/072* (2006.01)
*A61B 17/00* (2006.01)

(52) U.S. Cl.
CPC ............ *A61B 17/07207* (2013.01); *A61B 2017/00473* (2013.01); *A61B 2017/07264* (2013.01); *A61B 2017/07271* (2013.01); *A61B 2017/07278* (2013.01); *A61B 2017/07285* (2013.01)

(58) Field of Classification Search
CPC .......... A61B 17/07207; A61B 17/0725; A61B 2017/07257; A61B 17/068; A61B 17/072
See application file for complete search history.

(56) References Cited

U.S. PATENT DOCUMENTS

| | | | |
|---|---|---|---|
| 5,673,840 A | 10/1997 | Schulze et al. |
| 8,453,914 B2 | 6/2013 | Laurent et al. |
| 9,186,142 B2 | 11/2015 | Fanelli et al. |
| 9,717,497 B2 | 8/2017 | Zerkle et al. |
| 9,839,421 B2 | 12/2017 | Zerkle et al. |
| 10,092,292 B2 | 10/2018 | Boudreaux et al. |
| 10,130,359 B2 | 11/2018 | Hess et al. |

(Continued)

FOREIGN PATENT DOCUMENTS

WO 2022/118168 A2 6/2022

OTHER PUBLICATIONS

U.S. Appl. No. 18/588,094.

(Continued)

*Primary Examiner* — Michelle Lopez
(74) *Attorney, Agent, or Firm* — Frost Brown Todd LLP

(57) ABSTRACT

A staple cartridge for a surgical instrument includes a cartridge body extending along a longitudinal axis and having an upper deck. Pockets extend through the upper deck for receiving respective staples. The staple cartridge also includes a pan coupled to the cartridge body. The pan includes a laterally-opposed pair of sidewalls spaced apart from each other to define a trough sized and configured to receive the cartridge body. The pan also includes a retention tab extending laterally outwardly from a sidewall and longitudinally between proximal and distal ends. The retention tab defines a recess extending laterally outwardly from the trough. The recess opens through the sidewall at at least one of the proximal or distal ends. The pan further includes a relief slot extending through the sidewall adjacent to the at least one of the proximal or distal ends such that the relief slot opens directly into the recess.

20 Claims, 20 Drawing Sheets

(56) References Cited

U.S. PATENT DOCUMENTS

| | | | |
|---|---|---|---|
| 11,051,811 | B2 | 7/2021 | Shelton, IV et al. |
| 11,478,244 | B2 | 10/2022 | DiNardo et al. |
| 11,896,218 | B2 | 2/2024 | Bakos et al. |
| 2021/0219976 | A1 | 7/2021 | DiNardo et al. |
| 2022/0133306 | A1 | 5/2022 | Nalagatla et al. |

OTHER PUBLICATIONS

U.S. Appl. No. 18/588,147.
U.S. Appl. No. 18/588,175.
U.S. Appl. No. 18/588,206.
U.S. Appl. No. 18/588,269.
U.S. Appl. No. 18/588,684.
Partial International Search Report and Written Opinion dated Aug. 22, 2024, for International Application No. PCT/IB2024/054892, 17 pages.
U.S. Appl. No. 18/588,094, entitled "Incompatible Staple Cartridge Use Prevention Features for Surgical Stapler," filed Feb. 27, 2024.
U.S. Appl. No. 18/588,147, entitled "Surgical Stapler Cartridge Having Intermediate Raised Tissue Engagement Protrusions," filed Feb. 27, 2024.
U.S. Appl. No. 18/588,175, entitled "Surgical Stapler Cartridge Having Tissue Engagement Protrusions with Enlarged Engagement Surface," filed Feb. 27, 2024.
U.S. Appl. No. 18/588,206, entitled "Surgical Stapler Cartridge Having Raised Surface to Promote Buttress Adhesion," filed Feb. 27, 2024.
U.S. Appl. No. 18/588,269, entitled "Surgical Stapler Anvil Having Staple Forming Pockets with Laterally Varying Orientations," filed Feb. 27, 2024.
U.S. Appl. No. 18/588,684, entitled "Method of Surgical Stapling," filed Feb. 27, 2024.
International Search Report and Written Opinion dated Oct. 14, 2024, for International Application No. PCT/IB2024/054892, 22 pages.

SURGICAL STAPLER CARTRIDGE HAVING CARTRIDGE RETENTION FEATURES

PRIORITY

This application claims the benefit of U.S. Pat. App. No. 63/467,649, entitled "Surgical Stapler Cartridge Having Cartridge Retention Features," filed May 19, 2023, the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion or other type of body portion, which is manipulated by the clinician or robotic operator. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

The staple cartridge of a surgical stapler may include a lower pan (also referred to as a "tray") coupled to an underside of a cartridge body of the staple cartridge, and may further include a sled (also referred to as a "wedge sled") that is actuated longitudinally within the staple cartridge from a proximal unfired position to a distal fired position for actuating deployment of the staples. The pan may include one or more (e.g., two) distal retention tabs (also referred to as "protrusions" or "bumps") for frictionally engaging a channel of a cartridge jaw of the surgical stapler to removably secure the staple cartridge within the channel, with such frictional engagement being sufficient to resist dislodgment of the staple cartridge from the channel in the absence of a threshold amount of force applied between the staple cartridge and the channel, at least when the sled is proximal of the distal fired position, such as when the sled is in the proximal unfired position (also referred to as the "cartridge retention force").

When the sled is in the distal fired position, the sled may be at a substantially same position in the longitudinal direction as the distal retention tabs, such that the presence of the sled in the distal fired position may increase the threshold amount of force required to remove the staple cartridge from the channel when the sled is in the distal fired position (also referred to as the "cartridge removal force"). For example, the sled may have a sufficient stiffness to resist laterally inward flexing of the staple cartridge when the sled is in the distal fired position, thereby resisting disengagement of the distal retention tabs from the channel, such as in cases where the sled comprises a metal material. In some instances, the increased cartridge removal force may be significantly greater than the desired cartridge retention force, which may render removal of the staple cartridge difficult after firing. The surgical staplers of the present disclosure seek to provide a desired cartridge retention force (i.e., the threshold force required to remove the cartridge prior to and/or during firing) while reducing or eliminating such increases in the cartridge removal force (i.e., the threshold force required to remove the cartridge after firing).

While various kinds of surgical staplers and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate examples of the invention, and, together with the general description of the invention given above, and the detailed description of the examples given below, serve to explain the principles of the present invention.

Figure 1:
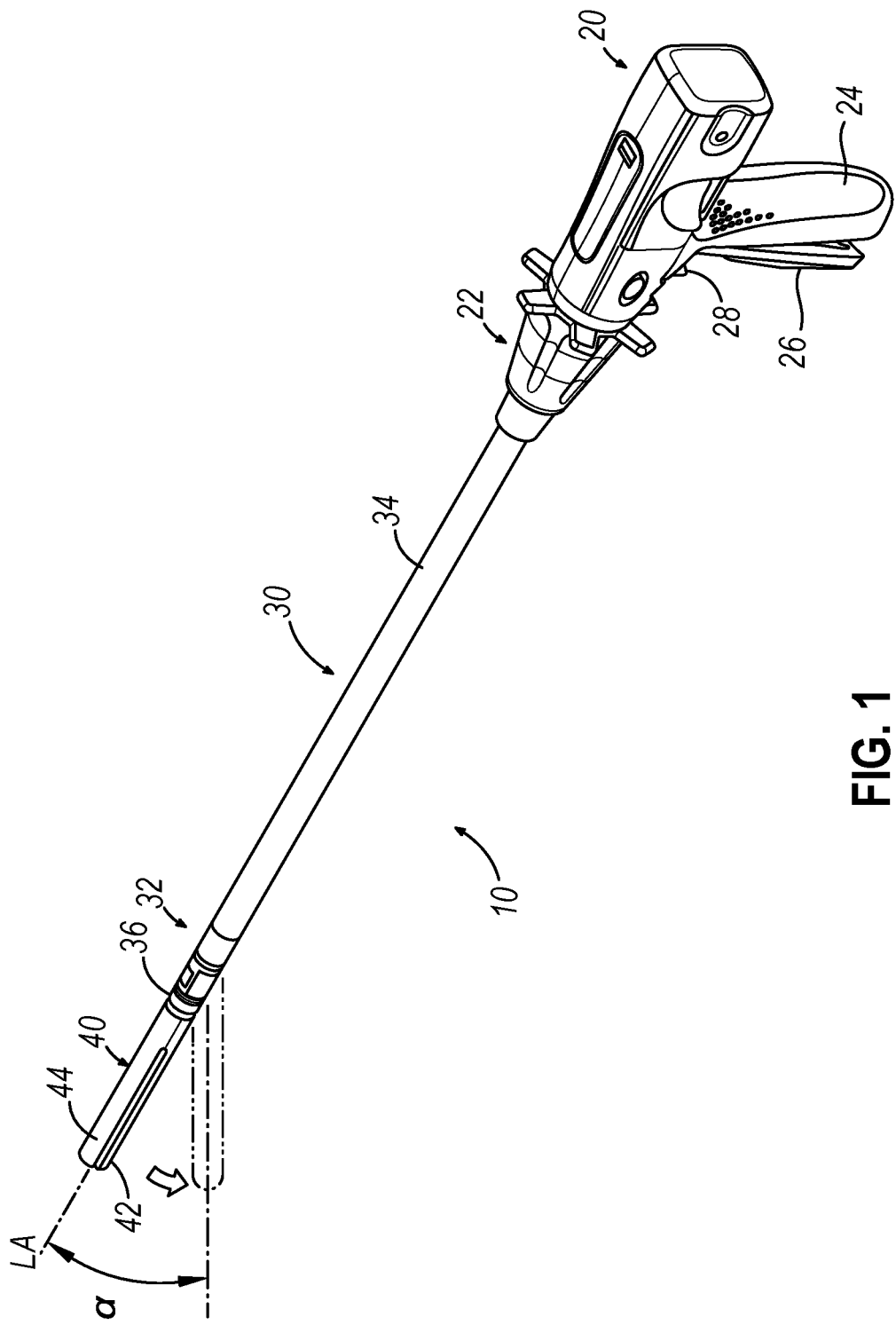
FIG. 1 depicts a perspective view of an example of a surgical stapler.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) referenced as well as a suitable tolerance that enables the referenced feature or combination of features to function for the intended purpose described herein. For example, "substantially parallel" encompasses nominally parallel structures.

As used herein in connection with any examples of end effector jaw tips, a tip described as "angled," "bent," or "curved" encompasses tip configurations in which a longitudinal path (e.g., linear or arcuate) along which the tip extends is non-coaxial and non-parallel with a longitudinal axis of the jaw body; particularly, configurations in which the longitudinal tip path extends distally toward the opposing jaw. Conversely, a tip described as "straight" encompasses tip configurations in which a longitudinal axis of the tip is substantially parallel or coaxial with the longitudinal axis of the jaw body.

I. Overview of Surgical Stapler Features

FIGS. 1-6 depict an illustrative surgical stapler (10) that is sized for insertion through a trocar cannula or a surgical incision (e.g., thoracotomy, etc.) to a surgical site in a patient for performing a surgical procedure. Surgical stapler (10) includes a body exemplified as a handle assembly (20), a shaft (30) that extends distally from handle assembly (20) along a longitudinal axis (LA) and distally terminates at an articulation joint (32), and an end effector (40) operatively coupled with shaft (30) via articulation joint (32).

Once end effector (40) and articulation joint (32) are inserted distally through the cannula passageway of a trocar, articulation joint (32) may be remotely articulated, as depicted in phantom in FIG. 1, by an articulation control exemplified as a rotatable knob (22) of handle assembly (20), such that end effector (40) may be deflected from the longitudinal axis (LA) at a desired angle (a). Articulation joint (32) and related features for manipulating articulation joint (32) may be further configured in accordance with the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein in its entirety.

End effector (40) includes a lower jaw exemplified as a cartridge jaw (42) configured to removably receive a staple cartridge (70) (also referred to as a "reload"), and an upper jaw exemplified as an anvil jaw (44) (also referred to as an "anvil") that pivots relative to cartridge jaw (42) to clamp tissue therebetween. In other versions, end effector (40) may be alternatively configured such that cartridge jaw (42) pivots relative to anvil jaw (44). Unless otherwise described, the term "pivot" (and variations thereof) as used herein in connection with the relative motion between jaws (42, 44) encompasses but is not necessarily limited to pivotal movement about a fixed axis. For instance, in some versions, anvil jaw (44) may pivot about an axis that is defined by a pin (or similar feature) that slidably translates along an elongate slot or channel as anvil jaw (44) moves toward cartridge jaw (42). Such translation may occur before, during, or after the pivotal motion. It should therefore be understood that such combinations of pivotal and translational movement are encompassed by the term "pivot" and variations thereof as used herein with reference to the relative motion between jaws (42, 44).

As shown in FIG. 1, handle assembly (20) includes a pistol grip (24) and a closure trigger (26). Closure trigger (26) is pivotable toward pistol grip (24) to cause clamping, or closing, of anvil jaw (44) toward cartridge jaw (42) of end effector (40). Such closing of anvil jaw (44) is provided through a closure tube (34) and a closure ring (36) of shaft (30), which both longitudinally translate relative to handle assembly (20) in response to pivoting of closure trigger (26) relative to pistol grip (24). Closure tube (34) extends along the length of shaft (30); and closure ring (36) is positioned distal to articulation joint (32). Articulation joint (32) is operable to transmit longitudinal movement from closure tube (34) to closure ring (36) to actuate anvil jaw (44) relative to cartridge jaw (42).

Handle assembly (20) also includes a firing trigger (28). An elongate actuator (not shown) extends longitudinally through shaft (30) and transmits a longitudinal firing motion from handle assembly (20) to a firing member (also referred to herein as a firing driver) exemplified as a firing beam (46) in response to actuation of firing trigger (28). As a result, firing beam (46) translates distally through a firing stroke to cause stapling and severing of tissue clamped by end effector (40), as will be described in greater detail below. Though not shown, handle assembly (20) may further include a motor operable to actuate such firing assembly components of surgical stapler (10) in response to actuation of firing trigger (28) by a user, for example as disclosed in U.S. Pat. No. 8,453,914, entitled "Motor-Driven Surgical Cutting Instrument with Electric Actuator Directional Control Assembly," issued Jun. 4, 2013, the disclosure of which is incorporated by reference herein in its entirety.

As shown in FIGS. 2-5, firing beam (46) includes a proximal beam portion (48) and a distal knife portion (50), where distal knife portion (50) may be integrally formed with a distal end of proximal beam portion (48), or separately formed and thereafter securely affixed to the distal end of proximal beam portion (17). Distal knife portion (50) includes a transversely oriented upper protrusion exemplified as an upper pin (52), a transversely oriented lower protrusion exemplified as a cap (54), a transversely oriented middle protrusion exemplified as a middle pin (56), and a distally presented cutting edge (58). Upper pin (52) is slidable within a longitudinal anvil jaw slot (62) of anvil jaw (44) and cap (54) is slidable along a lower surface of cartridge jaw (42) defined by a longitudinal cartridge jaw slot (64). Middle pin (56) is slidable along a top surface of cartridge jaw (42) and cooperates with cap (54) to stabilize and guide distal knife portion (50) along a longitudinal firing stroke. Firing beam (46) may be further configured and operable in accordance with the teachings of U.S. Pat. No. 9,717,497, entitled "Lockout Feature for Movable Cutting Member of Surgical Instrument," issued Aug. 1, 2017, the disclosure of which is incorporated by reference herein in its entirety.

Figure 2:
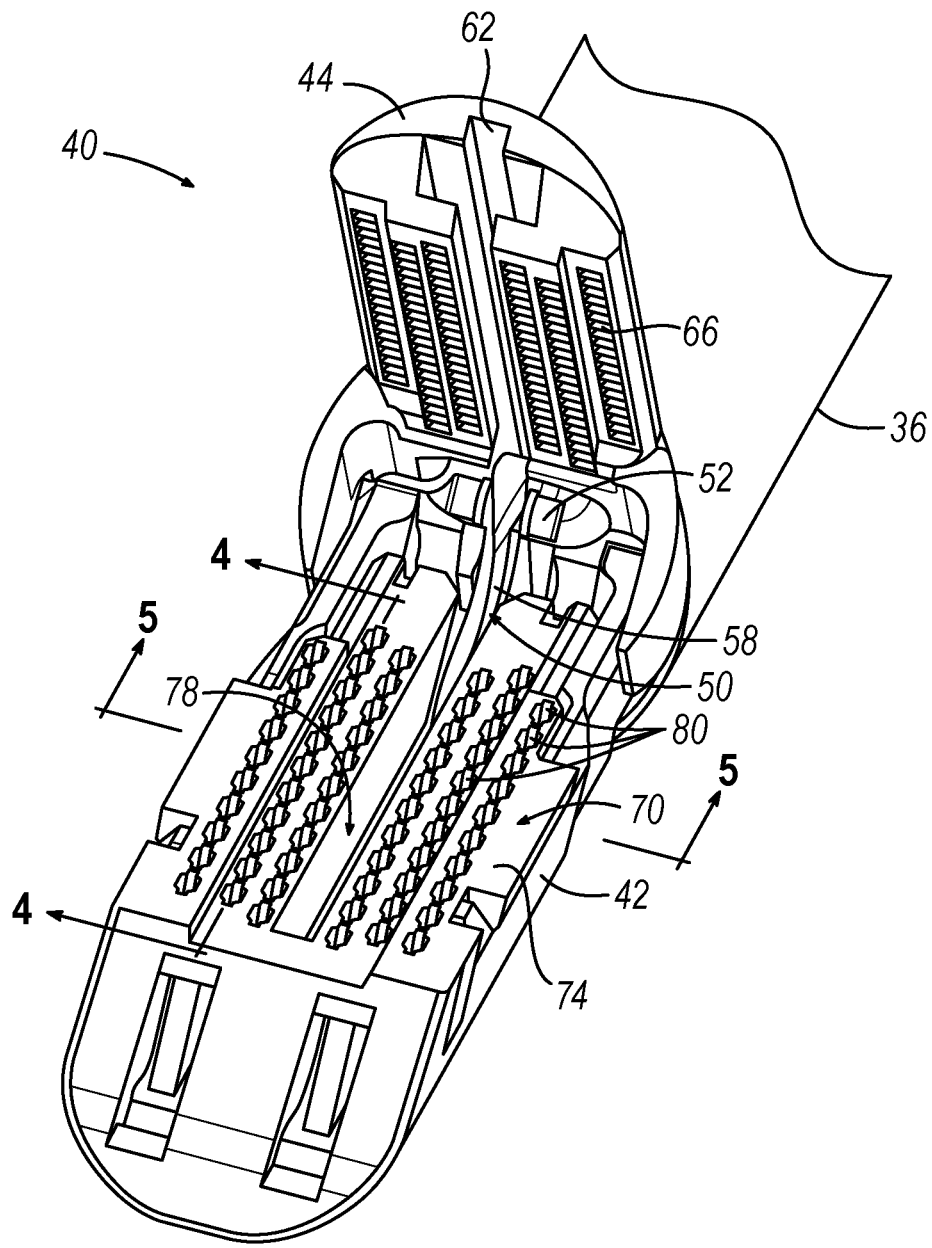
FIG. 2 depicts a perspective view of an end effector of the surgical stapler of FIG. 1, shown in an open state.
Figure 3:
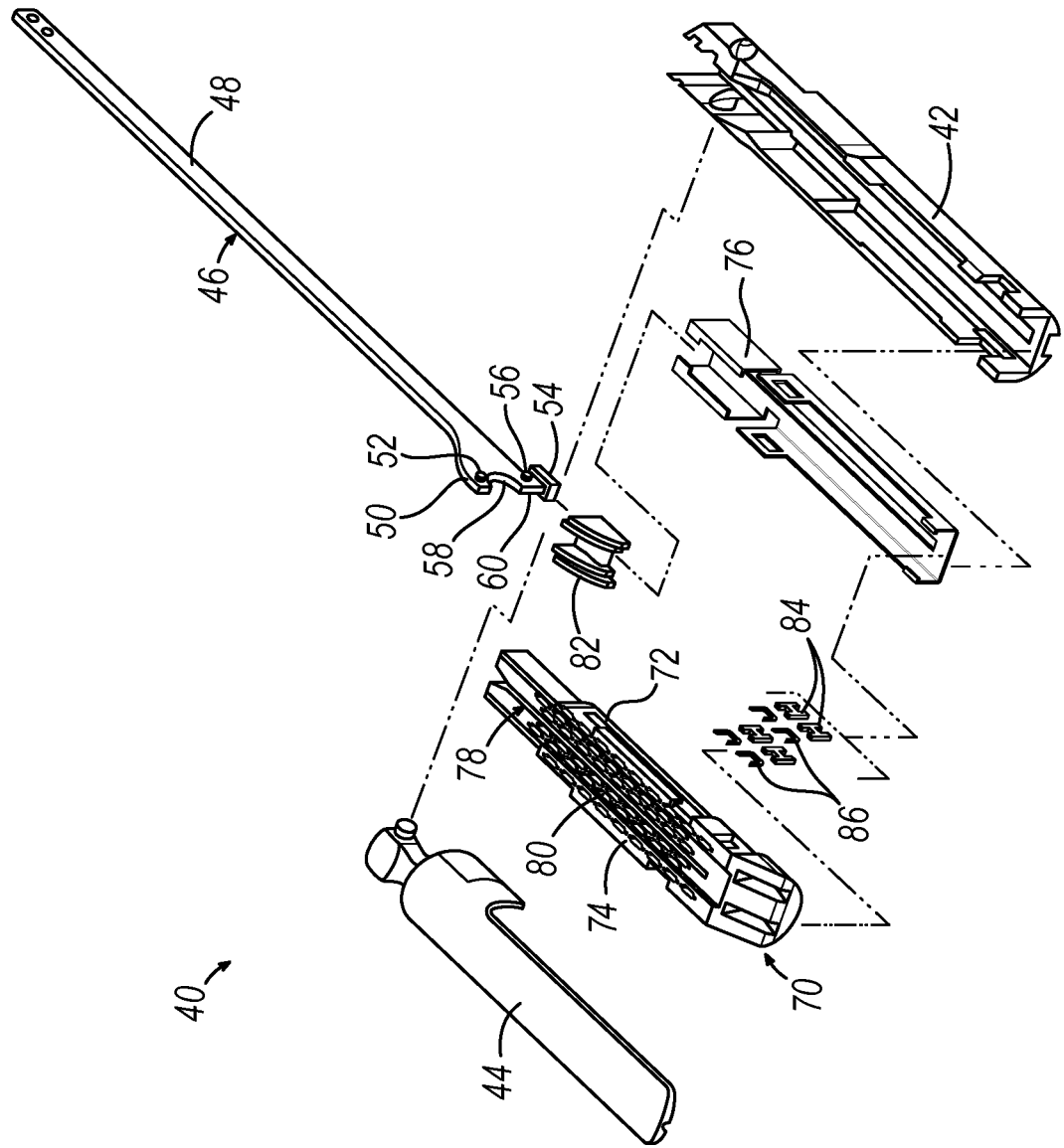
FIG. 3 depicts an exploded perspective view of the end effector of FIG. 2.

FIG. 2 shows anvil jaw (44) pivoted to an open state with firing beam (46) proximally positioned, which permits an unspent (i.e., unfired) staple cartridge (70) to be removably installed into a channel of cartridge jaw (42). As best seen in FIGS. 2-3, staple cartridge (70) includes a cartridge body (72) that presents an upper deck (74) defining a first stapling surface, and a lower pan (76) (also referred to as a "tray") coupled to an underside of cartridge body (72). A vertical knife slot (78) extends longitudinally through cartridge body

(72) and is configured to slidably receive distal knife portion (50) of firing beam (46). In the present version, three rows of cartridge pockets (80) (also referred to as "staple openings," "staple apertures," or "staple cavities") are formed through upper deck (74) along each lateral side of knife slot (78).

Figure 4A:
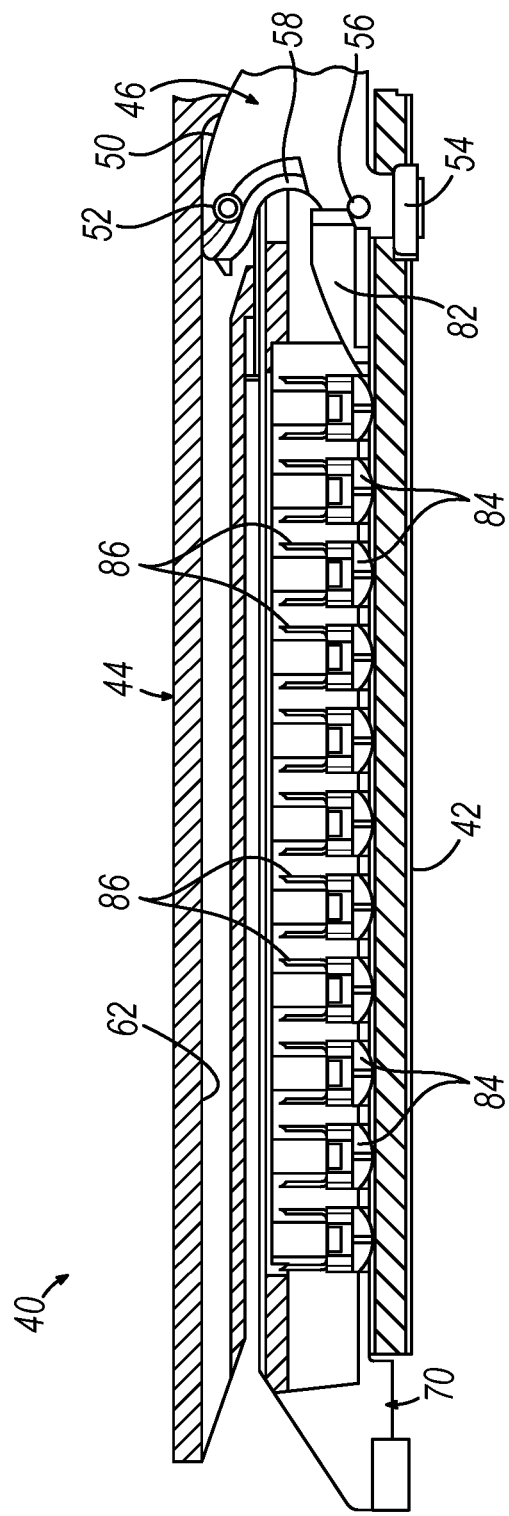
FIG. 4A depicts a side cross-sectional view of the end effector of FIG. 2, taken along line 4-4 of FIG. 2, showing a firing beam and sled in a proximal unfired position.
Figure 4B:
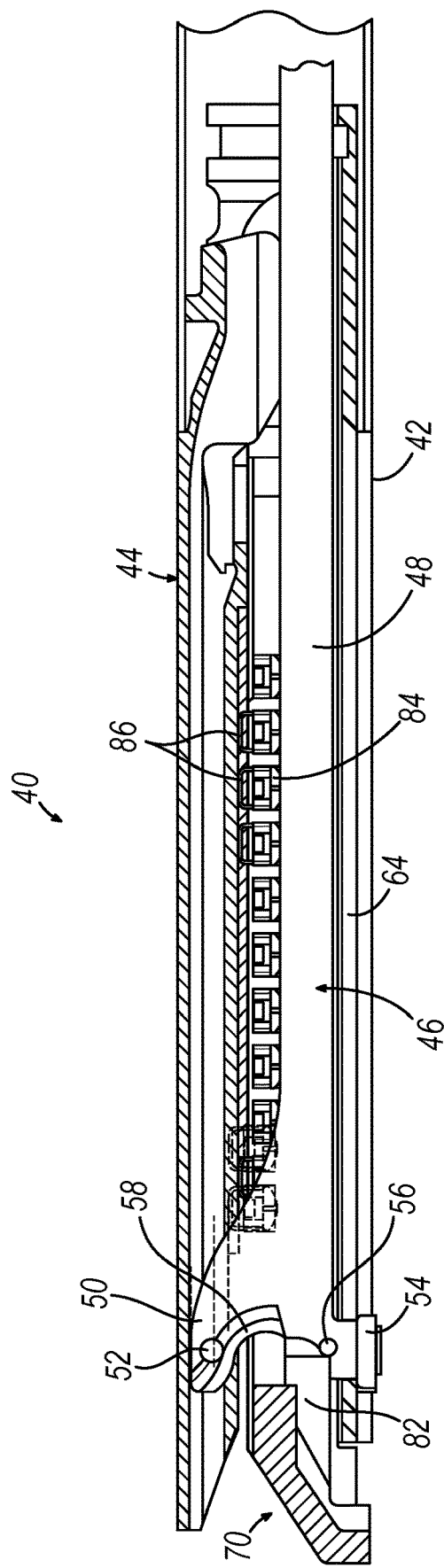
FIG. 4B depicts a side cross-sectional view of the end effector of FIG. 2, taken along line 4-4 of FIG. 2, showing the firing beam and sled in a distal fired position.
Figure 5:
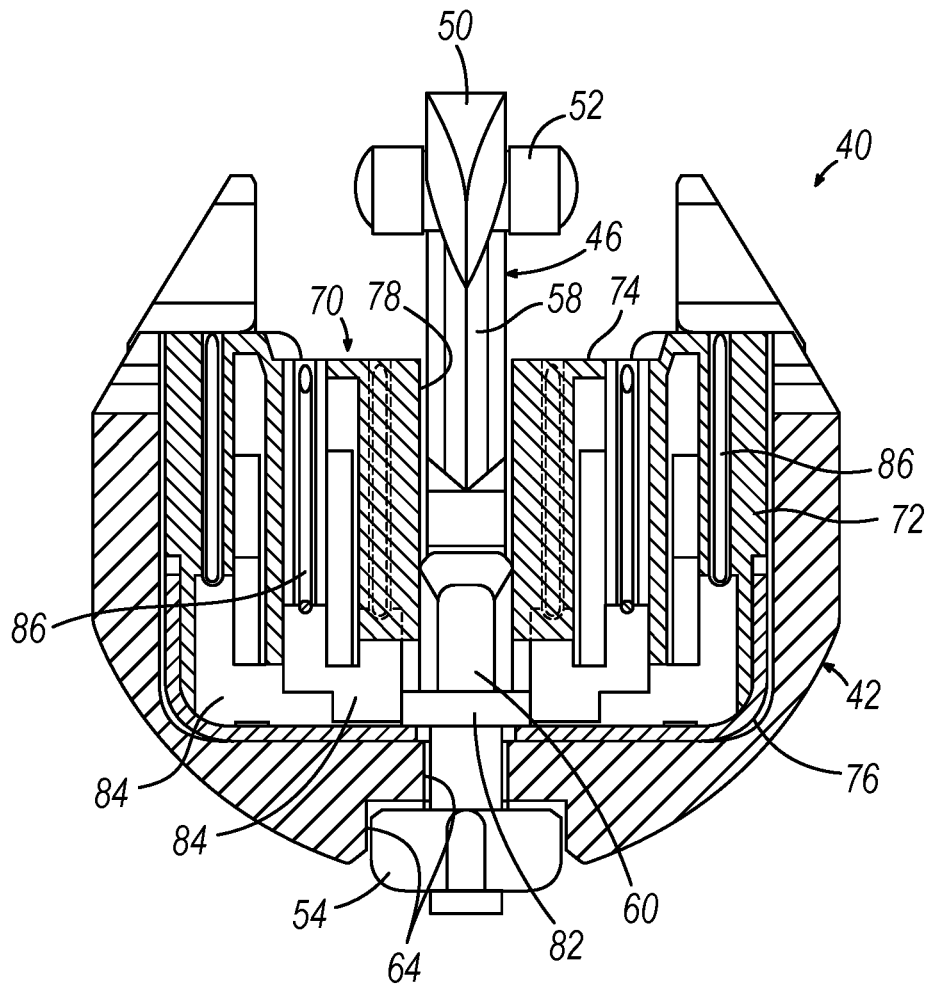
FIG. 5 depicts an end cross-sectional view of the end effector of FIG. 2, taken along line 5-5 of FIG. 2 and omitting an upper anvil jaw, showing further details of a distal knife portion of the firing beam and the sled.

As shown in FIGS. 3-5, staple cartridge (70) further includes a sled (82) (also referred to as a "wedge sled") and a plurality of staple drivers (84) that are movably captured between cartridge body (72) and pan (76). Each staple driver (43) is aligned with and movable vertically within a respective cartridge pocket (51). Staples (86) are positioned within respective cartridge pockets (80) above respective staple drivers (84). During a firing stroke, sled (82) is actuated longitudinally within staple cartridge (70) by distal knife portion (50) from a proximal position shown in FIG. 4A to a distal position shown in FIG. 4B. Angled cam surfaces of sled (82) cam staple drivers (84) vertically upwardly within cartridge pockets (80) to drive staples (86) upwardly above deck (74), thereby ejecting staples (86) from cartridge pockets (80) and toward anvil jaw (44).

More specifically, with end effector (40) closed as shown in FIGS. 4A-4B, firing beam (46) is actuated distally into engagement with anvil jaw (44) by directing upper pin (52) into longitudinal anvil slot (62). A distal end projection (60) (see FIG. 5) of distal knife portion (50) of firing beam (46) engages a proximal end of sled (82) and drives sled (82) distally as distal knife portion (50) is advanced distally through staple cartridge (70) in response to actuation of firing trigger (28). During such firing, distal knife portion (50) advances distally along knife slot (78) of staple cartridge (70) so that cutting edge (58) severs tissue clamped between staple cartridge (70) and anvil jaw (44).

As shown in FIGS. 4A-4B, middle pin (56) and distal end projection (60) together actuate staple cartridge (70) by entering into knife slot (78), driving sled (82) into camming contact with staple drivers (84) to thereby actuate staple drivers (84) upwardly, which in turn drives staples (86) outwardly through cartridge pockets (80), through clamped tissue, and into forming contact with staple forming pockets (66) (see FIG. 2) on a second stapling surface defined by anvil jaw (44). Such stapling of tissue prompted by the camming interaction between sled (82) and staple drivers (84) is performed concurrently with the severing of tissue performed by cutting edge (58). However, it will be appreciated that for each longitudinal section of tissue clamped by end effector (40), staples (86) may be ejected into the tissue slightly before cutting edge (58) severs the tissue to ensure that the tissue is stapled and thus sealed before being severed. FIG. 4B depicts firing beam (46) fully distally translated at the end of a firing stroke after the tissue clamped by end effector (40) has been stapled and severed.

Staple cartridge (70) and anvil jaw (44) may be further configured and operable in accordance with the teachings of U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; U.S. Pat. No. 10,092,292, entitled "Staple Forming Features for Surgical Stapling Instrument," issued Oct. 9, 2018; and/or U.S. Pat. No. 10,130,359, entitled "Method for Forming a Staple," issued Nov. 20, 2018, the disclosure of each of which is incorporated by reference herein in its entirety.

Figure 6:
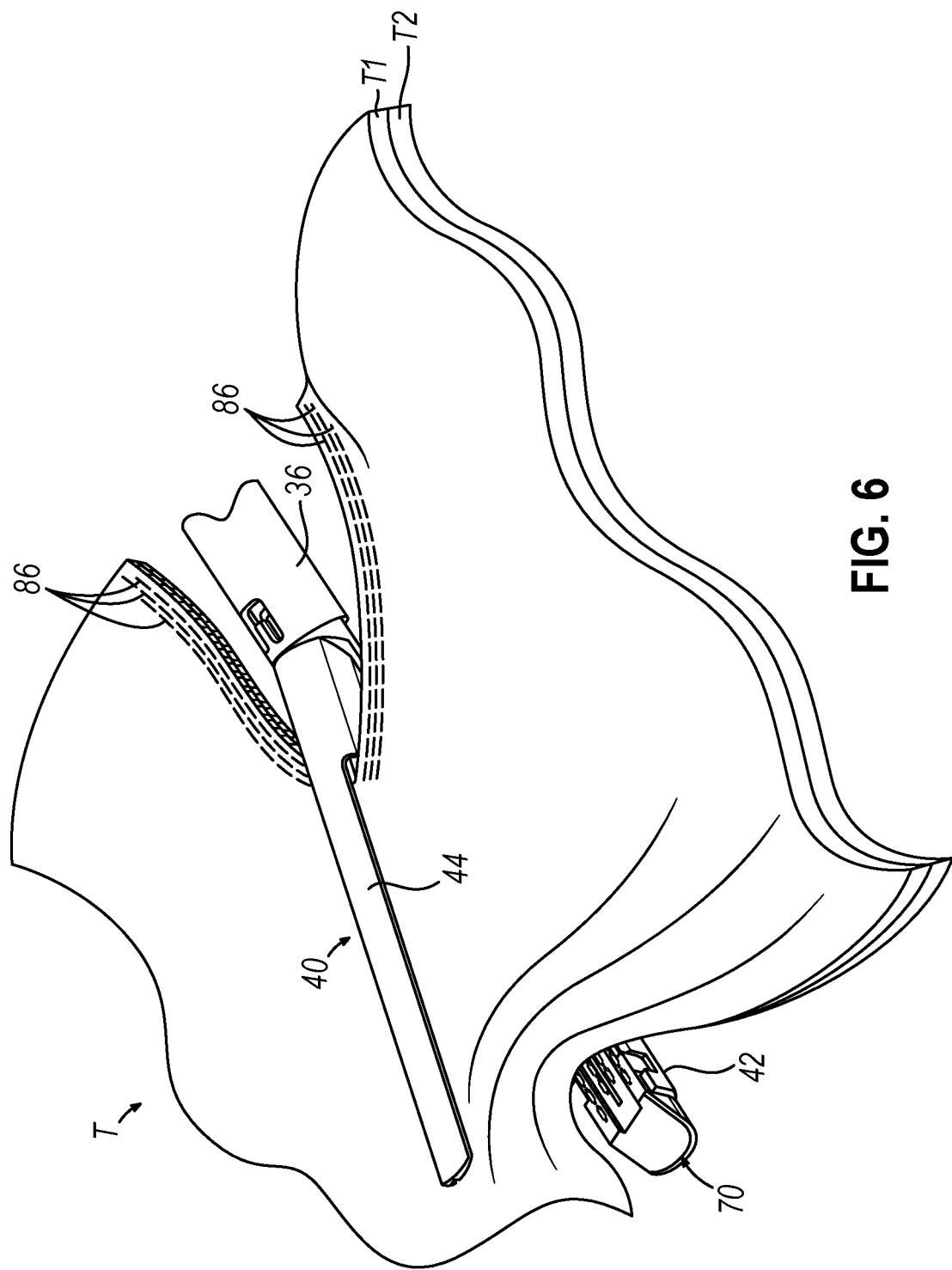
FIG. 6 depicts a perspective view of the end effector of FIG. 2, shown after having been fired once on a first section of tissue and being positioned to clamp and fire on a second section on tissue.

FIG. 6 shows end effector (40) having been actuated through a single firing stroke on tissue (T) having first and second layers (T1, T2). Cutting edge (58) (see FIGS. 2-5) has cut through tissue (T) while staple drivers (84) have driven three alternating rows of staples (86) through tissue (T) on each side of the cut line produced by cutting edge (58). After the first firing stroke is complete, end effector (40) is withdrawn from the patient, spent staple cartridge (70) is replaced with a new unspent staple cartridge (70), and end effector (40) is then again inserted into the patient to reach the stapling site for further cutting and stapling. This process may be repeated until the desired quantity and pattern of firing strokes across the tissue (T) has been completed.

II. Examples of Cartridge Pans Having Retention Tabs and Relief Slots

In some instances, it may be desirable to provide lower pan (76) of staple cartridge (70) with one or more retention tabs for frictionally engaging a channel of cartridge jaw (42) to resist dislodgment of staple cartridge (70) from the channel in the absence of a threshold amount of force applied between the staple cartridge (70) and the channel, at least when sled (82) is proximal of the distal fired position, such as when sled (82) is in the proximal unfired position (also referred to as the "cartridge retention force"); while avoiding undesirable increases in the threshold amount of force required to install staple cartridge (70) into the channel (also referred to as the "cartridge installation force") and/or in the threshold amount of force required to remove staple cartridge (70) from the channel when sled (82) is in the distal fired position (also referred to as the "cartridge removal force"). Each of the examples of lower pans (E110, E210, E310, E410, E510, E610, E710, E810, E910, E1010, E1110) described below provides such functionality.

Figure 7:
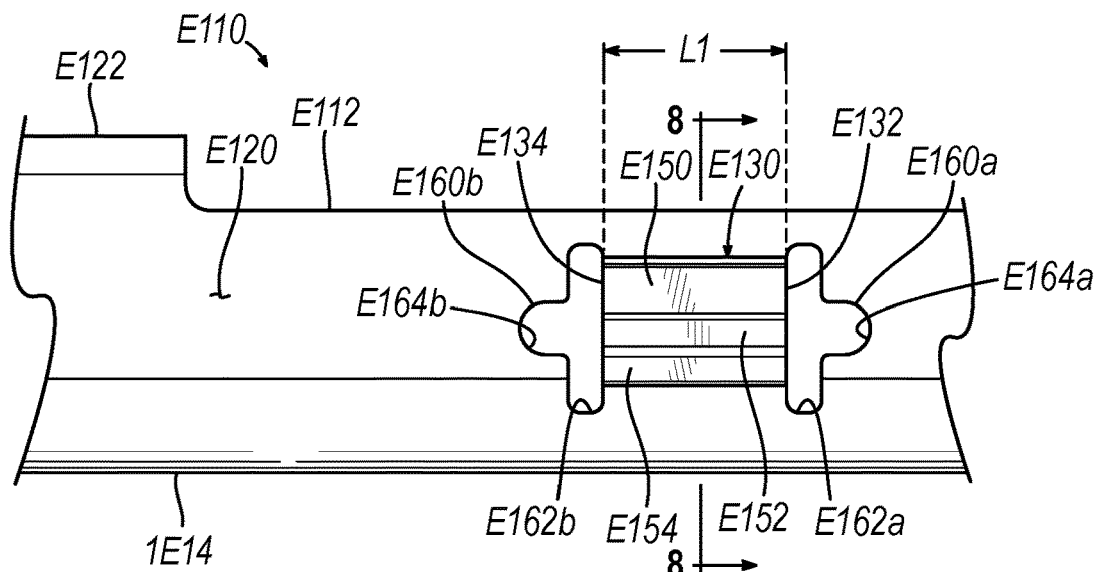
FIG. 7 depicts a partial side elevational view of another example of a lower pan of a staple cartridge for use with the end effector of FIG. 2 and having a retention tab extending laterally outwardly from a sidewall of the lower pan, the retention tab being longitudinally flanked by proximal and distal T-shaped relief slots.
Figure 8:
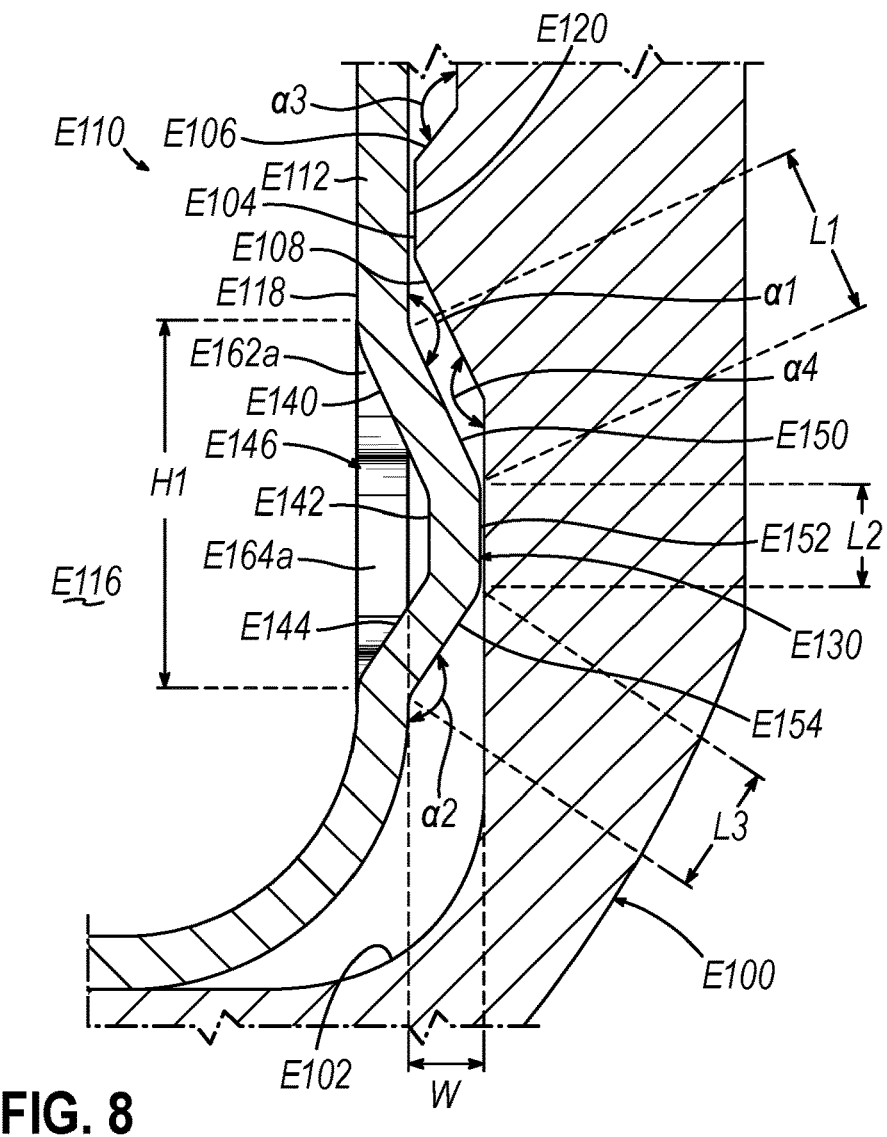
FIG. 8 depicts an end cross-sectional view of the lower pan of FIG. 7, taken along line 8-8 of FIG. 7, further showing an example of a channel of the lower cartridge jaw of the end effector of FIG. 2.

A. Example of Cartridge Pan with Retention Tab Longitudinally Flanked by T-Shaped Relief Slots FIGS. 7-8 show a portion of another example of a lower pan (E110) that may be readily incorporated into staple cartridge (70) in place of lower pan (76). Lower pan (E110) may be similar to lower pan (76) described above, except as otherwise described below. In this regard, lower pan (E110) may be configured to be coupled to an underside of cartridge body (72) such that sled (82) and staple drivers (84) may be movably captured between cartridge body (72) and pan (E110). Pan (E110) of the present example includes a laterally-opposed pair of sidewalls (E112) (one shown) coupled to each other by a bottom wall (E114), such that sidewalls (E112) and bottom wall (E114) collectively define a trough (E116) that is sized and configured to securely receive a cartridge body (not shown), such as cartridge body (72). Each sidewall (E112) has a respective laterally inner side surface (E118), which may confront and/or frictionally engage a respective laterally outer side surface of cartridge body (72); and a respective laterally outer side surface (E120), which may confront and/or frictionally engage a respective laterally inner side surface (E102) of a channel (E100) of a cartridge jaw (not shown), such as cartridge jaw (42). Pan (E110) also includes a laterally-opposed pair of distal retention arms (E122) (one shown) extending upwardly and laterally inwardly toward each other from upper ends of respective sidewalls (E112) for capturing cartridge body (72) within trough (E116). While pan (E110) is shown and described for incorporation into cartridge (70) and as being used in conjunction with channel (E100), it will be appreciated that pan (E110) may be incorporated into any other suitable cartridge and/or may be used in conjunction with any other suitable channel.

In the example shown, pan (E110) also includes a retention tab (also referred to as a "protrusion" or "bump") (E130) extending laterally outwardly from each sidewall (E112) for frictionally engaging a respective laterally inner side surface (E102) of channel (E100) to removably secure staple cartridge (70) within channel (E100) (e.g., with pan (E110) incorporated into staple cartridge (70) in place of pan (76)). Each retention tab (E130) may be disposed at a relatively distal location along a length of pan (E110). For example, each retention tab (E130) may be at a substantially same position in the longitudinal direction as sled (82) when sled (82) is in the distal fired position. Each retention tab (E130) extends longitudinally between respective proximal and distal ends (E132, E134), and includes an upper, laterally inner surface (E140) extending downwardly and laterally outwardly from an upper region of the laterally inner side surface (E118) of the respective sidewall (E112); a middle, laterally inner surface (E142) extending vertically downwardly from the respective upper, laterally inner surface (E140); and a lower, laterally inner surface (E144) extending downwardly and laterally inwardly from the respective middle, laterally inner surface (E142) to a lower region of the laterally inner side surface (E118) of the respective sidewall (E112).

As shown in FIG. 8, the upper, middle, and lower laterally inner surfaces (E140, E142, E144) of each retention tab (E130) collectively define a recess (E146) that extends laterally outwardly relative to the laterally inner side surface (E118) of the respective sidewall (E112), and likewise relative to trough (E116), for permitting laterally-inward flexing of the respective retention tab (E130) into the respective recess (E146). In the example shown, each recess (E146) is open-ended. More particularly, each recess (E146) is open at the proximal and distal ends (E132, E134) of the respective retention tab (E130), by opening through the respective sidewall (E112) and/or through the respective retention tab (E130) at each of the proximal and distal ends (E132, E134) of the respective retention tab (E130).

Each retention tab (E130) also includes an upper, laterally outer surface (also referred to as an "upper ramp surface") (E150) extending downwardly and laterally outwardly from an upper region of the laterally outer side surface (E120) of the respective sidewall (E112), such that each upper, laterally outer surface (E150) is oriented obliquely (e.g., obtusely) at a first angle ($\alpha 1$) relative to the laterally outer side surface (E120) of the respective sidewall (E112) and has a first length (L1) in a plane substantially orthogonal to the longitudinal direction; a middle, laterally outer surface (also referred to as an "engagement surface") (E152) extending vertically downwardly from the respective upper, laterally outer surface (E150), such that each middle, laterally outer surface (E152) is oriented substantially parallel relative to the laterally outer side surface (E120) of the respective sidewall (E112) and has a second length (L2) in the plane substantially orthogonal to the longitudinal direction; and a lower, laterally outer surface (also referred to as a "lower ramp surface") (E154) extending downwardly and laterally inwardly from the respective middle, laterally outer surface (E152) to a lower region of the laterally outer side surface (E120) of the respective sidewall (E112), such that each lower, laterally outer surface (E154) is oriented obliquely (e.g., obtusely) at a second angle ($\alpha 2$) relative to the laterally outer side surface (E120) of the respective sidewall (E112) and has a third length (L3) in the plane substantially orthogonal to the longitudinal direction.

Each retention tab (E130) has a length (L) in the longitudinal direction defined between the respective proximal and distal ends (E132, E134) selected to provide a desired cartridge removal force and/or a desired cartridge installation force. For example, a greater length (L) of each retention tab (E130) may increase the removal and/or installation force(s), while a lesser length (L) of each retention tab (E130) may decrease the removal and/or installation force (s). Each retention tab (E130) also has a height (H1) in the vertical direction defined between the interface of the respective lower, laterally inner surface (E144) with the laterally inner side surface (E118) of the respective sidewall (E112), and the interface of the respective upper, laterally inner surface (E140) with the laterally inner side surface (E118) of the respective sidewall (E112). In some versions, the height (H1) of each retention tab (E130) may be selected to provide a desired cartridge removal force and/or a desired cartridge installation force. For example, a greater height (H1) of each retention tab (E130) may decrease the removal and/or installation force(s), while a lesser height (H1) of each retention tab (E130) may increase the removal and/or installation force(s). Each retention tab (E130) further has a width (W) in the lateral direction defined between the laterally outer side surface (E120) of the respective sidewall (E112) and the respective middle, laterally outer surface (E152). In some versions, the width (W) of each retention tab (E130) may be selected to provide a desired cartridge removal force and/or a desired cartridge installation force. For example, a greater width (W) of each retention tab (E130) may increase the removal and/or installation force (s), while a lesser width (W) of each retention tab (E130) may decrease the removal and/or installation force(s).

As shown, each retention tab (E130) may have a substantially uniform material thickness, and/or may have a substantially same material thickness as that of the respective sidewall (E112). For example, the material thickness defined between the respective upper, laterally inner and outer surfaces (E140, E150) may be substantially equal to each of the material thickness defined between the respective middle, laterally inner and outer surfaces (E142, E152) and the material thickness defined between the respective lower, laterally inner and outer surfaces (E144, E154), and/or may be substantially equal to the material thickness defined between the respective laterally inner and outer side surfaces (E118, 120) of the respective sidewall (E112).

In the example shown, each middle, laterally outer surface (E152) is substantially flat (e.g., planar) and is configured to be oriented substantially parallel to the respective laterally inner side surface (E102) of channel (E100) (e.g., at least when staple cartridge (70) is removably received within channel (E100)) and to frictionally engage the respective laterally inner side surface (E102) of channel (E100). In some versions, each middle, laterally outer surface (E152) may be curved in a convex manner. In addition, or alternatively, each retention tab (E130) may include one or more laterally-outwardly extending ridges and/or laterally-inwardly extending indentations provided along the respective middle, laterally outer surface (E152). It will be appreciated that such features may alter the surface area of the respective middle, laterally outer surface (E152) to adjust the cartridge retention and/or removal force(s) relative to that provided by the example shown. For example, the surface area of the respective middle, laterally outer surface (E152) may be decreased to decrease the retention and/or removal force(s), or may be increased to increase the retention and/or removal force(s). In some versions, the second length (L2) of each middle, laterally outer surface (E152) may be selected to provide a desired cartridge removal force and/or a desired cartridge installation force. For example, a greater second length (L2) of each middle, laterally outer surface (E152) may increase the removal and/or installation force(s), while a lesser second length (L2) of each middle, laterally outer surface (E152) may decrease the removal and/or installation force(s).

First and second angles (α1, α2) may each be selected based on one or more features of channel (E100). In this regard, channel (E100) shown in FIG. 8 includes a laterally-opposed pair of detents (E104) (one shown) extending laterally inwardly from respective laterally inner side surfaces (E102) of channel (E100) and configured to be directly above respective retention tabs (E130) when staple cartridge (70) removably received within channel (E100) to assist with inhibiting inadvertent dislodgment of staple cartridge (70) from channel (E100). Each detent (E104) includes an upper surface (E106) extending downwardly and laterally inwardly from the respective laterally inner side surface (E102) of channel, such that each upper surface (E106) is oriented obliquely (e.g., obtusely) at a third angle (α3) relative to the respective laterally inner side surface (E102) of channel (E100); and a lower surface (E108) extending upwardly and laterally inwardly from the respective laterally inner side surface (E102) of channel toward the respective upper surface (E106), such that each lower surface (E108) is oriented obliquely (e.g., obtusely) at a fourth angle (α4) relative to the respective laterally inner side surface (E102) of channel (E100).

In the example shown, first angle (α1) is substantially equal to fourth angle (α4) such that the upper, laterally outer surface (E150) of each retention tab (E130) is substantially parallel to the lower surface (E108) of the corresponding detent (E104) (e.g., at least when staple cartridge (70) is removably received within channel (E100)) to directly confront the lower surface (E108) of the corresponding detent (E104) when staple cartridge (70) is removably received within channel (E100) and thereby assist with inhibiting inadvertent dislodgment of staple cartridge (70) from channel (E100), and/or to promote a camming interaction between the upper, laterally outer surface (E150) of each retention tab (E130) and the lower surface (E108) of the corresponding detent (E104) for urging each retention tab (E130) laterally inwardly into the respective recess (E146) during removal of staple cartridge (70) from channel (E100). It will be appreciated that first angle (α1) may alternatively be substantially different from fourth angle (α4) to adjust the cartridge retention and/or removal force(s) relative to that provided by the example shown. For example, first angle (α1) may be substantially greater than fourth angle (α4) to decrease the retention and/or removal force(s), or may be substantially less than fourth angle (α4) to increase the retention and/or removal force(s). In addition, or alternatively, a greater first angle (α1) of each upper, laterally outer surface (E150) may decrease the retention and/or removal force(s), while a lesser first angle (α1) of each upper, laterally outer surface (E150) may increase the retention and/or removal force(s). In some versions, the first length (L1) of each upper, laterally outer surface (E150) may be selected to provide a desired cartridge retention force and/or a desired cartridge removal force. For example, a greater first length (L1) of each upper, laterally outer surface (E150) may increase the retention and/or removal force(s), while a lesser first length (L1) of each upper, laterally outer surface (E150) may decrease the retention and/or removal force(s).

In the example shown, second angle (α2) is substantially equal to third angle (α3) such that the lower, laterally outer surface (E154) of each retention tab (E130) is substantially parallel to the upper surface (E106) of the corresponding detent (E104) (e.g., at least when staple cartridge (70) is removably received within channel (E100)) to promote a camming interaction between the lower, laterally outer surface (E154) of each retention tab (E130) and the upper surface (E106) of the corresponding detent (E104) for urging each retention tab (E130) laterally inwardly into the respective recess (E146) during installation of staple cartridge (70) into channel (E100). It will be appreciated that second angle (α2) may alternatively be substantially different from third angle (α3) to adjust the installation force relative to that provided by the example shown. For example, second angle (α2) may be substantially greater than third angle (α3) to decrease the installation force, or may be substantially less than third angle (α3) to increase the installation force. In addition, or alternatively, a greater second angle (α2) of each lower, laterally outer surface (E154) may decrease the installation force, while a lesser second angle (α2) of each lower, laterally outer surface (E154) may increase the installation force. In some versions, the third length (L3) of each lower, laterally outer surface (E154) may be selected to provide a desired cartridge installation force. For example, a greater third length (L3) of each lower, laterally outer surface (E154) may increase the installation force, while a lesser third length (L3) of each lower, laterally outer surface (E154) may decrease the installation force.

It will be appreciated that first and second angles (α1, α2) may be substantially different from each other, such that upper and lower laterally outer surfaces (E150, E154) may have substantially different heights from each other. For example, first angle (α1) may be substantially greater than second angle (α2), such that upper laterally outer surfaces (E150) may each be substantially taller than the corresponding lower laterally outer surface (E154). While upper and lower laterally outer surfaces (E150, E154) of the present example are each substantially flat (e.g., planar), any one or more of upper or lower laterally outer surfaces (E150, E154) may alternatively be curved. For example, each upper, laterally outer surface (E150) may be defined by a first radius, and each lower, laterally outer surface (E154) may be defined by a second radius substantially different from (e.g., greater than) the first radius.

In the example shown, pan (E110) also includes a pair of relief slots (also referred to as "cutouts") (E160a, E160b) extending laterally through each sidewall (E112) from the inner side surface (E118) thereof to the laterally outer side surface (E120) thereof. Each relief slot (E160a, E160b) is positioned adjacent to a corresponding retention tab (E130) to impart the corresponding retention tab (E130) with a reduced stiffness and/or increased resilience. In this regard, each pair of relief slots (E160a, E160b) includes a proximal relief slot (E160a) positioned adjacent to the proximal end (E132) of the corresponding retention tab (E130), and a distal relief slot (E160b) positioned adjacent to the distal end (E134) of the corresponding retention tab (E130), such that each retention tab (E130) is longitudinally flanked by a corresponding pair of relief slots (E160a, E160b). Each relief slot (E160a, E160b) includes a respective vertical slot portion (E162a, E162b) extending along the respective end (E132, E134) of the corresponding retention tab (E130), and a respective horizontal slot portion (E164a, E164b) extending longitudinally from a middle region of the respective vertical slot portion (E162a, E162b), such that each relief slot (E160a, E160b) is substantially T-shaped. More particularly, the vertical slot portion (E162a) of each proximal relief slot (E160a) extends along the proximal end (E132) of the corresponding retention tab (E130), and the horizontal slot portion (E164a) of each proximal relief slot (E160a) extends proximally from the middle region of the respective vertical slot portion (E162a). Similarly, the vertical slot portion (E162b) of each distal relief slot (E160b) extends along the distal end (E134) of the corresponding retention tab (E130), and the horizontal slot portion (E164b) of each distal relief slot (E160b) extends distally from the middle region of the respective vertical slot portion (E162b). Due to each recess (E146) being open-ended as described above, vertical slot portions (E162a, E162b) of proximal and distal relief slots (E160a, E160b) may open directly into recess (E146).

By imparting the corresponding retention tab (E130) with a reduced stiffness and/or increased resilience, relief slots (E160a, E160b) may promote flexing of the corresponding retention tab (E130) laterally inwardly into the respective recess (E146), such as during installation of staple cartridge (70) into channel (E100) and/or during removal of staple cartridge (70) from channel (E100). For example, relief slots (E160a, E160b) may assist with allowing the corresponding retention tab (E130) to flex laterally inwardly into the respective recess (E146) via the camming interaction between the lower, laterally outer surface (E154) of each retention tab (E130) and the upper surface (E106) of the corresponding detent (E104) during installation of staple cartridge (70) into channel (E100), and/or may cause the corresponding retention tab (E130) to resiliently flex laterally outwardly from the respective recess (E146) in response to the corresponding retention tab (E130) disengaging the corresponding detent (e.g., when the corresponding retention tab (E130) reaches a position substantially below the corresponding detent (E104)). In addition, or alternatively, relief slots (E160a, E160b) may assist with allowing the corresponding retention tab (E130) to flex laterally inwardly into the respective recess (E146) via the camming interaction between the upper, laterally outer surface (E150) of each retention tab (E130) and the lower surface (E108) of the corresponding detent (E104) during removal of staple cartridge (70) from channel (E100), and/or may cause the corresponding retention tab (E130) to resiliently flex laterally outwardly from the respective recess (E146) in response to the corresponding retention tab (E130) disengaging the corresponding detent (E104) (e.g., when the corresponding retention tab (E130) reaches a position substantially above the corresponding detent (E104)). In other words, relief slots (E160a, E160b) may enhance the spring-like characteristics of the corresponding retention tabs (E130).

While each relief slot (E160a, E160b) of the present example is substantially T-shaped, it will be appreciated that each relief slot (E160a, E160b) may have any other suitable shape and/or size, such as any of those described elsewhere herein, and that such variations in shape and/or size may adjust the cartridge installation and/or removal force(s) relative to that provided by the example shown. For example, the size of each relief slot (E160a, E160b) may be increased to decrease the installation and/or removal force(s), or may be decreased to increase the installation and/or removal force(s). In some versions, each proximal relief slot (E160a) may be sized and/or shaped substantially differently from the respective distal relief slot (E160b) such that each pair of relief slots (E160a, E160b) may be asymmetrical relative to the respective retention tab (E130). In some other versions, either each proximal or distal relief slot (E160a, E160b) may be omitted.

In some versions, relief slots (E160a, E160b) may also improve manufacturability of pan (E110), such as by providing improved forming control of the ends (E132, E134) and/or surfaces (E140, E142, E144, E150, E152, E154) of the corresponding retention tab (E130). In this manner, the inclusion of relief slots (E160a, E160b) may reduce part-to-part variations when manufacturing multiple pans (E110).

While retention tabs (E130) and relief slots (E160a, E160b) may be arranged on sidewalls (E112) in laterally-opposed pairs with each laterally-opposed pair of retention tabs (E130) and each laterally-opposed pair of relief slots (E160a, E160b) being symmetrical relative to a longitudinal axis of pan (E110), retention tabs (E130) and/or relief slots (E160a, E160b) may alternatively be configured substantially differently on each sidewall (E112) of pan (E110) so as to be asymmetrical relative to the longitudinal axis of pan (E110). For example, the retention tab (E130) and relief slots (E160a, E160b) on one sidewall (E112) may be offset in the vertical direction and/or offset in the longitudinal direction from the retention tab (E130) and relief slots (E160a, E160b) on the other sidewall (E112). In addition, or alternatively, the retention tab (E130) and relief slots (E160a, E160b) on one sidewall (E112) may be sized and/or shaped substantially differently from the retention tab (E130) and relief slots (E160a, E160b) on the other sidewall (E112), such as by being sized and/or shaped in accordance with any of the other teachings provided herein.

Figure 9:
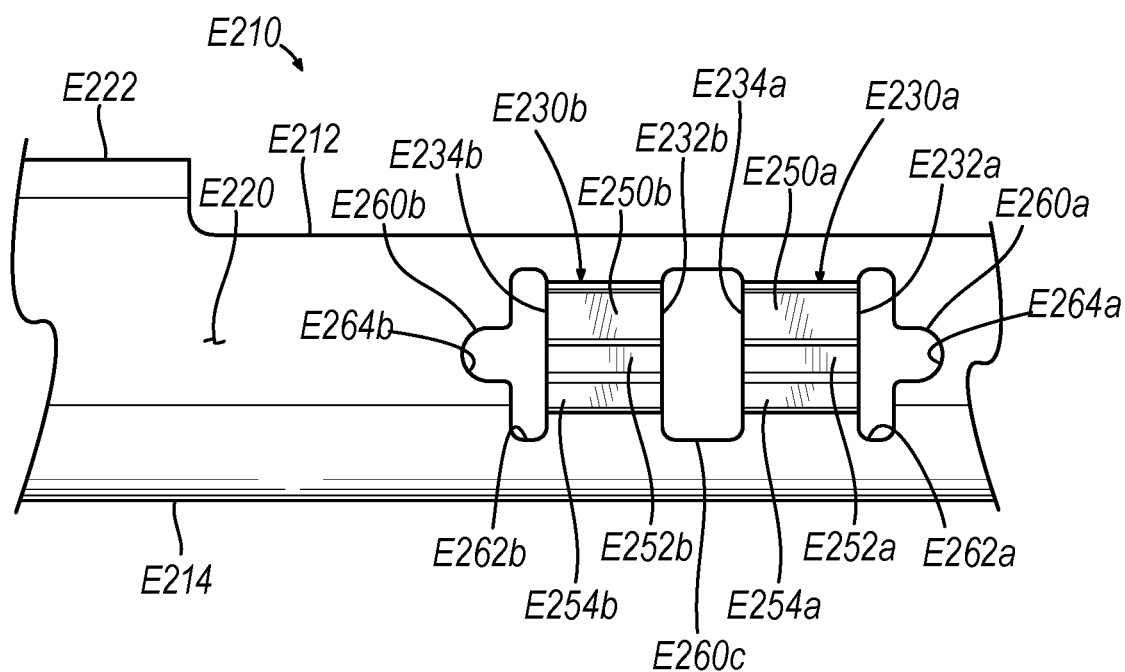
FIG. 9 depicts a partial side elevational view of another example of a lower pan of a staple cartridge for use with the end effector of FIG. 2 and having a pair of retention tabs extending laterally outwardly from a sidewall of the lower pan, the retention tabs being collectively longitudinally flanked by proximal and distal T-shaped relief slots and being spaced apart from each other by an intermediate elongate relief slot.

B. Example of Cartridge Pan with Pair of Retention Tabs Spaced Apart by Elongate Relief Slot and Longitudinally Flanked by T-Shaped Relief Slots FIG. 9 shows a portion of another example of a lower pan (E210) that may be readily incorporated into staple cartridge (70) in place of lower pan (76). Lower pan (E210) may be similar to lower pan (E110) described above, except as otherwise described below. In this regard, lower pan (E210) may be configured to be coupled to an underside of cartridge body (72) such that sled (82) and staple drivers (84) may be movably captured between cartridge body (72) and pan (E210). Pan (E210) of the present example includes a laterally-opposed pair of sidewalls (E212) (one shown) coupled to each other by a bottom wall (E214), such that sidewalls (E212) and bottom wall (E214) collectively define a trough (not shown) similar to trough (E116) that is sized and configured to securely receive a cartridge body (not shown), such as cartridge body (72). Each sidewall (E212) has a respective laterally inner side surface (not shown) similar to laterally inner side surfaces (E118), which may confront and/or frictionally engage a respective laterally outer side surface of cartridge body (72); and a respective laterally outer side surface (E220), which may confront and/or frictionally engage a respective laterally inner side surface (E102) of a channel (E100) of a cartridge jaw (not shown), such as cartridge jaw (42). Pan (E210) also includes a laterally-opposed pair of distal retention arms (E222) (one shown) extending upwardly and laterally inwardly toward each other from upper ends of respective sidewalls (E212) for capturing cartridge body (72) within the trough. While pan (E210) is shown and described for incorporation into cartridge (70) and as being used in conjunction with channel (E100), it will be appreciated that pan (E210) may be incorporated into any other suitable cartridge and/or may be used in conjunction with any other suitable channel.

In the example shown, pan (E210) also includes a pair of retention tabs (E230a, E230b) extending laterally outwardly from each sidewall (E212). In this regard, each pair of retention tabs (E230a, E230b) includes a proximal retention tab (E230a) and a distal retention tab (E230b). Each retention tab (E230a, E230b) extends longitudinally between a respective proximal end (E232a, E232b) and a respective distal end (E234a, E234b), and includes laterally inner surfaces that collectively define a respective open-ended recess (not shown) similar to recess (E146) for permitting laterally-inward flexing of the respective retention tab (E230a, E230b) into the respective recess. Each retention tab (E230a, E230b) also includes an upper, laterally outer surface (E250a, E250b) extending downwardly and laterally outwardly from an upper region of the laterally outer side surface (E220) of the respective sidewall (E212), a middle, laterally outer surface (E252a, E252b) extending vertically downwardly from the respective upper, laterally outer surface (E250a, E250b), and a lower, laterally outer surface (E254a, E254b) extending downwardly and laterally inwardly from the respective middle, laterally outer surface (E252a, E252b) to a lower region of the laterally outer side surface (E220) of the respective sidewall (E212).

While each proximal retention tab (E230a) is shown as having a substantially same length as the respective distal retention tab (E230b), the length of each proximal retention tab (E230a) may alternatively be substantially different from that of the respective distal retention tab (E230b), such as to provide a desired cartridge removal force and/or a desired cartridge installation force.

In the example shown, pan (E210) also includes a plurality of relief slots (E260a, E260b, E260c) extending laterally through each sidewall (E212) from the inner side surface thereof to the laterally outer side surface (E220) thereof. Each relief slot (E260a, E260b, E260c) is positioned adjacent to at least one corresponding retention tab (E230a, E230b) to impart the corresponding retention tab(s) (E230a, E230b) with a reduced stiffness and/or increased resilience. In this regard, each plurality of relief slots (E260a, E260b, E260c) includes a proximal relief slot (E260a) positioned adjacent to the proximal end (E232a) of the proximal retention tab (E230a), and a distal relief slot (E260b) positioned adjacent to the distal end (E234b) of the distal retention tab (E230b), such that each pair of retention tabs (E230a, E230b) is longitudinally flanked by a corresponding pair of proximal and distal relief slots (E260a, E260b); and further includes an intermediate relief slot (E260c) positioned adjacent to and/or extending along both the distal end (E234a) of the proximal retention tab (E230a) and the proximal end (E232b) of the distal retention tab (E230b), such that each pair of retention tabs (E230a, E230b) is spaced apart from each other by the corresponding intermediate relief slot (E260c). Each proximal and distal relief slot (E260a, E260b) includes a respective vertical slot portion (E262a, E262b) extending along the respective end (E232a, E234b) of the corresponding retention tab (E230a, E230b), and a respective horizontal slot portion (E264a, E264b) extending longitudinally from a middle region of the respective vertical slot portion (E262a, E162b), such that each proximal and distal relief slot (E260a, E260b) is substantially T-shaped; while each intermediate relief slot (E260c) is substantially elongate (e.g., linear, rectangular, rectangular with rounded corners, obround, etc.). Due to the recess of each retention tab (E230a, E230b) being open-ended as described above, vertical slot portions (E262a, E262b) of proximal and distal relief slots (E260a, E260b) may each open directly into the respective recess, and each intermediate relief slot (E260c) may likewise open directly into both respective recesses.

As with proximal and distal relief slots (E260a, E260b), it will be appreciated that each intermediate relief slot (E260c) may have any other suitable shape and/or size than that shown, such as any of those described elsewhere herein, and that such variations in shape and/or size may adjust the cartridge installation and/or removal force(s) relative to that provided by the example shown.

By having multiple retention tabs (E230a, E230b) along each sidewall (E212), pan (E210) may be particularly suitable for use with a channel (E100) having a laterally inner side surface (E102) that is non-uniform along a length of the channel (E100), such as a channel (E100) having a laterally inner side surface that tapers, steps, and/or curves along the length of the channel (E100). For example, each retention tab (E230a, E230b) may be configured to frictionally engage a corresponding portion of the laterally inner side surface (E102) even in cases where such portions of the laterally inner side surface (E102) are non-uniformly spaced apart from laterally outer side surface (E220) when cartridge (70) is removably installed into the channel (E100).

In some versions, retention tabs (E230a, E230b) and relief slots (E260a, E260b, E260c) may be arranged on sidewalls (E212) in laterally-opposed pairs with each laterally-opposed pair of retention tabs (E230a, E230b) and each laterally-opposed pair of relief slots (E260a, E260b, E260c) being symmetrical relative to a longitudinal axis of pan (E210). In other versions, retention tabs (E230a, E230b) and/or relief slots (E260a, E260b, E260c) may alternatively be configured substantially differently on each sidewall (E212) of pan (E210) so as to be asymmetrical relative to the longitudinal axis of pan (E210). For example, the retention tab (E230a, E230b) and relief slots (E260a, E260b, E260c) on one sidewall (E212) may be offset in the vertical direction and/or offset in the longitudinal direction from the retention tab (E230a, E230b) and relief slots (E260a, E260b, E260c) on the other sidewall (E212). In addition, or alternatively, the retention tab (E230a, E230b) and relief slots (E260a, E260b, E260c) on one sidewall (E212) may be sized and/or shaped substantially differently from the retention tab (E230a, E230b) and relief slots (E260a, E260b, E260c) on the other sidewall (E212), such as by being sized and/or shaped in accordance with any of the other teachings provided herein.

Figure 10:
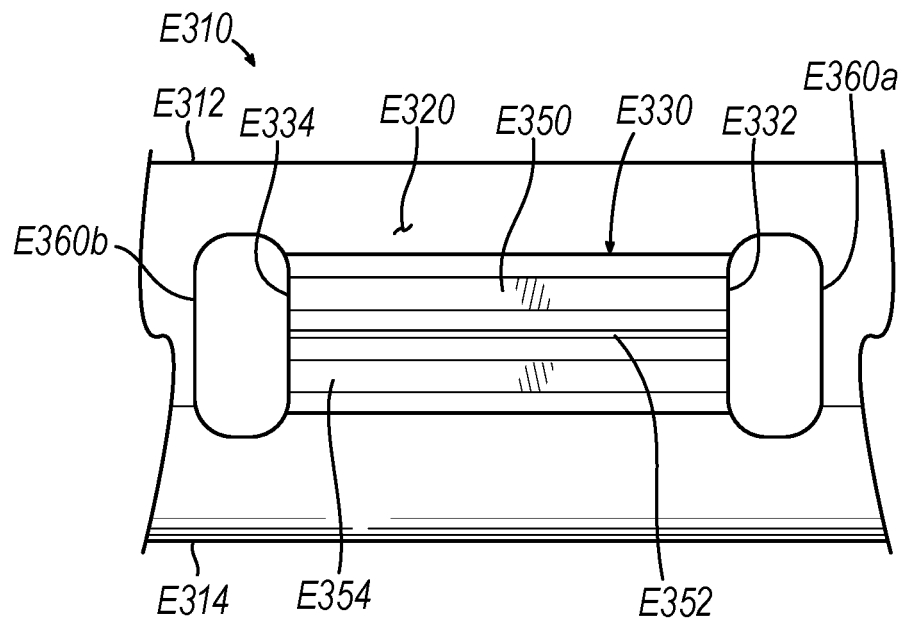
FIG. 10 depicts a partial side elevational view of another example of a lower pan of a staple cartridge for use with the end effector of FIG. 2 and having a retention tab extending laterally outwardly from a sidewall of the lower pan, the retention tab being longitudinally flanked by proximal and distal elongate relief slots.

C. Example of Cartridge Pan with Retention Tab Longitudinally Flanked by Elongate Relief Slots FIG. 10 shows a portion of another example of a lower pan (E310) that may be readily incorporated into staple cartridge (70) in place of lower pan (76). Lower pan (E310) may be similar to lower pan (E110) described above, except as otherwise described below. In this regard, lower pan (E310) may be configured to be coupled to an underside of cartridge body (72) such that sled (82) and staple drivers (84) may be movably captured between cartridge body (72) and pan (E310). Pan (E310) of the present example includes a laterally-opposed pair of sidewalls (E312) (one shown) coupled to each other by a bottom wall (E314), such that sidewalls (E312) and bottom wall (E314) collectively define a trough (not shown) similar to trough (E116) that is sized and configured to securely receive a cartridge body (not shown), such as cartridge body (72). Each sidewall (E312) has a respective laterally inner side surface (not shown) similar to laterally inner side surfaces (E118), which may confront and/or frictionally engage a respective laterally outer side surface of cartridge body (72); and a respective laterally outer side surface (E320), which may confront and/or frictionally engage a respective laterally inner side surface (E102) of a channel (E100) of a cartridge jaw (not shown), such as cartridge jaw (42). While pan (E310) is shown and described for incorporation into cartridge (70) and as being used in conjunction with channel (E100), it will be appreciated that pan (E310) may be incorporated into any other suitable cartridge and/or may be used in conjunction with any other suitable channel.

In the example shown, pan (E310) also includes a retention tab (E330) extending laterally outwardly from each sidewall (E312). Each retention tab (E330) extends longitudinally between a respective proximal end (E332) and a respective distal end (E334), and includes laterally inner surfaces that collectively define a respective open-ended recess (not shown) similar to recess (E146) for permitting laterally-inward flexing of the respective retention tab (E330) into the respective recess. Each retention tab (E330) also includes an upper, laterally outer surface (E350) extending downwardly and laterally outwardly from an upper region of the laterally outer side surface (E320) of the respective sidewall (E312), a middle, laterally outer surface (E352) extending vertically downwardly from the respective upper, laterally outer surface (E350), and a lower, laterally outer surface (E354) extending downwardly and laterally inwardly from the respective middle, laterally outer surface (E352) to a lower region of the laterally outer side surface (E320) of the respective sidewall (E312).

In the example shown, pan (E310) also includes a pair of relief slots (E360a, E360b) extending laterally through each sidewall (E312) from the inner side surface thereof to the laterally outer side surface (E320) thereof. Each relief slot (E360a, E360b) is positioned adjacent to a corresponding retention tab (E330) to impart the corresponding retention tab (E330) with a reduced stiffness and/or increased resilience. In this regard, each pair of relief slots (E360a, E360b) includes a proximal relief slot (E360a) positioned adjacent to and/or extending along the proximal end (E332) of the corresponding retention tab (E330), and a distal relief slot (E360b) positioned adjacent to and/or extending along the distal end (E334) of the corresponding retention tab (E330), such that each retention tab (E330) is longitudinally flanked by a corresponding pair of relief slots (E360a, E360b). Each relief slot (E360a, E360b) is substantially elongate. Due to the recess of each retention tab (E330) being open-ended as described above, relief slots (E360a, E360b) may each open directly into the respective recess.

In some versions, retention tabs (E330) and relief slots (E360a, E360b) may be arranged on sidewalls (E312) in laterally-opposed pairs with each laterally-opposed pair of retention tabs (E330) and each laterally-opposed pair of relief slots (E360a, E360b) being symmetrical relative to a longitudinal axis of pan (E310). In other versions, retention tabs (E330) and/or relief slots (E360a, E360b) may alternatively be configured substantially differently on each sidewall (E312) of pan (E310) so as to be asymmetrical relative to the longitudinal axis of pan (E310). For example, the retention tab (E330) and relief slots (E360a, E360b) on one sidewall (E312) may be offset in the vertical direction and/or offset in the longitudinal direction from the retention tab (E330) and relief slots (E360a, E360b) on the other sidewall (E312). In addition, or alternatively, the retention tab (E330) and relief slots (E360a, E360b) on one sidewall (E312) may be sized and/or shaped substantially differently from the retention tab (E330) and relief slots (E360a, E360b) on the other sidewall (E312), such as by being sized and/or shaped in accordance with any of the other teachings provided herein.

Figure 11:
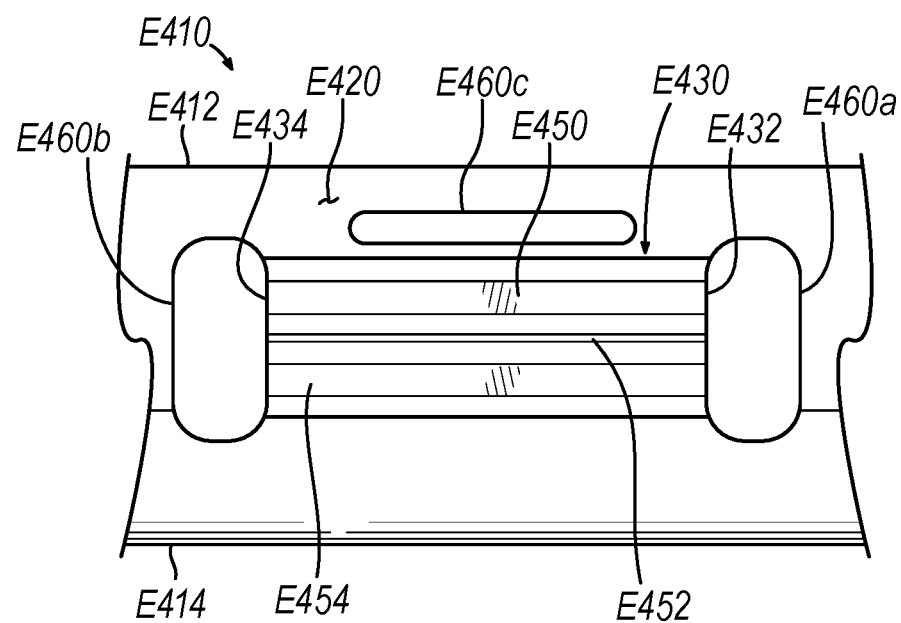
FIG. 11 depicts a partial side elevational view of another example of a lower pan of a staple cartridge for use with the end effector of FIG. 2 and having a retention tab extending laterally outwardly from a sidewall of the lower pan, the retention tab being partially surrounded by proximal, distal, and upper elongate relief slots.

D. Example of Cartridge Pan with Retention Tab Partially Surrounded by Proximal, Distal, and Upper Elongate Relief Slots FIG. 11 shows a portion of another example of a lower pan (E410) that may be readily incorporated into staple cartridge (70) in place of lower pan (76). Lower pan (E410) may be similar to lower pan (E110) described above, except as otherwise described below. In this regard, lower pan (E410) may be configured to be coupled to an underside of cartridge body (72) such that sled (82) and staple drivers (84) may be movably captured between cartridge body (72) and pan (E410). Pan (E410) of the present example includes a laterally-opposed pair of sidewalls (E412) (one shown) coupled to each other by a bottom wall (E414), such that sidewalls (E412) and bottom wall (E414) collectively define a trough (not shown) similar to trough (E116) that is sized and configured to securely receive a cartridge body (not shown), such as cartridge body (72). Each sidewall (E412) has a respective laterally inner side surface (not shown) similar to laterally inner side surfaces (E118), which may confront and/or frictionally engage a respective laterally outer side surface of cartridge body (72); and a respective laterally outer side surface (E420), which may confront and/or frictionally engage a respective laterally inner side surface (E102) of a channel (E100) of a cartridge jaw (not shown), such as cartridge jaw (42). While pan (E410) is shown and described for incorporation into cartridge (70) and as being used in conjunction with channel (E100), it will be appreciated that pan (E410) may be incorporated into any other suitable cartridge and/or may be used in conjunction with any other suitable channel.

In the example shown, pan (E410) also includes a retention tab (E430) extending laterally outwardly from each sidewall (E412). Each retention tab (E430) extends longitudinally between a respective proximal end (E432) and a respective distal end (E434), and includes laterally inner surfaces that collectively define a respective open-ended recess (not shown) similar to recess (E146) for permitting laterally-inward flexing of the respective retention tab (E430) into the respective recess. Each retention tab (E430) also includes an upper, laterally outer surface (E450) extending downwardly and laterally outwardly from an upper region of the laterally outer side surface (E420) of the respective sidewall (E412), a middle, laterally outer surface (E452) extending vertically downwardly from the respective upper, laterally outer surface (E450), and a lower, laterally outer surface (E454) extending downwardly and laterally inwardly from the respective middle, laterally outer surface (E452) to a lower region of the laterally outer side surface (E420) of the respective sidewall (E412).

In the example shown, pan (E410) also includes a plurality of relief slots (E460a, E460b, E460c) extending laterally through each sidewall (E412) from the inner side surface thereof to the laterally outer side surface (E420) thereof. Each relief slot (E460a, E460b, E460c) is positioned adjacent to a corresponding retention tab (E430) to impart the corresponding retention tab (E430) with a reduced stiffness and/or increased resilience. In this regard, each plurality of relief slots (E460a, E460b, E460c) includes a proximal relief slot (E460a) positioned adjacent to and/or extending along the proximal end (E432) of the corresponding retention tab (E430), and a distal relief slot (E460b) positioned adjacent to and/or extending along the distal end (E434) of the corresponding retention tab (E430), such that each retention tab (E430) is longitudinally flanked by a corresponding pair of proximal and distal relief slots (E460a, E460b); and further includes an upper intermediate relief slot (E460c) positioned adjacent to and/or extending at least partially along an upper edge of the corresponding retention tab (E430) (e.g., defined by an interface between the respective upper, laterally outer surface (E450) and the laterally outer side surface (E420) of the respective sidewall (E412)). Each relief slot (E460a, E460b, E460c) is substantially elongate. Due to the recess of each retention tab (E430) being open-ended as described above, proximal and distal relief slots (E460a, E460b) may each open directly into the respective recess.

As shown, each upper intermediate relief slot (E460c) is substantially centered in the longitudinal direction along the upper edge of the corresponding retention tab (E430) and extends along a middle portion thereof. In some other versions, each upper intermediate relief slot (E460c) may extend along only a proximal or distal portion of the upper edge of the corresponding retention tab (E430). In still other versions, each upper intermediate relief slot (E460c) may extend along the entire upper edge of the corresponding retention tab (E430). While intermediate relief slot (E460c) of the present example is positioned adjacent to and/or along an upper edge of the corresponding retention tab (E430), intermediate relief slot (E460c) may alternatively be positioned adjacent to and/or along a lower edge of the corresponding retention tab (E430) (e.g., defined by an interface between the respective lower, laterally outer surface (E454) and the laterally outer side surface (E420) of the respective sidewall (E412)).

In some versions, retention tabs (E430) and relief slots (E460a, E460b, E460c) may be arranged on sidewalls (E412) in laterally-opposed pairs with each laterally-opposed pair of retention tabs (E430) and each laterally-opposed pair of relief slots (E460a, E460b, E460c) being symmetrical relative to a longitudinal axis of pan (E410). In other versions, retention tabs (E430) and/or relief slots (E460a, E460b, E460c) may alternatively be configured substantially differently on each sidewall (E412) of pan (E410) so as to be asymmetrical relative to the longitudinal axis of pan (E410). For example, the retention tab (E430) and relief slots (E460a, E460b, E460c) on one sidewall (E412) may be offset in the vertical direction and/or offset in the longitudinal direction from the retention tab (E430) and relief slots (E460a, E460b, E460c) on the other sidewall (E412). In addition, or alternatively, the retention tab (E430) and relief slots (E460a, E460b, E460c) on one sidewall (E412) may be sized and/or shaped substantially differently from the retention tab (E430) and relief slots (E460a, E460b, E460c) on the other sidewall (E412), such as by being sized and/or shaped in accordance with any of the other teachings provided herein.

Figure 12:
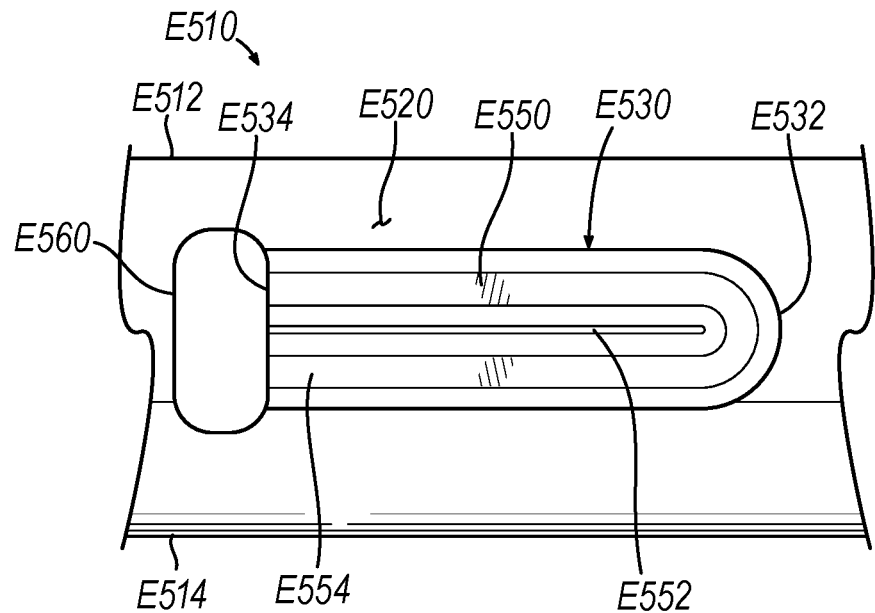
FIG. 12 depicts a partial side elevational view of another example of a lower pan of a staple cartridge for use with the end effector of FIG. 2 and having a retention tab extending laterally outwardly from a sidewall of the lower pan, the lower pan further having a distal elongate relief slot adjacent a distal end of the retention tab.

E. Example of Cartridge Pan with Elongate Relief Slot at One End of Retention Tab FIG. 12 shows a portion of another example of a lower pan (E510) that may be readily incorporated into staple cartridge (70) in place of lower pan (76). Lower pan (E510) may be similar to lower pan (E110) described above, except as otherwise described below. In this regard, lower pan (E510) may be configured to be coupled to an underside of cartridge body (72) such that sled (82) and staple drivers (84) may be movably captured between cartridge body (72) and pan (E510). Pan (E510) of the present example includes a laterally-opposed pair of sidewalls (E512) (one shown) coupled to each other by a bottom wall (E514), such that sidewalls (E512) and bottom wall (E514) collectively define a trough (not shown) similar to trough (E116) that is sized and configured to securely receive a cartridge body (not shown), such as cartridge body (72). Each sidewall (E512) has a respective laterally inner side surface (not shown) similar to laterally inner side surfaces (E118), which may confront and/or frictionally engage a respective laterally outer side surface of cartridge body (72); and a respective laterally outer side surface (E520), which may confront and/or frictionally engage a respective laterally inner side surface (E102) of a channel (E100) of a cartridge jaw (not shown), such as cartridge jaw (42). While pan (E510) is shown and described for incorporation into cartridge (70) and as being used in conjunction with channel (E100), it will be appreciated that pan (E510) may be incorporated into any other suitable cartridge and/or may be used in conjunction with any other suitable channel.

In the example shown, pan (E510) also includes a retention tab (E530) extending laterally outwardly from each sidewall (E512). Each retention tab (E530) extends longitudinally between a respective proximal end (E532) and a respective distal end (E534), and includes laterally inner surfaces that collectively define a respective distally open-ended recess (not shown) similar to recess (E146) for permitting laterally-inward flexing of the respective retention tab (E530) into the respective recess. In the example shown, the proximal end of each recess is closed by the proximal end (E532) of the respective retention tab (E530). In other versions, each recess may be proximally open-ended and the distal end of each recess may be closed by the distal end (E534) of the respective retention tab (E530), or each recess may be open-ended both proximally and distally as described above in connection with recess (E146). Each retention tab (E530) also includes an upper, laterally outer surface (E550) extending downwardly and laterally outwardly from an upper region of the laterally outer side surface (E520) of the respective sidewall (E512), a middle, laterally outer surface (E552) extending vertically downwardly from the respective upper, laterally outer surface (E550), and a lower, laterally outer surface (E554) extending downwardly and laterally inwardly from the respective middle, laterally outer surface (E552) to a lower region of the laterally outer side surface (E520) of the respective sidewall (E512).

In the example shown, pan (E510) also includes a relief slot (E560) extending laterally through each sidewall (E512) from the inner side surface thereof to the laterally outer side surface (E520) thereof. Each relief slot (E560) is positioned adjacent to a corresponding retention tab (E530) to impart the corresponding retention tab (E530) with a reduced stiffness and/or increased resilience. In this regard, each relief slot (E560) is positioned adjacent to and/or extends along the distal end (E534) of the corresponding retention tab (E530). Each relief slot (E560) is substantially elongate. Due to the recess of each retention tab (E530) being distally open-ended as described above, relief slots (E560) may each open directly into the respective recess.

While each relief slot (E560) of the present example is positioned adjacent to and/or extends along the distal end (E534) of the corresponding retention tab (E530), each relief slot (E560) may alternatively be positioned adjacent to and/or extend along the proximal end (E532) of the corresponding retention tab (E530).

In some versions, retention tabs (E530) and relief slots (E560) may be arranged on sidewalls (E512) in laterally-opposed pairs with each laterally-opposed pair of retention tabs (E530) and each laterally-opposed pair of relief slots (E560) being symmetrical relative to a longitudinal axis of pan (E510). In other versions, retention tabs (E530) and/or relief slots (E560) may alternatively be configured substantially differently on each sidewall (E512) of pan (E510) so as to be asymmetrical relative to the longitudinal axis of pan (E510). For example, the retention tab (E530) and relief slots (E560) on one sidewall (E512) may be offset in the vertical direction and/or offset in the longitudinal direction from the retention tab (E530) and relief slots (E560) on the other sidewall (E512). In addition, or alternatively, the retention tab (E530) and relief slots (E560) on one sidewall (E512) may be sized and/or shaped substantially differently from the retention tab (E530) and relief slots (E560) on the other sidewall (E512), such as by being sized and/or shaped in accordance with any of the other teachings provided herein.

Figure 13:
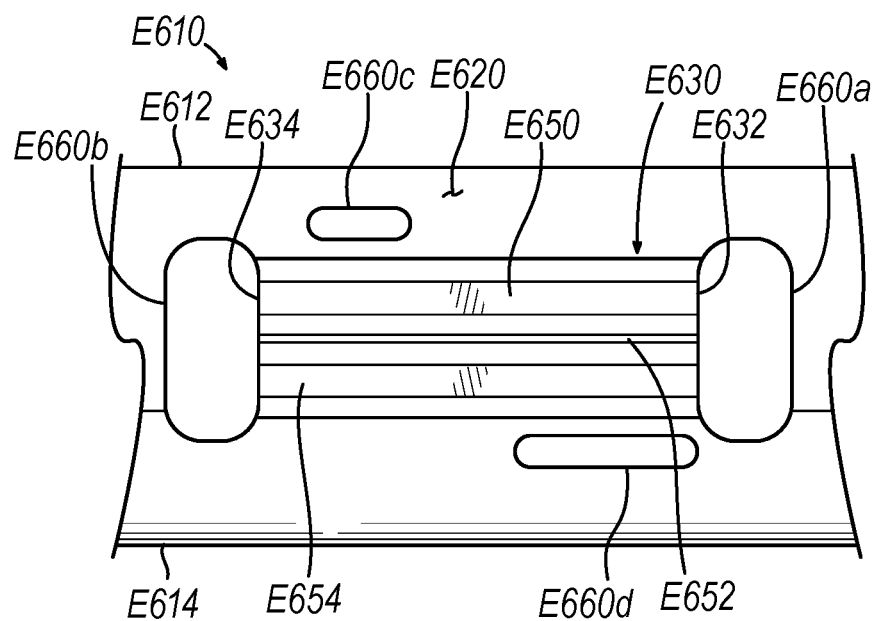
FIG. 13 depicts a partial side elevational view of another example of a lower pan of a staple cartridge for use with the end effector of FIG. 2 and having a retention tab extending laterally outwardly from a sidewall of the lower pan, the retention tab being partially surrounded by proximal, distal, upper, and lower elongate relief slots.

F. Example of Cartridge Pan with Retention Tab Partially Surrounded by Proximal, Distal, Upper, and Lower Elongate Relief Slots FIG. 13 shows a portion of another example of a lower pan (E610) that may be readily incorporated into staple cartridge (70) in place of lower pan (76). Lower pan (E610) may be similar to lower pan (E110) described above, except as otherwise described below. In this regard, lower pan (E610) may be configured to be coupled to an underside of cartridge body (72) such that sled (82) and staple drivers (84) may be movably captured between cartridge body (72) and pan (E610). Pan (E610) of the present example includes a laterally-opposed pair of sidewalls (E612) (one shown) coupled to each other by a bottom wall (E614), such that sidewalls (E612) and bottom wall (E614) collectively define a trough (not shown) similar to trough (E116) that is sized and configured to securely receive a cartridge body (not shown), such as cartridge body (72). Each sidewall (E612) has a respective laterally inner side surface (not shown) similar to laterally inner side surfaces (E118), which may confront and/or frictionally engage a respective laterally outer side surface of cartridge body (72); and a respective laterally outer side surface (E620), which may confront and/or frictionally engage a respective laterally inner side surface (E102) of a channel (E100) of a cartridge jaw (not shown), such as cartridge jaw (42). While pan (E610) is shown and described for incorporation into cartridge (70) and as being used in conjunction with channel (E100), it will be appreciated that pan (E610) may be incorporated into any other suitable cartridge and/or may be used in conjunction with any other suitable channel.

In the example shown, pan (E610) also includes a retention tab (E630) extending laterally outwardly from each sidewall (E612). Each retention tab (E630) extends longitudinally between a respective proximal end (E632) and a respective distal end (E634), and includes laterally inner surfaces that collectively define a respective open-ended recess (not shown) similar to recess (E146) for permitting laterally-inward flexing of the respective retention tab (E630) into the respective recess. Each retention tab (E630) also includes an upper, laterally outer surface (E650) extending downwardly and laterally outwardly from an upper region of the laterally outer side surface (E620) of the respective sidewall (E612), a middle, laterally outer surface (E652) extending vertically downwardly from the respective upper, laterally outer surface (E650), and a lower, laterally outer surface (E654) extending downwardly and laterally inwardly from the respective middle, laterally outer surface (E652) to a lower region of the laterally outer side surface (E620) of the respective sidewall (E612).

In the example shown, pan (E610) also includes a plurality of relief slots (E660a, E660b, E660c, E660d) extending laterally through each sidewall (E612) from the inner side surface thereof to the laterally outer side surface (E620) thereof. Each relief slot (E660a, E660b, E660c, E660d) is positioned adjacent to a corresponding retention tab (E630) to impart the corresponding retention tab (E630) with a reduced stiffness and/or increased resilience. In this regard, each plurality of relief slots (E660a, E660b, E660c, E660d) includes a proximal relief slot (E660a) positioned adjacent to and/or extending along the proximal end (E632) of the corresponding retention tab (E630), and a distal relief slot (E660b) positioned adjacent to and/or extending along the distal end (E634) of the corresponding retention tab (E630), such that each retention tab (E630) is longitudinally flanked by a corresponding pair of proximal and distal relief slots (E660a, E660b); and further includes an upper intermediate relief slot (E660c) positioned adjacent to and/or extending at least partially along an upper edge of the corresponding retention tab (E630) (e.g., defined by an interface between the respective upper, laterally outer surface (E650) and the laterally outer side surface (E620) of the respective sidewall (E612)), and a lower intermediate relief slot (E660d) positioned adjacent to and/or extending at least partially along a lower edge of the corresponding retention tab (E630) (e.g., defined by an interface between the respective lower, laterally outer surface (E654) and the laterally outer side surface (E620) of the respective sidewall (E612)). Each relief slot (E660a, E660b, E660c, E660d) is substantially elongate. Due to the recess of each retention tab (E630) being open-ended as described above, proximal and distal relief slots (E660a, E660b) may each open directly into the respective recess.

As shown, each upper intermediate relief slot (E660c) extends along only a distal portion of the upper edge of the corresponding retention tab (E630) while each lower intermediate relief slot (E660d) extends along only a proximal portion of the lower edge of the corresponding retention tab (E630), such that each upper intermediate relief slot (E660c) is disposed at a substantially different position in the longitudinal direction than the corresponding lower intermediate relief slot (E660d). In some other versions, each upper intermediate relief slot (E660c) may extend along only a proximal portion of the upper edge of the corresponding retention tab (E630) and/or each lower intermediate relief slot (E660d) may extend along only a proximal portion of the lower edge of the corresponding retention tab (E630). In still other versions, each upper intermediate relief slot (E660c) may be substantially centered in the longitudinal direction along the upper edge of the corresponding retention tab (E630) and/or each lower intermediate relief slot (E660d) may be substantially centered in the longitudinal direction along the lower edge of the corresponding retention tab (E630), such as in a manner similar to that described above in connection with intermediate relief slot (E460c). In addition, or alternatively, each upper intermediate relief slot (E660c) may extend along the entire upper edge of the corresponding retention tab (E630) and/or each lower intermediate relief slot (E660d) may extend along the entire lower edge of the corresponding retention tab (E630).

In some versions, retention tabs (E630) and relief slots (E660a, E660b, E660c, E660d) may be arranged on sidewalls (E612) in laterally-opposed pairs with each laterally-opposed pair of retention tabs (E630) and each laterally-opposed pair of relief slots (E660a, E660b, E660c, E660d) being symmetrical relative to a longitudinal axis of pan (E610). In other versions, retention tabs (E630) and/or relief slots (E660a, E660b, E660c, E660d) may alternatively be configured substantially differently on each sidewall (E612) of pan (E610) so as to be asymmetrical relative to the longitudinal axis of pan (E610). For example, the retention tab (E630) and relief slots (E660a, E660b, E660c, E660d) on one sidewall (E612) may be offset in the vertical direction and/or offset in the longitudinal direction from the retention tab (E630) and relief slots (E660a, E660b, E660c, E660d) on the other sidewall (E612). In addition, or alternatively, the retention tab (E630) and relief slots (E660a, E660b, E660c, E660d) on one sidewall (E612) may be sized and/or shaped substantially differently from the retention tab (E630) and relief slots (E660a, E660b, E660c, E660d) on the other sidewall (E612), such as by being sized and/or shaped in accordance with any of the other teachings provided herein.

Figure 14:
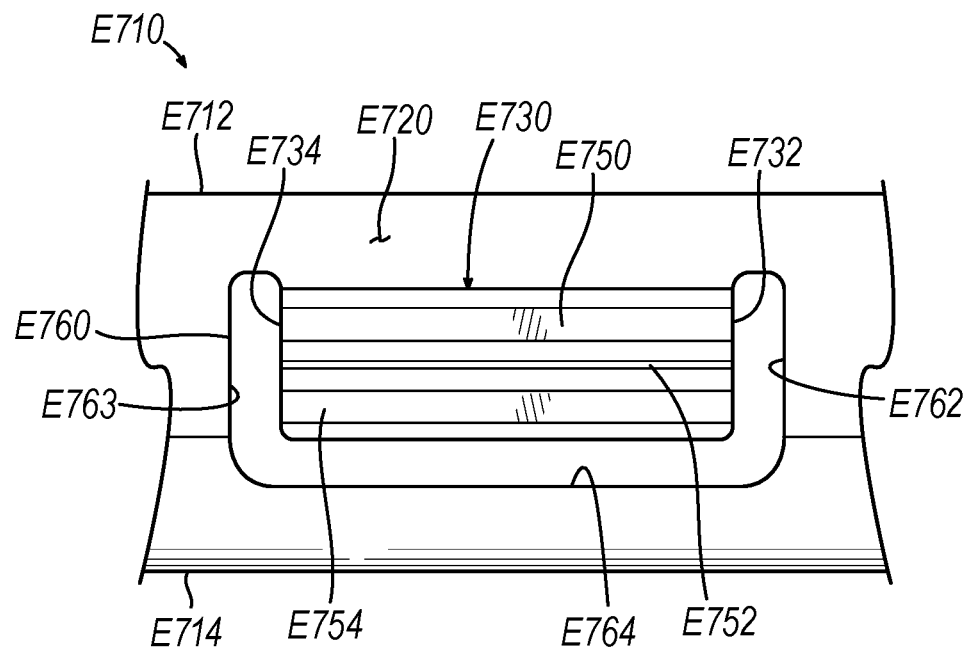
FIG. 14 depicts a partial side elevational view of another example of a lower pan of a staple cartridge for use with the end effector of FIG. 2 and having a retention tab extending laterally outwardly from a sidewall of the lower pan, the retention tab being partially surrounded by a U-shaped relief slot.

G. Example of Cartridge Pan with Retention Tab Partially Surrounded by U-Shaped Relief Slot FIG. 14 shows a portion of another example of a lower pan (E710) that may be readily incorporated into staple cartridge (70) in place of lower pan (76). Lower pan (E710) may be similar to lower pan (E110) described above, except as otherwise described below. In this regard, lower pan (E710) may be configured to be coupled to an underside of cartridge body (72) such that sled (82) and staple drivers (84) may be movably captured between cartridge body (72) and pan (E710). Pan (E710) of the present example includes a laterally-opposed pair of sidewalls (E712) (one shown) coupled to each other by a bottom wall (E714), such that sidewalls (E712) and bottom wall (E714) collectively define a trough (not shown) similar to trough (E116) that is sized and configured to securely receive a cartridge body (not shown), such as cartridge body (72). Each sidewall (E712) has a respective laterally inner side surface (not shown) similar to laterally inner side surfaces (E118), which may confront and/or frictionally engage a respective laterally outer side surface of cartridge body (72); and a respective laterally outer side surface (E720), which may confront and/or frictionally engage a respective laterally inner side surface (E102) of a channel (E100) of a cartridge jaw (not shown), such as cartridge jaw (42). While pan (E710) is shown and described for incorporation into cartridge (70) and as being used in conjunction with channel (E100), it will be appreciated that pan (E710) may be incorporated into any other suitable cartridge and/or may be used in conjunction with any other suitable channel.

In the example shown, pan (E710) also includes a retention tab (E730) extending laterally outwardly from each sidewall (E712). Each retention tab (E730) extends longitudinally between a respective proximal end (E732) and a respective distal end (E734), and includes laterally inner surfaces that collectively define a respective open-ended recess (not shown) similar to recess (E146) for permitting laterally-inward flexing of the respective retention tab (E730) into the respective recess. Each retention tab (E730) also includes an upper, laterally outer surface (E750) extending downwardly and laterally outwardly from an upper region of the laterally outer side surface (E720) of the respective sidewall (E712), a middle, laterally outer surface (E752) extending vertically downwardly from the respective upper, laterally outer surface (E750), and a lower, laterally outer surface (E754) extending downwardly and laterally inwardly from the respective middle, laterally outer surface (E752) toward a lower region of the laterally outer side surface (E720) of the respective sidewall (E712).

In the example shown, pan (E710) also includes a relief slot (E760) extending laterally through each sidewall (E712) from the inner side surface thereof to the laterally outer side surface (E720) thereof. Each relief slot (E760) is positioned adjacent to a corresponding retention tab (E730) to impart the corresponding retention tab (E730) with a reduced stiffness and/or increased resilience. In this regard, each relief slot (E760) includes a proximal vertical slot portion (E762) positioned adjacent to the proximal end (E732) of the corresponding retention tab (E730), a distal vertical slot portion (E763) positioned adjacent to the distal end (E734) of the corresponding retention tab (E730), and a horizontal slot portion (E764) extending longitudinally between the lower ends of the respective vertical slot portions (E762, E763), such that each relief slot (E760) is substantially U-shaped. More particularly, the proximal vertical slot portion (E762) of each relief slot (E760) extends along the proximal end (E732) of the corresponding retention tab (E730), and the distal vertical slot portion (E763) of each relief slot (E760) extends along the distal end (E734) of the corresponding retention tab (E730), such that each retention tab (E730) is longitudinally flanked by the vertical slot portions (E762, E763) of a corresponding relief slot (E760); and the horizontal slot portion (E764) of each relief slot (E760) extends along the entire lower edge of the corresponding retention tab (E730) to thereby space apart the lower edge of the corresponding retention tab (E730) from the lower region of the laterally outer side surface (E720) of the respective sidewall (E712), such that each retention tab (E730) may be cantilevered from the upper region of the laterally outer side surface (E720) of the respective sidewall (E712). It will be appreciated that such a cantilevered configuration may further reduce the stiffness and/or increase the resilience of each retention tab (E730). Due to the recess of each retention tab (E730) being open-ended as described above, vertical slot portions (E762, E763) of each relief slot (E760) may open directly into the respective recess.

While horizontal slot portion (E764) of the present example is positioned adjacent to and/or along a lower edge of the corresponding retention tab (E730), horizontal slot portion (E764) may alternatively be positioned adjacent to and/or along an upper edge of the corresponding retention tab (E730). For example, the horizontal slot portion (E764) of each relief slot (E760) may extend along the entire upper edge of the corresponding retention tab (E730) to thereby space apart the upper edge of the corresponding retention tab (E730) from the upper region of the laterally outer side surface (E720) of the respective sidewall (E712), such that each retention tab (E730) may be cantilevered from the lower region of the laterally outer side surface (E720) of the respective sidewall (E712).

In some versions, retention tabs (E730) and relief slots (E760) may be arranged on sidewalls (E712) in laterally-opposed pairs with each laterally-opposed pair of retention tabs (E730) and each laterally-opposed pair of relief slots (E760) being symmetrical relative to a longitudinal axis of pan (E710). In other versions, retention tabs (E730) and/or relief slots (E760) may alternatively be configured substantially differently on each sidewall (E712) of pan (E710) so as to be asymmetrical relative to the longitudinal axis of pan (E710). For example, the retention tab (E730) and relief slots (E760) on one sidewall (E712) may be offset in the vertical direction and/or offset in the longitudinal direction from the retention tab (E730) and relief slots (E760) on the other sidewall (E712). In addition, or alternatively, the retention tab (E730) and relief slots (E760) on one sidewall (E712) may be sized and/or shaped substantially differently from the retention tab (E730) and relief slots (E760) on the other sidewall (E712), such as by being sized and/or shaped in accordance with any of the other teachings provided herein.

Figure 15:
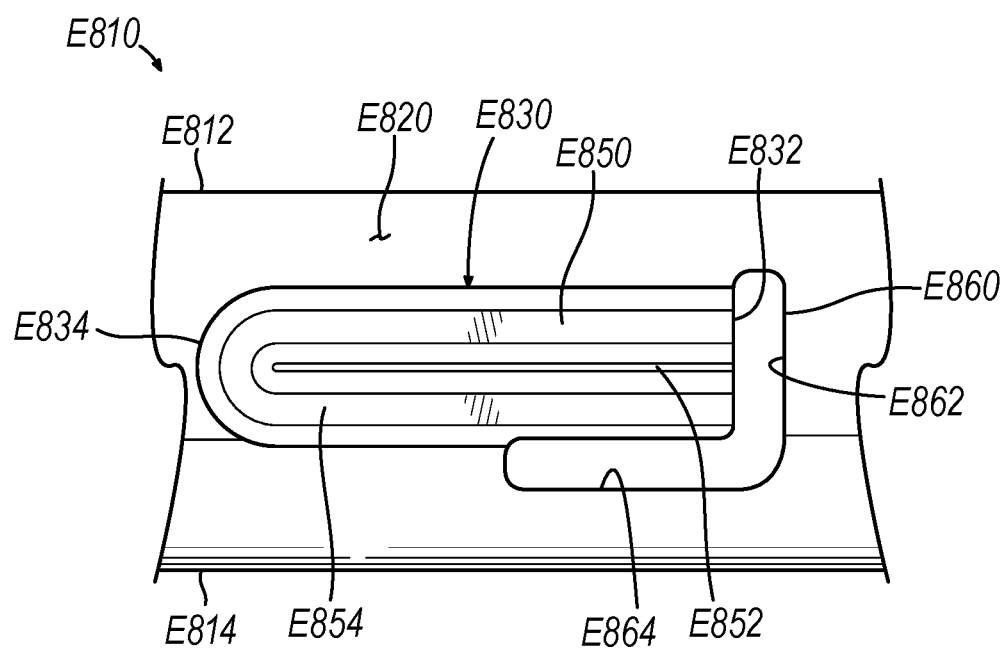
FIG. 15 depicts a partial side elevational view of another example of a lower pan of a staple cartridge for use with the end effector of FIG. 2 and having a retention tab extending laterally outwardly from a sidewall of the lower pan, the lower pan further having a proximal L-shaped relief slot adjacent a proximal end of the retention tab.

H. Example of Cartridge Pan with L-Shaped Relief Slot at One End of Retention Tab FIG. 15 shows a portion of another example of a lower pan (E810) that may be readily incorporated into staple cartridge (70) in place of lower pan (76). Lower pan (E810) may be similar to lower pan (E110) described above, except as otherwise described below. In this regard, lower pan (E810) may be configured to be coupled to an underside of cartridge body (72) such that sled (82) and staple drivers

(84) may be movably captured between cartridge body (72) and pan (E810). Pan (E810) of the present example includes a laterally-opposed pair of sidewalls (E812) (one shown) coupled to each other by a bottom wall (E814), such that sidewalls (E812) and bottom wall (E814) collectively define a trough (not shown) similar to trough (E116) that is sized and configured to securely receive a cartridge body (not shown), such as cartridge body (72). Each sidewall (E812) has a respective laterally inner side surface (not shown) similar to laterally inner side surfaces (E118), which may confront and/or frictionally engage a respective laterally outer side surface of cartridge body (72); and a respective laterally outer side surface (E820), which may confront and/or frictionally engage a respective laterally inner side surface (E102) of a channel (E100) of a cartridge jaw (not shown), such as cartridge jaw (42). While pan (E810) is shown and described for incorporation into cartridge (70) and as being used in conjunction with channel (E100), it will be appreciated that pan (E810) may be incorporated into any other suitable cartridge and/or may be used in conjunction with any other suitable channel.

In the example shown, pan (E810) also includes a retention tab (E830) extending laterally outwardly from each sidewall (E812). Each retention tab (E830) extends longitudinally between a respective proximal end (E832) and a respective distal end (E834), and includes laterally inner surfaces that collectively define a respective proximally open-ended recess (not shown) similar to recess (E146) for permitting laterally-inward flexing of the respective retention tab (E830) into the respective recess. In the example shown, the distal end of each recess is closed by the distal end (E834) of the respective retention tab (E830). In other versions, each recess may be distally open-ended and the proximal end of each recess may be closed by the proximal end (E834) of the respective retention tab (E830), or each recess may be open-ended both proximally and distally as described above in connection with recess (E146). Each retention tab (E830) also includes an upper, laterally outer surface (E850) extending downwardly and laterally outwardly from an upper region of the laterally outer side surface (E820) of the respective sidewall (E812), a middle, laterally outer surface (E852) extending vertically downwardly from the respective upper, laterally outer surface (E850), and a lower, laterally outer surface (E854) extending downwardly and laterally inwardly from the respective middle, laterally outer surface (E852) to a lower region of the laterally outer side surface (E820) of the respective sidewall (E812).

In the example shown, pan (E810) also includes a relief slot (E860) extending laterally through each sidewall (E812) from the inner side surface thereof to the laterally outer side surface (E820) thereof. Each relief slot (E860) is positioned adjacent to a corresponding retention tab (E830) to impart the corresponding retention tab (E830) with a reduced stiffness and/or increased resilience. In this regard, each relief slot (E860) includes a vertical slot portion (E862) positioned adjacent to the proximal end (E832) of the corresponding retention tab (E830), and a horizontal slot portion (E864) extending longitudinally from a lower end of the respective vertical slot portion (E862), such that each relief slot (E860) is substantially L-shaped. More particularly, the vertical slot portion (E862) of each relief slot (E860) extends along the proximal end (E832) of the corresponding retention tab (E830), and the horizontal slot portion (E864) of each relief slot (E860) extends distally from the lower end of the respective vertical slot portion (E862) along a proximal portion of a lower edge of the corresponding retention tab (E830). Due to the recess of each retention tab (E830) being proximally open-ended as described above, vertical slot portion (E862) of each relief slot (E860) may open directly into the respective recess.

While horizontal slot portion (E864) of the present example is positioned adjacent to and/or along a lower edge of the corresponding retention tab (E830), horizontal slot portion (E864) may alternatively be positioned adjacent to and/or along an upper edge of the corresponding retention tab (E830). For example, the horizontal slot portion (E864) of each relief slot (E860) may extend distally from an upper end of the respective vertical slot portion (E862) along a proximal portion of an upper edge of the corresponding retention tab (E830). While vertical slot portion (E862) of the present example is positioned adjacent to and/or along the proximal end (E832) of the corresponding retention tab (E830), vertical slot portion (E862) may alternatively be positioned adjacent to and/or along the distal end (E834) of the corresponding retention tab (E830). In such cases, horizontal slot portion (E864) may extend proximally from an upper or lower end of the respective vertical slot portion (E862) along a distal portion of the upper or lower edge of the corresponding retention tab (E830), for example.

In some versions, retention tabs (E830) and relief slots (E860) may be arranged on sidewalls (E812) in laterally-opposed pairs with each laterally-opposed pair of retention tabs (E830) and each laterally-opposed pair of relief slots (E860) being symmetrical relative to a longitudinal axis of pan (E810). In other versions, retention tabs (E830) and/or relief slots (E860) may alternatively be configured substantially differently on each sidewall (E812) of pan (E810) so as to be asymmetrical relative to the longitudinal axis of pan (E810). For example, the retention tab (E830) and relief slots (E860) on one sidewall (E812) may be offset in the vertical direction and/or offset in the longitudinal direction from the retention tab (E830) and relief slots (E860) on the other sidewall (E812). In addition, or alternatively, the retention tab (E830) and relief slots (E860) on one sidewall (E812) may be sized and/or shaped substantially differently from the retention tab (E830) and relief slots (E860) on the other sidewall (E812), such as by being sized and/or shaped in accordance with any of the other teachings provided herein.

Figure 16:
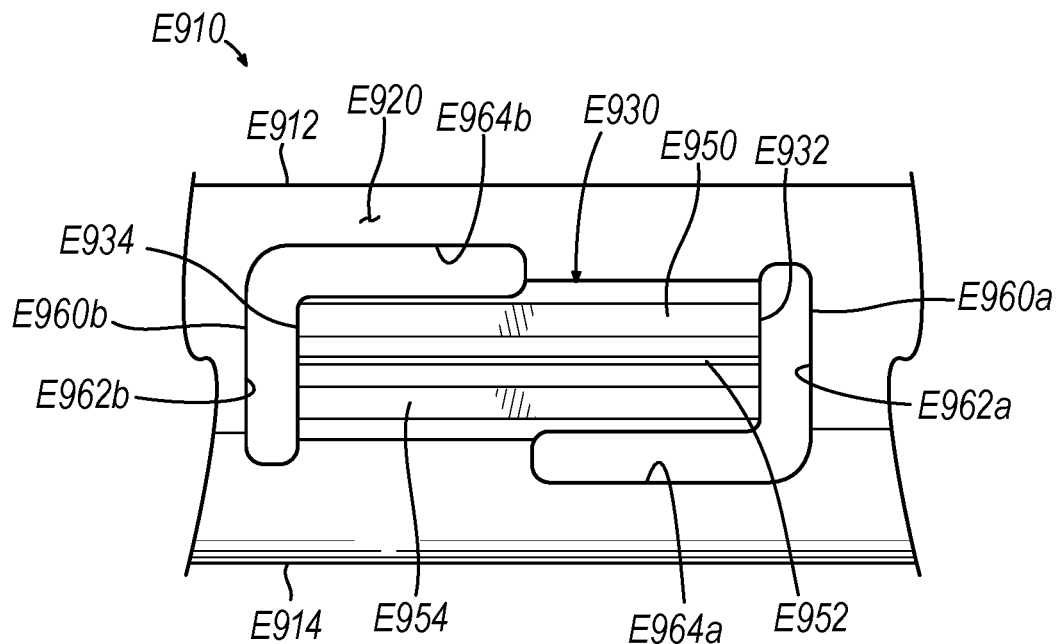
FIG. 16 depicts a partial side elevational view of another example of a lower pan of a staple cartridge for use with the end effector of FIG. 2 and having a retention tab extending laterally outwardly from a sidewall of the lower pan, the retention tab being partially surrounded by a pair of L-shaped relief slots.

I. Example of Cartridge Pan with Retention Tab Partially Surrounded by L-Shaped Relief Slots FIG. 16 shows a portion of another example of a lower pan (E910) that may be readily incorporated into staple cartridge (70) in place of lower pan (76). Lower pan (E910) may be similar to lower pan (E110) described above, except as otherwise described below. In this regard, lower pan (E910) may be configured to be coupled to an underside of cartridge body (72) such that sled (82) and staple drivers (84) may be movably captured between cartridge body (72) and pan (E910). Pan (E910) of the present example includes a laterally-opposed pair of sidewalls (E912) (one shown) coupled to each other by a bottom wall (E914), such that sidewalls (E912) and bottom wall (E914) collectively define a trough (not shown) similar to trough (E116) that is sized and configured to securely receive a cartridge body (not shown), such as cartridge body (72). Each sidewall (E912) has a respective laterally inner side surface (not shown) similar to laterally inner side surfaces (E118), which may confront and/or frictionally engage a respective laterally outer side surface of cartridge body (72); and a respective laterally outer side surface (E920), which may confront and/or frictionally engage a respective laterally inner side surface (E102) of a channel (E100) of a cartridge jaw (not shown), such as cartridge jaw (42). While pan (E910) is shown and described for incorporation into cartridge (70) and as being used in conjunction with channel (E100), it will be appreciated that pan (E910) may be incorporated into any other suitable cartridge and/or may be used in conjunction with any other suitable channel.

In the example shown, pan (E910) also includes a retention tab (E930) extending laterally outwardly from each sidewall (E912). Each retention tab (E930) extends longitudinally between a respective proximal end (E932) and a respective distal end (E934), and includes laterally inner surfaces that collectively define a respective open-ended recess (not shown) similar to recess (E146) for permitting laterally-inward flexing of the respective retention tab (E930) into the respective recess. Each retention tab (E930) also includes an upper, laterally outer surface (E950) extending downwardly and laterally outwardly from an upper region of the laterally outer side surface (E920) of the respective sidewall (E912), a middle, laterally outer surface (E952) extending vertically downwardly from the respective upper, laterally outer surface (E950), and a lower, laterally outer surface (E954) extending downwardly and laterally inwardly from the respective middle, laterally outer surface (E952) to a lower region of the laterally outer side surface (E920) of the respective sidewall (E912).

In the example shown, pan (E910) also includes a pair of relief slots (E960a, E960b) extending laterally through each sidewall (E912) from the inner side surface thereof to the laterally outer side surface (E920) thereof. Each relief slot (E960a, E960b) is positioned adjacent to a corresponding retention tab (E930) to impart the corresponding retention tab (E930) with a reduced stiffness and/or increased resilience. In this regard, each pair of relief slots (E960a, E960b) includes a proximal relief slot (E960a) positioned adjacent to the proximal end (E932) of the corresponding retention tab (E930), and a distal relief slot (E960b) positioned adjacent to the distal end (E934) of the corresponding retention tab (E930), such that each retention tab (E930) is longitudinally flanked by a corresponding pair of relief slots (E960a, E960b). Each relief slot (E960a, E960b) includes a respective vertical slot portion (E962a, E962b) extending along the respective end (E932, E934) of the corresponding retention tab (E930), and a respective horizontal slot portion (E964a, E964b) extending longitudinally from a respective end of the respective vertical slot portion (E962a, E962b), such that each relief slot (E960a, E960b) is substantially L-shaped. More particularly, the vertical slot portion (E962a) of each proximal relief slot (E960a) extends along the proximal end (E932) of the corresponding retention tab (E930), and the horizontal slot portion (E964a) of each proximal relief slot (E960a) extends distally from the lower end of the respective vertical slot portion (E962a) along a proximal portion of a lower edge of the corresponding retention tab (E930). Similarly, the vertical slot portion (E962b) of each distal relief slot (E960b) extends along the distal end (E934) of the corresponding retention tab (E930), and the horizontal slot portion (E964b) of each distal relief slot (E960b) extends proximally from the upper end of the respective vertical slot portion (E962b) along a distal portion of an upper edge of the corresponding retention tab (E930). Due to the recess of each retention tab (E930) being open-ended as described above, vertical slot portions (E962a, E962b) of proximal and distal relief slots (E960a, E960b) may open directly into the respective recess.

While horizontal slot portion (E964a) of the present example is positioned adjacent to and/or along a lower edge of the corresponding retention tab (E930), horizontal slot portion (E964a) may alternatively be positioned adjacent to and/or along an upper edge of the corresponding retention tab (E930). For example, the horizontal slot portion (E964a) of each proximal relief slot (E960a) may extend distally from an upper end of the respective vertical slot portion (E962a) along a proximal portion of an upper edge of the corresponding retention tab (E930). While horizontal slot portion (E964b) of the present example is positioned adjacent to and/or along an upper edge of the corresponding retention tab (E930), horizontal slot portion (E964b) may alternatively be positioned adjacent to and/or along a lower edge of the corresponding retention tab (E930). For example, the horizontal slot portion (E964b) of each distal relief slot (E960b) may extend proximally from a lower end of the respective vertical slot portion (E962b) along a distal portion of a lower edge of the corresponding retention tab (E930).

In some versions, retention tabs (E930) and relief slots (E960a, E960b) may be arranged on sidewalls (E912) in laterally-opposed pairs with each laterally-opposed pair of retention tabs (E930) and each laterally-opposed pair of relief slots (E960a, E960b) being symmetrical relative to a longitudinal axis of pan (E910). In other versions, retention tabs (E930) and/or relief slots (E960a, E960b) may alternatively be configured substantially differently on each sidewall (E912) of pan (E910) so as to be asymmetrical relative to the longitudinal axis of pan (E910). For example, the retention tab (E930) and relief slots (E960a, E960b) on one sidewall (E912) may be offset in the vertical direction and/or offset in the longitudinal direction from the retention tab (E930) and relief slots (E960a, E960b) on the other sidewall (E912). In addition, or alternatively, the retention tab (E930) and relief slots (E960a, E960b) on one sidewall (E912) may be sized and/or shaped substantially differently from the retention tab (E930) and relief slots (E960a, E960b) on the other sidewall (E912), such as by being sized and/or shaped in accordance with any of the other teachings provided herein.

Figure 17:
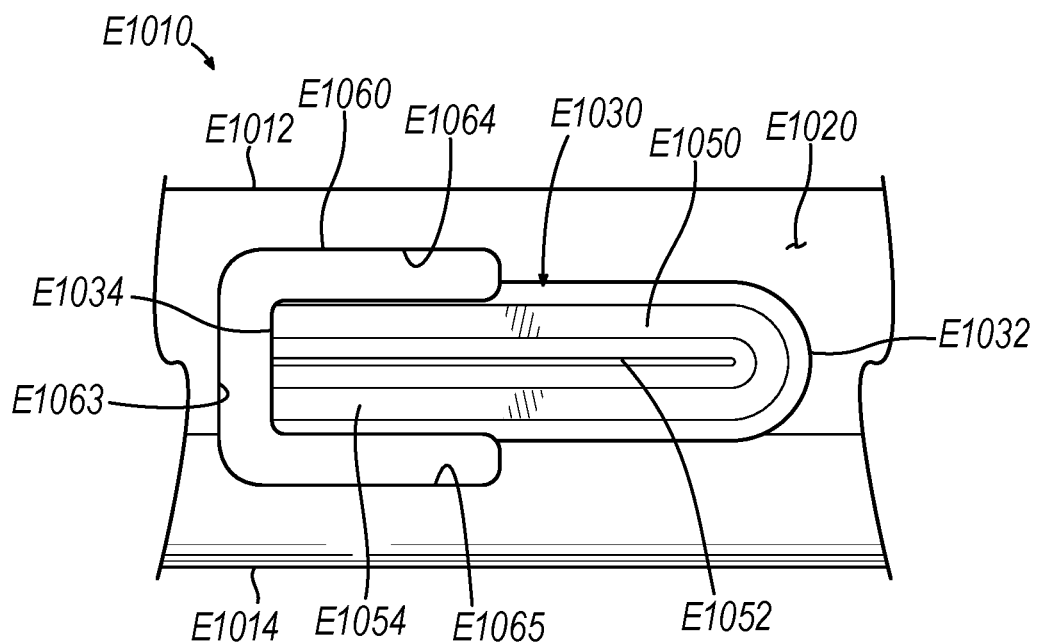
FIG. 17 depicts a partial side elevational view of another example of a lower pan of a staple cartridge for use with the end effector of FIG. 2 and having a retention tab extending laterally outwardly from a sidewall of the lower pan, the lower pan further having a distal C-shaped relief slot adjacent a distal end of the retention tab.

J. Example of Cartridge Pan with C-Shaped Relief Slot at One End of Retention Tab FIG. 17 shows a portion of another example of a lower pan (E1010) that may be readily incorporated into staple cartridge (70) in place of lower pan (76). Lower pan (E1010) may be similar to lower pan (E110) described above, except as otherwise described below. In this regard, lower pan (E1010) may be configured to be coupled to an underside of cartridge body (72) such that sled (82) and staple drivers (84) may be movably captured between cartridge body (72) and pan (E1010). Pan (E1010) of the present example includes a laterally-opposed pair of sidewalls (E1012) (one shown) coupled to each other by a bottom wall (E1014), such that sidewalls (E1012) and bottom wall (E1014) collectively define a trough (not shown) similar to trough (E116) that is sized and configured to securely receive a cartridge body (not shown), such as cartridge body (72). Each sidewall (E1012) has a respective laterally inner side surface (not shown) similar to laterally inner side surfaces (E118), which may confront and/or frictionally engage a respective laterally outer side surface of cartridge body (72); and a respective laterally outer side surface (E1020), which may confront and/or frictionally engage a respective laterally inner side surface (E102) of a channel (E100) of a cartridge jaw (not shown), such as cartridge jaw (42). While pan (E1010) is shown and described for incorporation into cartridge (70) and as being used in conjunction with channel (E100), it will be appreciated that pan (E1010) may be incorporated into any other suitable cartridge and/or may be used in conjunction with any other suitable channel.

In the example shown, pan (E1010) also includes a retention tab (E1030) extending laterally outwardly from each sidewall (E1012). Each retention tab (E1030) extends longitudinally between a respective proximal end (E1032) and a respective distal end (E1034), and includes laterally inner surfaces that collectively define a respective distally open-ended recess (not shown) similar to recess (E146) for permitting laterally-inward flexing of the respective retention tab (E1030) into the respective recess. In the example shown, the proximal end of each recess is closed by the proximal end (E1032) of the respective retention tab (E1030). In other versions, each recess may be proximally open-ended and the distal end of each recess may be closed by the distal end (E1034) of the respective retention tab (E1030), or each recess may be open-ended both proximally and distally as described above in connection with recess (E146). Each retention tab (E1030) also includes an upper, laterally outer surface (E1050) extending downwardly and laterally outwardly from an upper region of the laterally outer side surface (E1020) of the respective sidewall (E1012), a middle, laterally outer surface (E1052) extending vertically downwardly from the respective upper, laterally outer surface (E1050), and a lower, laterally outer surface (E1054) extending downwardly and laterally inwardly from the respective middle, laterally outer surface (E1052) to a lower region of the laterally outer side surface (E1020) of the respective sidewall (E1012).

In the example shown, pan (E1010) also includes a relief slot (E1060) extending laterally through each sidewall (E1012) from the inner side surface thereof to the laterally outer side surface (E1020) thereof. Each relief slot (E1060) is positioned adjacent to a corresponding retention tab (E1030) to impart the corresponding retention tab (E1030) with a reduced stiffness and/or increased resilience. In this regard, each relief slot (E1060) includes a distal vertical slot portion (E1063) positioned adjacent to the distal end (E1034) of the corresponding retention tab (E1030), an upper horizontal slot portion (E1064) extending longitudinally from an upper end of the respective vertical slot portion (E1063), and a lower horizontal slot portion (E1065) extending longitudinally from a lower end of the respective distal vertical slot portion (E1063) such that each relief slot (E1060) is substantially C-shaped. More particularly, the distal vertical slot portion (E1063) of each relief slot (E1060) extends along the distal end (E1034) of the corresponding retention tab (E1030), the upper horizontal slot portion (E1064) of each relief slot (E1060) extends proximally from the upper end of the respective vertical slot portion (E1063) along a distal portion of an upper edge of the corresponding retention tab (E1030), and the lower horizontal slot portion (E1065) of each relief slot (E1060) extends proximally from the lower end of the respective vertical slot portion (E1063) along a distal portion of a lower edge of the corresponding retention tab (E1030). Due to the recess of each retention tab (E1030) being distally open-ended as described above, vertical slot portion (E1063) of each relief slot (E1060) may open directly into the respective recess.

While vertical slot portion (E1063) of the present example is positioned adjacent to and/or along the distal end (E1034) of the corresponding retention tab (E1030), vertical slot portion (E1063) may alternatively be positioned adjacent to and/or along the proximal end (E1032) of the corresponding retention tab (E1030). In such cases, horizontal slot portions (E1064, E1065) may extend distally from respective ends of the respective vertical slot portion (E1063) along a proximal portion of the respective upper or lower edge of the corresponding retention tab (E1030), for example.

In some versions, retention tabs (E1030) and relief slots (E1060) may be arranged on sidewalls (E1012) in laterally-opposed pairs with each laterally-opposed pair of retention tabs (E1030) and each laterally-opposed pair of relief slots (E1060) being symmetrical relative to a longitudinal axis of pan (E1010). In other versions, retention tabs (E1030) and/or relief slots (E1060) may alternatively be configured substantially differently on each sidewall (E1012) of pan (E1010) so as to be asymmetrical relative to the longitudinal axis of pan (E1010). For example, the retention tab (E1030) and relief slots (E1060) on one sidewall (E1012) may be offset in the vertical direction and/or offset in the longitudinal direction from the retention tab (E1030) and relief slots (E1060) on the other sidewall (E1012). In addition, or alternatively, the retention tab (E1030) and relief slots (E1060) on one sidewall (E1012) may be sized and/or shaped substantially differently from the retention tab (E1030) and relief slots (E1060) on the other sidewall (E1012), such as by being sized and/or shaped in accordance with any of the other teachings provided herein.

Figure 18:
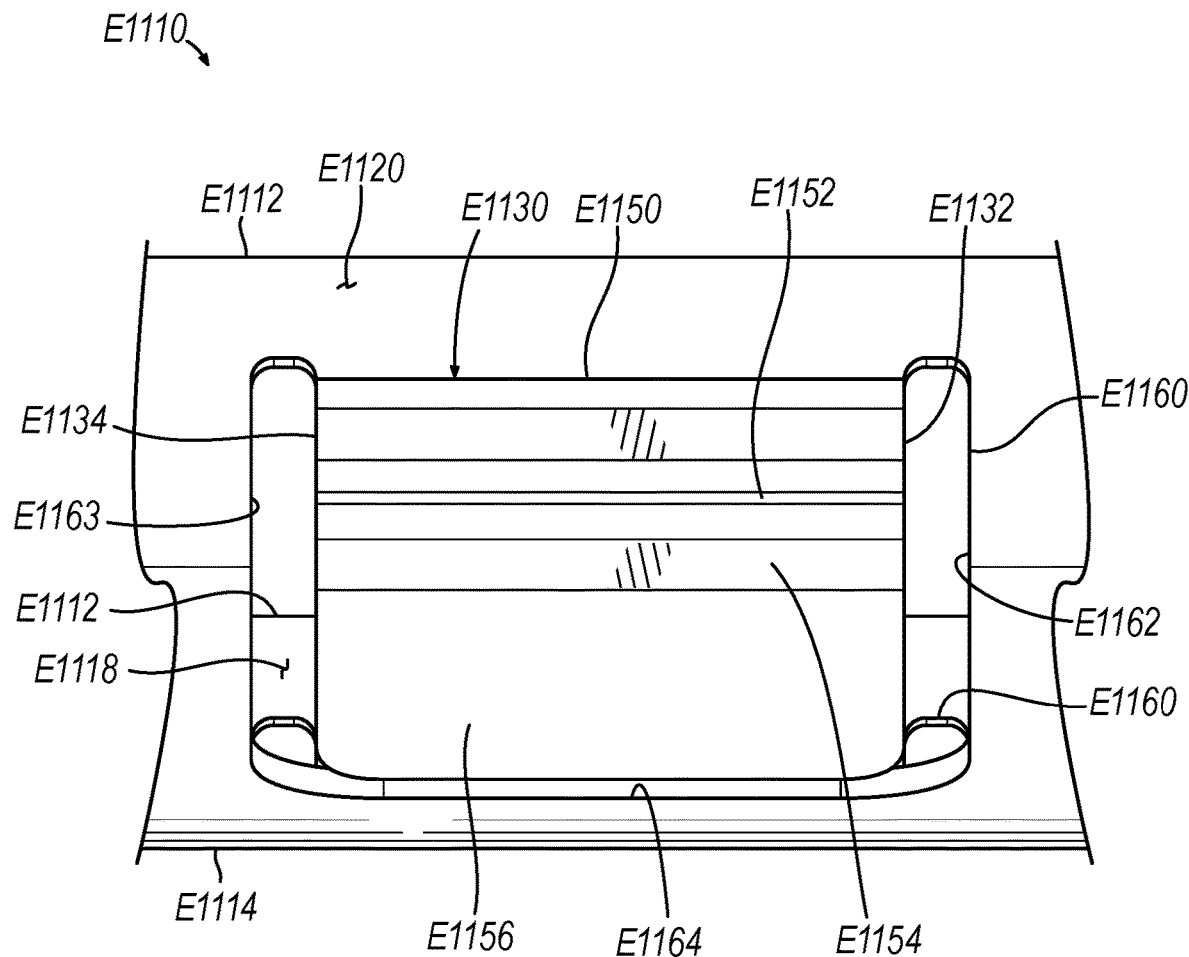
FIG. 18 depicts a partial side perspective view of another example of a lower pan of a staple cartridge for use with the end effector of FIG. 2 and having a retention tab extending laterally outwardly from a sidewall of the lower pan, the retention tab being partially surrounded by a U-shaped relief slot defined in both the sidewall and a bottom wall of the lower pan.
Figure 19:
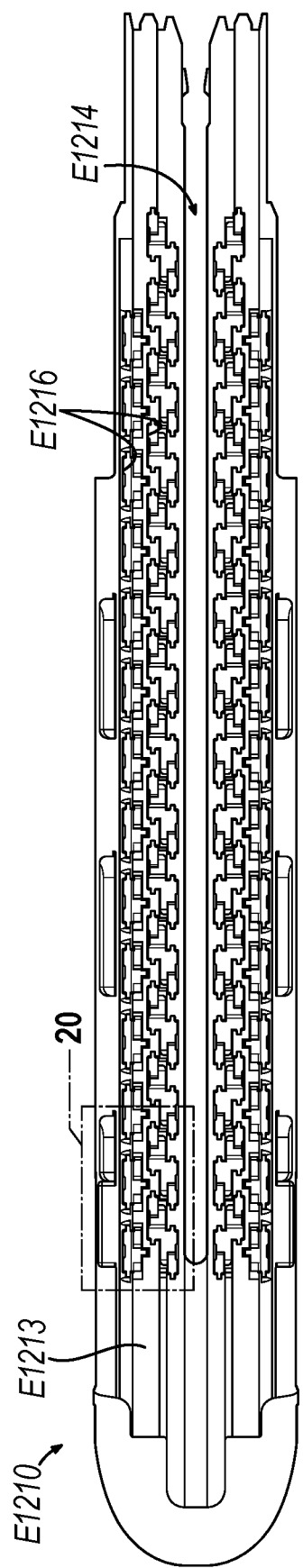
FIG. 19 depicts a bottom plan view of another example of a cartridge body of a staple cartridge for use with the end effector of FIG. 2 and having a thinned distal staple driver pocket support.

K. Example of Cartridge Pan with Retention Tab Partially Surrounded by Downwardly-Extended U-Shaped Relief Slot FIG. 18 shows a portion of another example of a lower pan (E1110) that may be readily incorporated into staple cartridge (70) in place of lower pan (76). Lower pan (E1110) may be similar to lower pan (E110) described above, except as otherwise described below. In this regard, lower pan (E1110) may be configured to be coupled to an underside of cartridge body (72) such that sled (82) and staple drivers (84) may be movably captured between cartridge body (72) and pan (E1110). Pan (E1110) of the present example includes a laterally-opposed pair of sidewalls (E1112) coupled to each other by a bottom wall (E1114), such that sidewalls (E1112) and bottom wall (E1114) collectively define a trough (not shown) similar to trough (E116) that is sized and configured to securely receive a cartridge body (not shown), such as cartridge body (72). Each sidewall (E1112) has a respective laterally inner side surface (E1118), which may confront and/or frictionally engage a respective laterally outer side surface of cartridge body (72); and a respective laterally outer side surface (E1120), which may confront and/or frictionally engage a respective laterally inner side surface (E102) of a channel (E100) of a cartridge jaw (not shown), such as cartridge jaw (42). While pan (E1110) is shown and described for incorporation into cartridge (70) and as being used in conjunction with channel (E100), it will be appreciated that pan (E1110) may be incorporated into any other suitable cartridge and/or may be used in conjunction with any other suitable channel.

In the example shown, pan (E1110) also includes a retention tab (E1130) extending laterally outwardly from each sidewall (E1112). Each retention tab (E1130) extends longitudinally between a respective proximal end (E1132) and a respective distal end (E1134), and includes laterally inner surfaces that collectively define a respective open-ended recess (not shown) similar to recess (E146) for permitting laterally-inward flexing of the respective retention tab (E1130) into the respective recess. Each retention tab (E1130) also includes an upper, laterally outer surface (E1150) extending downwardly and laterally outwardly from an upper region of the laterally outer side surface (E1120) of the respective sidewall (E1112), a middle, laterally outer surface (E1152) extending vertically downwardly from the respective upper, laterally outer surface (E1150), a lower, laterally outer surface (E1154) extending downwardly and laterally inwardly from the respective middle, laterally outer surface (E1152), and a bottom surface (E1156) extending laterally inwardly from the respective lower, laterally outer surface (E1154) toward a middle region of bottom wall (E1114).

In the example shown, pan (E1110) also includes a relief slot (E1160) extending laterally through each sidewall (E1112) from the inner side surface thereof to the laterally outer side surface (E1120) thereof, and further extending vertically through bottom wall (E1114). Each relief slot (E1160) is positioned adjacent to a corresponding retention tab (E1130) to impart the corresponding retention tab (E1130) with a reduced stiffness and/or increased resilience. In this regard, each relief slot (E1160) includes a proximal vertical slot portion (E1162) positioned adjacent to the proximal end (E1132) of the corresponding retention tab (E1130), a distal vertical slot portion (E1163) positioned adjacent to the distal end (E1134) of the corresponding retention tab (E1130), and a horizontal slot portion (E1164) extending longitudinally between the lower ends of the respective vertical slot portions (E1162, E1163), such that each relief slot (E1160) is substantially U-shaped. More particularly, the proximal vertical slot portion (E1162) of each relief slot (E1160) extends along the proximal end (E1132) of the corresponding retention tab (E1130), and the distal vertical slot portion (E1163) of each relief slot (E1160) extends along the distal end (E1134) of the corresponding retention tab (E1130), such that each retention tab (E1130) is longitudinally flanked by the vertical slot portions (E1162, E1163) of a corresponding relief slot (E1160). In the example shown, vertical sot portions (E1162, E1163) each extend further downwardly than the corresponding retention tab (E1130) such that the lower ends of vertical slot portions (E1162, E1163) each extend through bottom wall (E1114); and the horizontal slot portion (E1164) of each relief slot (E1160) extends through bottom wall (E1114) along the entire lower edge of the corresponding retention tab (E1130) to thereby space apart the lower, laterally inner edge of the corresponding retention tab (E1130) from bottom wall (E1114), such that each retention tab (E1130) may be cantilevered from the upper region of the laterally outer side surface (E1120) of the respective sidewall (E1112). It will be appreciated that such a cantilevered configuration may further reduce the stiffness and/or increase the resilience of each retention tab (E1130). Due to the recess of each retention tab (E1130) being open-ended as described above, vertical slot portions (E1162, E1163) of each relief slot (E1160) may open directly into the respective recess.

In some versions, retention tabs (E1130) and relief slots (E1160) may be arranged on sidewalls (E1112) in laterally-opposed pairs with each laterally-opposed pair of retention tabs (E1130) and each laterally-opposed pair of relief slots (E1160) being symmetrical relative to a longitudinal axis of pan (E1110). In other versions, retention tabs (E1130) and/or relief slots (E1160) may alternatively be configured substantially differently on each sidewall (E1112) of pan (E1110) so as to be asymmetrical relative to the longitudinal axis of pan (E1110). For example, the retention tab (E1130) and relief slots (E1160) on one sidewall (E1112) may be offset in the vertical direction and/or offset in the longitudinal direction from the retention tab (E1130) and relief slots (E1160) on the other sidewall (E1112). In addition, or alternatively, the retention tab (E1130) and relief slots (E1160) on one sidewall (E1112) may be sized and/or shaped substantially differently from the retention tab (E1130) and relief slots (E1160) on the other sidewall (E1112), such as by being sized and/or shaped in accordance with any of the other teachings provided herein.

III. Examples of Cartridge Bodies Having Thinned Regions to Promote Cartridge Flexing In some instances, it may be desirable to provide cartridge body (72) of staple cartridge (70) with one or more thinned regions to promote flexing of one or more portions of staple cartridge (70) when sled (82) is in the distal fired position. For example, such thinned regions may promote laterally-inward flexing of cartridge body (72) and/or lower pan (76) during removal of staple cartridge (70) from the channel of cartridge jaw (42), and may thereby reduce the cartridge removal force while minimizing any impact to the cartridge retention force. Each of the examples of cartridge bodies (E1210, E1310) described below provides such functionality.

A. Example of Cartridge Body with Thinned Distal Driver Pocket Supports

FIGS. 19-22 show another example of a cartridge body (E1210) that may be readily incorporated into staple cartridge (70) in place of cartridge body (72). Cartridge body (E1210) may be similar to cartridge body (72) described above, except as otherwise described below. In this regard, cartridge body (E1210) presents an upper deck (E1212) defining a first stapling surface, and an underside (E1213). A vertical knife slot (E1214) extends longitudinally through cartridge body (E1210) and is configured to slidably receive distal knife portion (50) of firing beam (46). In the present version, three rows of cartridge pockets (E1216) (also referred to as "staple openings," "staple apertures," or "staple cavities") are formed through upper deck (E1212) and underside (E1213) along each lateral side of knife slot (E1214). Underside (E1213) may be coupled to lower pan (E110) such that sled (82) and a plurality of staple drivers (E1218) may be movably captured between cartridge body (E1210) and pan (E110). While cartridge body (E1210) is shown and described for incorporation into cartridge (70) along with pan (E110) and as being used in conjunction with channel (E100), it will be appreciated that cartridge body (E1210) may be incorporated into any other suitable cartridge and/or may be used in conjunction with any other suitable channel. For example, cartridge body (E1210) may be incorporated into cartridge (70) while retaining pan (76), or may be incorporated into cartridge (70) along with any of the other pans (E210, E310, E410, E510, E610, E710, E810, E910, E1010, E1110) described herein.

In the example shown, cartridge body (E1210) also includes a pair of sled rail tracks (E1220, E1222) extending longitudinally on each lateral side of knife slot (E1214) for slidably receiving respective rails of sled (82). More particularly, cartridge body (E1210) includes a laterally inner sled rail track (E1220) and a laterally outer sled rail track (E1222) on each lateral side of knife slot (E1214) for slidably receiving respective laterally inner and outer rails of sled (82). In this regard each laterally outer sled rail track (E1222) is defined between a corresponding interior wall (E1224) of cartridge body and a plurality of driver pocket supports (E1230a, E1230b), with interior wall (E1224) defining a laterally inner boundary of the respective laterally outer sled rail track (E1222) and with driver pocket supports (E1230a, E1230b) collectively defining a laterally outer boundary of the respective laterally outer sled rail track (E1222).

Figure 20:
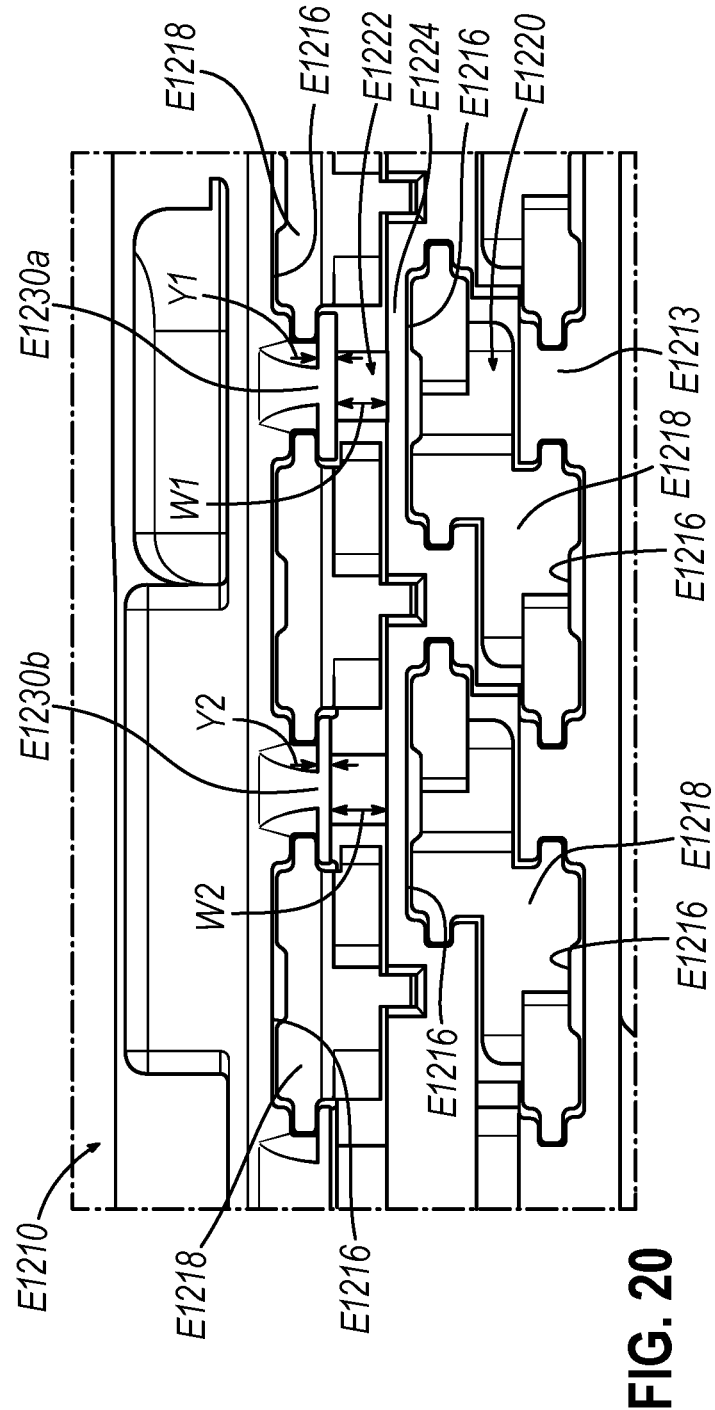
FIG. 20 depicts a magnified view of area 20 of the cartridge body of FIG. 19 as indicated in FIG. 19.
Figure 21:
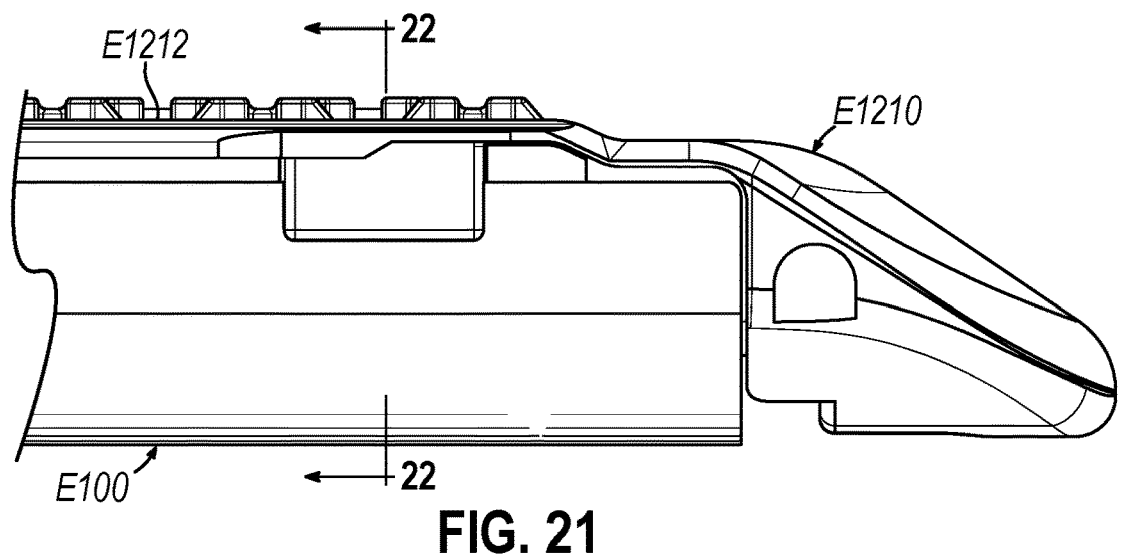
FIG. 21 depicts a partial side elevational view of a staple cartridge including the cartridge body of FIG. 19 and the lower pan of FIG. 8, showing the staple cartridge removably installed into the channel of FIG. 8.

As shown in FIG. 20, the illustrated plurality of driver pocket supports (E1230a, E1230b) includes a plurality of proximal driver pocket supports (E1230a) having a first thickness (Y1) and a distal (e.g., distalmost) driver pocket support (E1230b) having a second thickness (Y2) substantially less than the first thickness (Y1), such that a laterally inner surface of distal driver pocket support (E1230b) may be spaced farther apart from interior wall (E1224) than proximal driver pocket supports (E1230a). For example, the first thickness (Y1) may be about 0.007 in, while the second thickness (Y2) may be about 0.005 in, such that the second thickness (Y2) may be less than the first thickness (Y1) by about 0.002 in. In this manner, each laterally outer sled rail track (E1222) may have a first, proximal width (W1) and a second, distal width (W2) greater than the first width (W1) by an amount substantially equal to the difference between the first and second thicknesses (Y1, Y2). For example, the second width (W2) may be greater than the first width (W1) by about 0.002 in.

Figure 22:
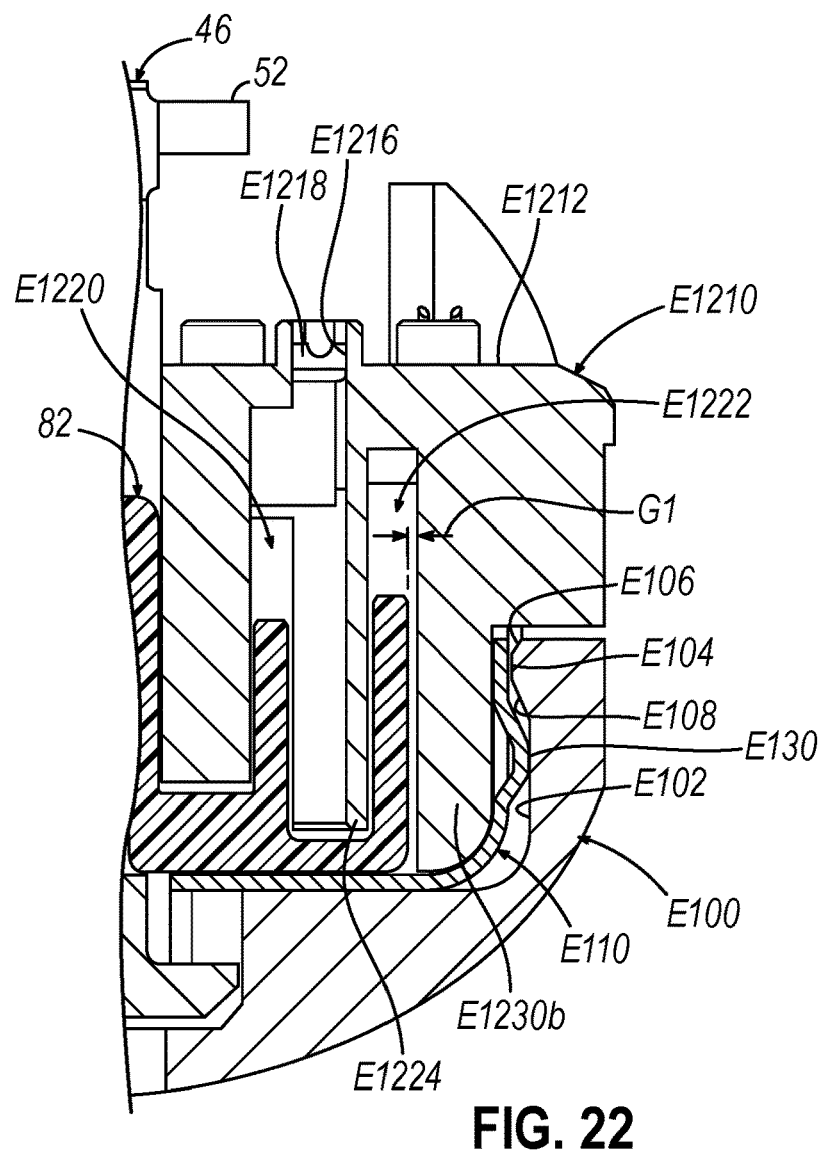
FIG. 22 depicts an end cross-sectional view of the staple cartridge and channel of FIG. 21, taken along line 22-22 of FIG. 21, showing a sled of the staple cartridge in a distal fired position.

Due to the increased second width (W2) of each laterally outer sled rail track (E1222), the laterally outer rails of sled (82) may each be spaced apart from the respective distal driver pocket support (E1230b) by a gap (G1) when sled (82) is in the distal fired position, as shown in FIG. 22. In this regard, the gap (G1) between each laterally outer rail of sled (82) and the respective distal driver pocket support (E1230b) may be substantially greater than any gap between each laterally outer rail of sled (82) and the respective proximal driver pocket supports (E1230a). For example, the gap (G1) between each laterally outer rail of sled (82) and the respective distal driver pocket support (E1230b) may be about 0.003 in, while any gap between each laterally outer rail of sled (82) and the respective proximal driver pocket supports (E1230a) may be about 0.001 in. The increased gap (G1) between each laterally outer rail of sled (82) and the respective distal driver pocket support (E1230b) may provide more space for staple cartridge (70) (e.g., cartridge body (E1210) and/or pan (E110)) to deflect laterally inwardly before contacting the laterally outer rails of sled (82), such as during removal of staple cartridge (70) from channel (E100). Such additional space for staple cartridge (70) to deflect may reduce any resistance to laterally inward flexing of staple cartridge (70) that might otherwise be caused by sled (82) being in the distal fired position, thereby reducing the cartridge removal force. For example, the laterally inward flexing of staple cartridge (70) permitted by such additional space may assist with disengaging retention tab (E130) of lower pan (E110) from channel (E100) (e.g., from detent (E104) of channel (E100)).

While distal driver pocket support (E1230b) of the present example has a laterally inner surface that is substantially flat (e.g., planar) and that is oriented substantially parallel to knife slot (E1214), the laterally inner surface of each distal driver pocket support (E1230b) may alternatively be any one or more of concave, convex, tapered in the vertical direction and/or tapered in the longitudinal direction. While only the distalmost driver pocket support (E1230b) has been described as having the second thickness (Y2), it will be appreciated that any suitable driver pocket supports (E1230a, E1230b) may have the second thickness (Y2), such as all driver pocket supports that are at a substantially same longitudinal position as any portion of the corresponding laterally outer rail of sled (82) when sled (82) is in the distal fired position. In this regard, it may be desirable to provide at least some proximal driver pocket supports (E1230a) with the first thickness (Y1) to provide a relatively tight gap between sled (82) and such proximal driver pocket supports (E1230a) during firing to promote proper deployment and forming of staples (86).

B. Example of Cartridge Body with Recessed Laterally Outer Surfaces

Figure 23:
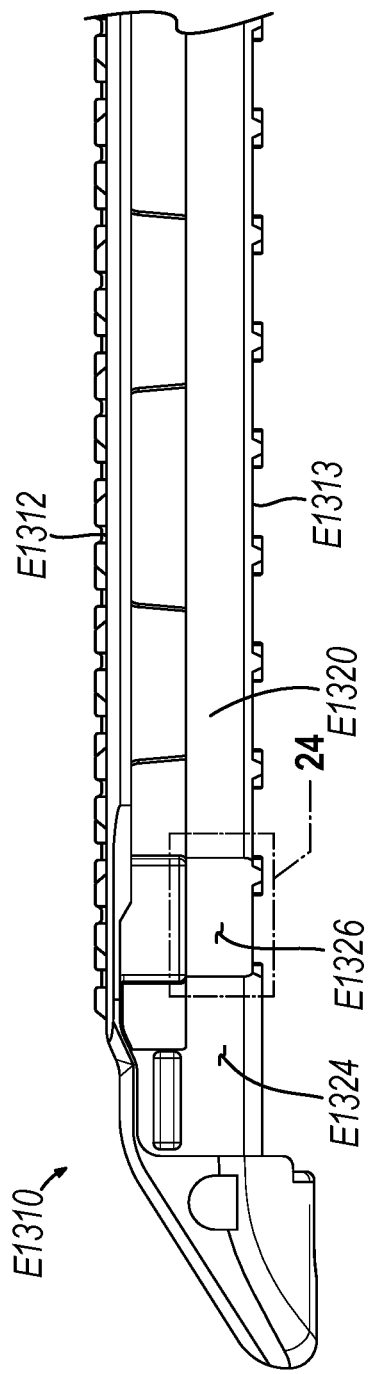
FIG. 23 depicts a partial side elevational view of another example of a cartridge body of a staple cartridge for use with the end effector of FIG. 2 and having a recessed laterally outer surface.
Figure 24:
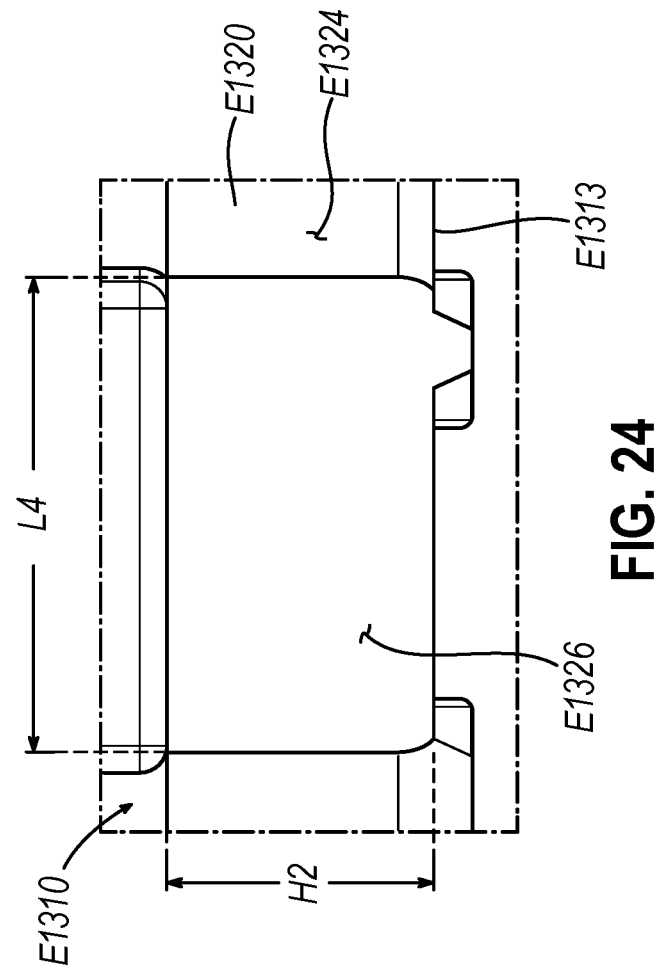
FIG. 24 depicts a magnified view of area 24 of the cartridge body of FIG. 23 as indicated in FIG. 23.
Figure 25:
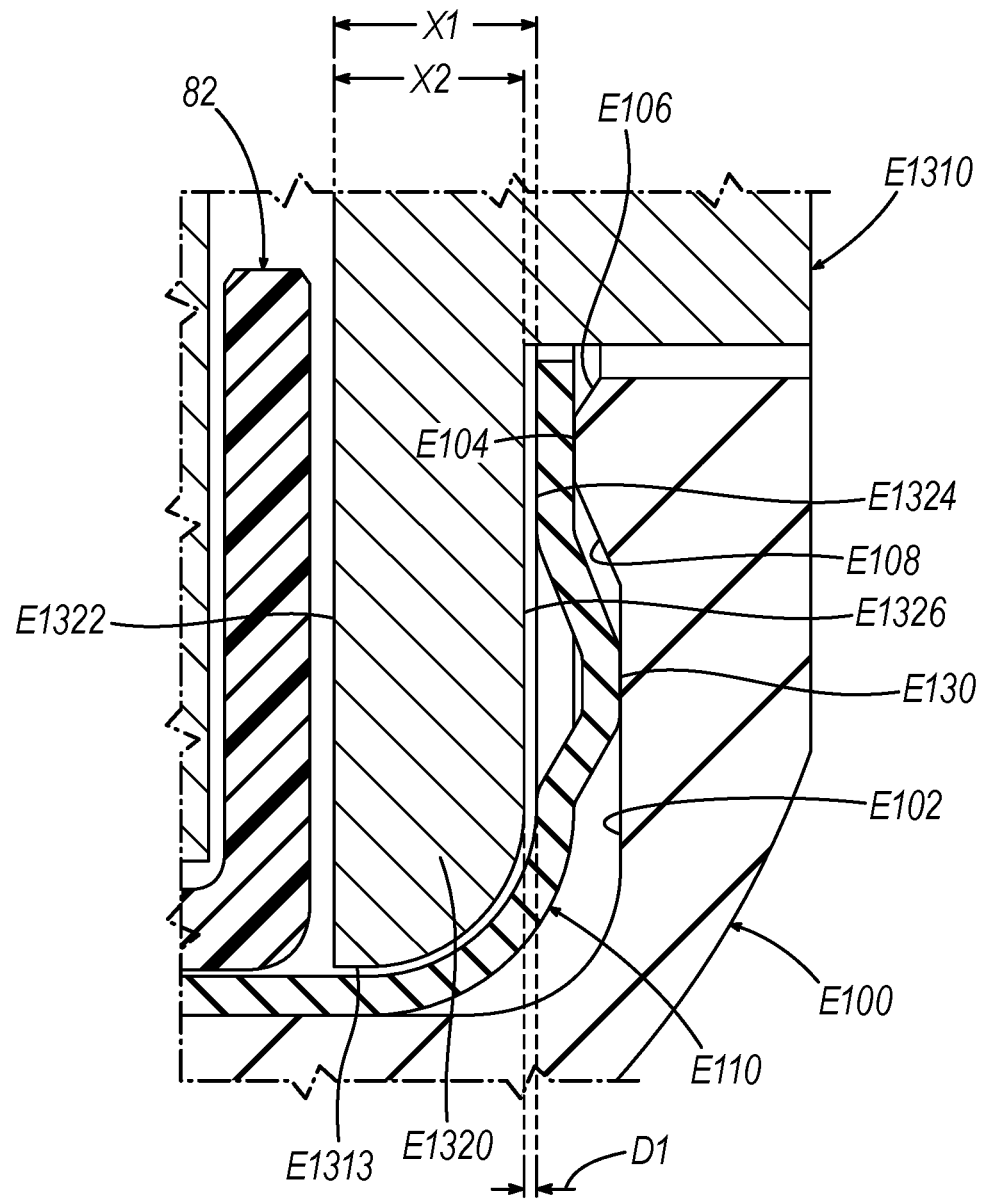
FIG. 25 depicts an end cross-sectional view of a staple cartridge including the cartridge body of FIG. 23 and the lower pan of FIG. 8, showing the staple cartridge removably installed into the channel of FIG. 8.

FIGS. 23-25 show another example of a cartridge body (E1310) that may be readily incorporated into staple cartridge (70) in place of cartridge body (72). Cartridge body (E1310) may be similar to cartridge body (72) described above, except as otherwise described below. In this regard, cartridge body (E1310) presents an upper deck (E1312) defining a first stapling surface, and an underside (E1313). A vertical knife slot (not shown) similar to knife slot (78) extends longitudinally through cartridge body (E1310) and is configured to slidably receive distal knife portion (50) of firing beam (46). While not shown, three rows of cartridge pockets similar to cartridge pockets (E1216) are formed through upper deck (E1312) and underside (E1313) along each lateral side of the knife slot. Underside (E1313) may be coupled to lower pan (E110) such that sled (82) and a plurality of staple drivers (not shown) similar to staple drivers (E1218) may be movably captured between cartridge body (E1310) and pan (E110). While cartridge body (E1310) is shown and described for incorporation into cartridge (70) along with pan (E110) and as being used in conjunction with channel (E100), it will be appreciated that cartridge body (E1310) may be incorporated into any other suitable cartridge and/or may be used in conjunction with any other suitable channel. For example, cartridge body (E1310) may be incorporated into cartridge (70) while retaining pan (76), or may be incorporated into cartridge (70) along with any of the other pans (E210, E310, E410, E510, E610, E710, E810, E910, E1010, E1110) described herein.

In the example shown, cartridge body (E1310) also includes a laterally-opposed pair of sidewalls (E1320) (one shown). Each sidewall (E1320) has a respective laterally inner side surface (E1322), which may partially define a laterally outer sled rail track of cartridge body (E1310); and a respective laterally outer side surface (E1324), which may confront and/or frictionally engage a respective laterally inner side surface (E118) of lower pan (E110). Cartridge body (E1310) of the present example further includes a laterally-opposed pair of recessed laterally outer surfaces (E1326) (one shown) that extend upwardly from underside (E1313) and that are recessed laterally inwardly relative to the respective laterally outer side surface (E1324). Each recessed laterally outer surface (E1326) may be disposed at a relatively distal location along a length of cartridge body (E1310). For example, each recessed laterally outer surface (E1326) may be at a substantially same position in the longitudinal direction as sled (82) when sled (82) is in the distal fired position. In the example shown, each recessed laterally outer surface (E1326) is at a substantially same position in the longitudinal direction as a corresponding retention tab (E130) of lower pan (E110). As shown in FIG. 24, each recessed laterally outer surface (E1326) has a length (LA) and a height (H2), which may be substantially equal to or greater than the length (L) and height (H1), respectively, of the corresponding retention tab (E130). For example, the length (L4) of each recessed laterally outer surface (E1326) may be about 0.185 in, and/or the height (H2) of each recessed laterally outer surface (E1326) may be about 0.094 in.

As shown in FIG. 25, the illustrated sidewall (E1320) has a first thickness (X1) defined between the respective laterally inner and outer side surfaces (E1322, E1324), and a second thickness (X2) defined between the respective laterally inner side surface (E1322) and recessed laterally outer surface (E1326) that is substantially less than the first thickness (X1), such that each recessed laterally outer surface (E1326) is recessed laterally inwardly relative to the respective laterally outer side surface (E1324) by a depth (D1). For example, the first thickness (X1) may be about 0.011 in, while the second thickness (X2) may be about 0.008 in, such that the depth (D1) may be about 0.003 in.

Due to the depth (D1) of each recessed laterally outer surface (E1326) relative to the respective laterally outer side surface (E1324), the laterally inner side surfaces (E118) of pan (E110) may each be spaced apart from the respective recessed laterally outer surface (E1326) by a localized gap defined by the same depth (D1) while the laterally inner side surfaces (E118) may each frictionally engage the respective laterally outer side surface (E1324) when pan (E110) is coupled to underside of cartridge body (E1310), as shown in FIG. 25. The gap between each laterally inner side surface (E118) of pan (E110) and the respective recessed laterally outer surface (E1326) may provide more space for staple cartridge (70) and, more particularly, pan (E110) to deflect laterally inwardly, such as during removal of staple cartridge (70) from channel (E100). Such additional space for pan (E110) to deflect may reduce any resistance to laterally inward flexing of pan (E110) that might otherwise be caused by cartridge body (E1310), thereby reducing the cartridge removal force. For example, the laterally inward flexing of pan (E110) permitted by such additional space may assist with disengaging retention tab (E130) of lower pan (E110) from channel (E100) (e.g., from detent (E104) of channel (E100)).

IV. Examples of Wedge Sleds Configured to Provide Increased Cartridge-to-Sled Gap to Promote Cartridge Flexing In some instances, it may be desirable to provide sled (82) of staple cartridge (70) with one or more features configured to increase the lateral gap between the outer rails of sled (82) and the driver pocket supports of cartridge body (72). For example, such features may promote laterally-inward flexing of cartridge body (72) and/or lower pan (76) during removal of staple cartridge (70) from the channel of cartridge jaw (42), and may thereby reduce the cartridge removal force while minimizing any impact to the cartridge retention force. Each of the examples of sleds (E1410, E1510) described below provides such functionality.

A. Example of Wedge Sled with Recessed Laterally Outer Surfaces

Figure 26:
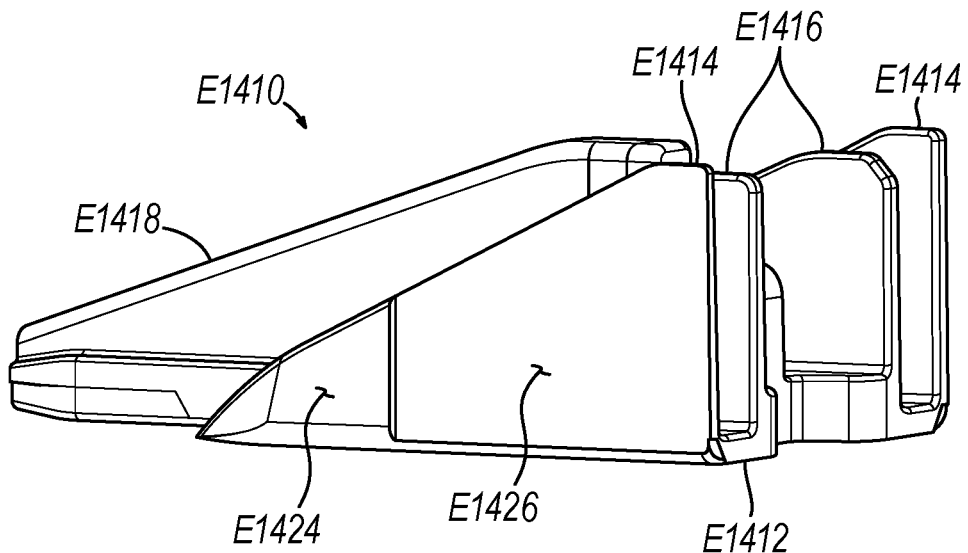
FIG. 26 depicts a perspective view of another example of a sled of a staple cartridge for use with the end effector of FIG. 2 and having a recessed laterally outer surface.
Figure 27:
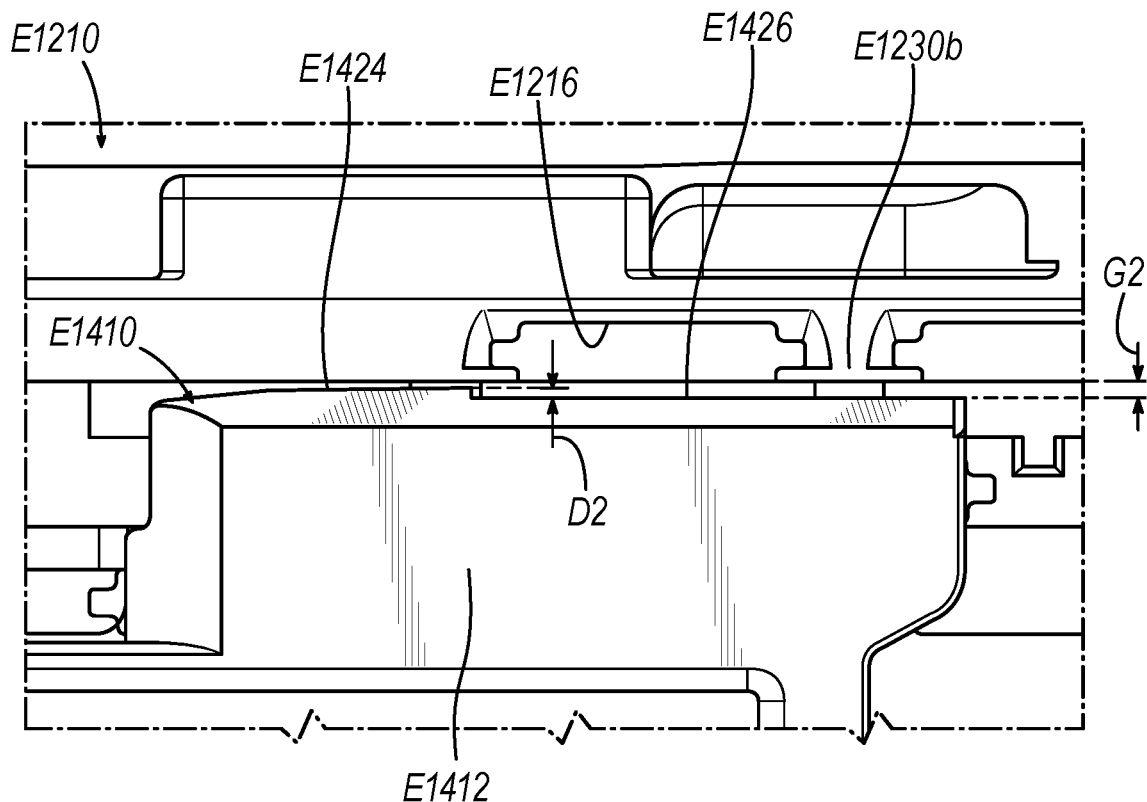
FIG. 27 depicts a partial bottom plan view of a staple cartridge including the sled of FIG. 26 and the cartridge body of FIG. 19, showing the sled in a distal fired position.

FIGS. 26-27 show another example of a wedge sled (E1410) that may be readily incorporated into staple cartridge (70) in place of wedge sled (82). Wedge sled (E1410) may be similar to wedge sled (82) described above, except as otherwise described below. In this regard, wedge sled (E1410) may be movably captured between cartridge body (72) and pan (76) and may be actuated longitudinally within staple cartridge (70) by distal knife portion (50) during a firing stroke. While wedge sled (E1410) is shown and described for incorporation into cartridge (70) along with pan (E110) and cartridge body (E1210), and as being used in conjunction with channel (E100), it will be appreciated that wedge sled (E1410) may be incorporated into any other suitable cartridge and/or may be used in conjunction with any other suitable channel. For example, wedge sled (E1410) may be incorporated into cartridge (70) while retaining pan (76) and/or cartridge body (72), or may be incorporated into cartridge (70) along with any of the other pans (E210, E310, E410, E510, E610, E710, E810, E910, E1010, E1110) described herein and/or along with cartridge body (E1310) described herein.

In the example shown, wedge sled (E1410) includes a base (E1412), a laterally-opposed pair of outer sled rails (E1414) extending upwardly from base (E1412), a laterally-opposed pair of inner sled rails (E1416) extending upwardly from base (E1412) between outer sled rails (E1414), and a central nose (E1418) extending upwardly and/or distally from base (E1412) between inner sled rails (E1416). Sled rails (E1414, E1416) may also be referred to as "cam ramps" or "cam wedges." In this regard, sled rails (E1414, E1416) present angled cam surfaces for camming staple drivers (84) vertically upwardly within cartridge pockets (80) to drive staples (86) upwardly above deck (74), thereby ejecting staples (86) from cartridge pockets (80) and toward anvil jaw (44) during longitudinal actuation of wedge sled (E1410). In some versions, wedge sled (E1410) may comprise a metal material. In addition, or alternatively, wedge sled (E1410) may have a substantially greater material stiffness than that of cartridge body (72).

In the example shown, each outer rail (E1414) has a respective laterally outer side surface (E1424), which may confront and/or slidingly engage the laterally inner surfaces of driver pocket supports (E1230a, E1230b) during longitudinal actuation of wedge sled (E1410). Wedge sled (E1410) of the present example further includes a laterally-opposed pair of recessed laterally outer surfaces (E1426) (one shown) that extend upwardly from base (E1412) and proximally from the distal end of the respective outer rail (E1414), and that are recessed laterally inwardly relative to the respective laterally outer side surface (E1424). Each recessed laterally outer surface (E1426) may be at a substantially same position in the longitudinal direction as the corresponding distal driver pocket support (E1230b) when sled (82) is in the distal fired position. As shown, each recessed laterally outer surface (E1426) is recessed laterally inwardly relative to the respective laterally outer side surface (E1424) by a depth (D2).

Due to the depth (D2) of each recessed laterally outer surface (E1426) relative to the respective laterally outer side surface (E1424), the laterally inner surfaces of at least distal driver pocket supports (E1230b) may each be spaced apart from the respective recessed laterally outer surface (E1426) by a localized gap defined by the same depth (D2) when sled (82) is in the distal first position, as shown in FIG. 27. The increased gap (G2) between each laterally outer rail (E1414) of sled (E1410) and the respective distal driver pocket support (E1230b) may provide more space for staple cartridge (70) (e.g., cartridge body (E1210) and/or pan (E110)) to deflect laterally inwardly before contacting the laterally outer rails (E1414) of sled (E1410), such as during removal of staple cartridge (70) from channel (E100). Such additional space for staple cartridge (70) to deflect may reduce any resistance to laterally inward flexing of staple cartridge (70) that might otherwise be caused by sled (82) being in the distal fired position, thereby reducing the cartridge removal force. For example, the laterally inward flexing of staple cartridge (70) permitted by such additional space may assist with disengaging retention tab (E130) of lower pan (E110) from channel (E100) (e.g., from detent (E104) of channel (E100)).

B. Example of Wedge Sled with Tapered Laterally Outer Surfaces

Figure 28:
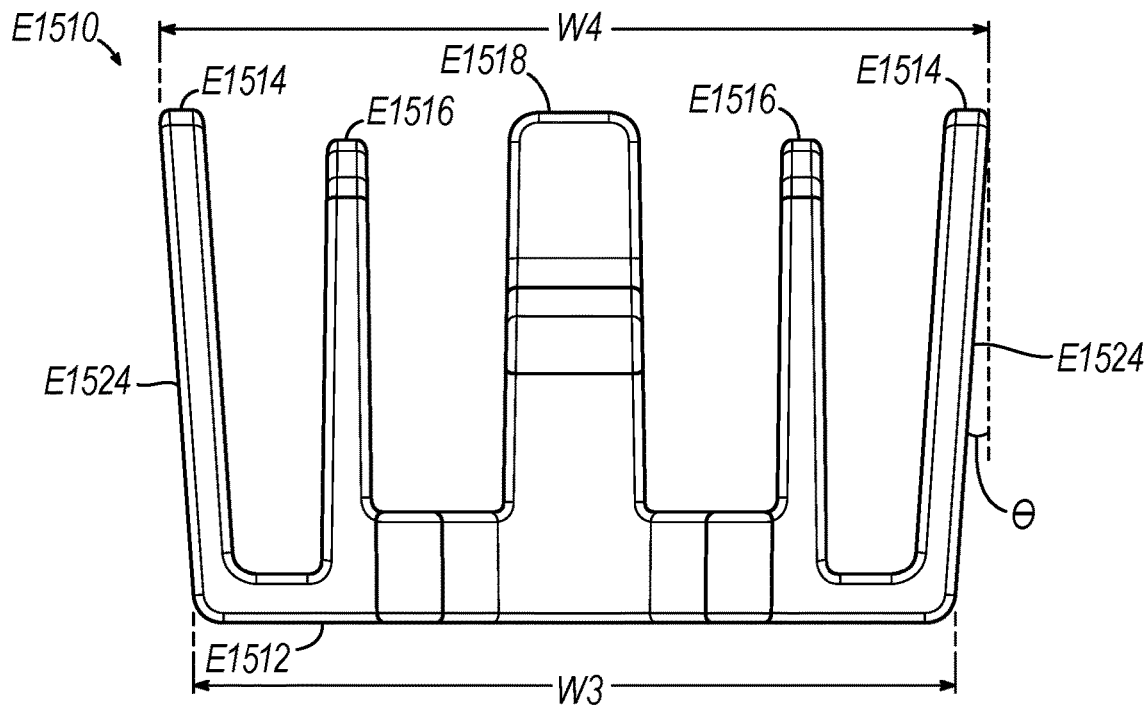
FIG. 28 depicts a rear elevational view of another example of a sled of a staple cartridge for use with the end effector of FIG. 2 and having tapered laterally outer surfaces.
Figure 29:
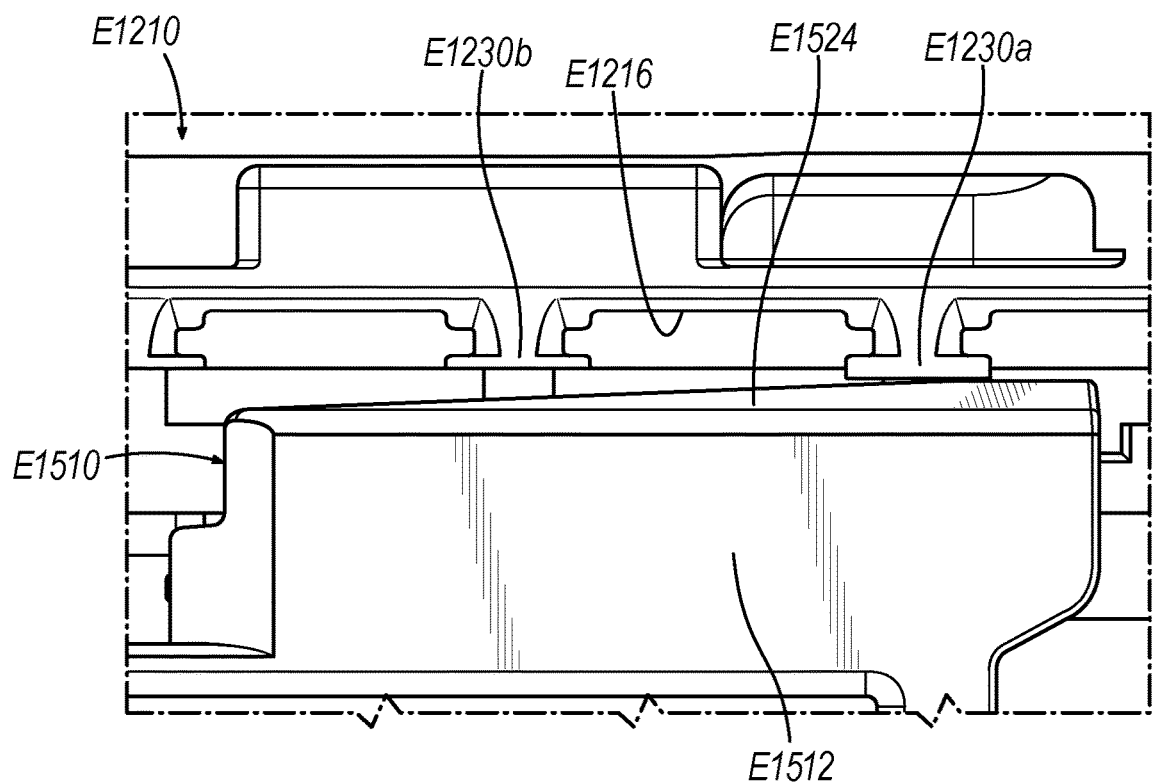
FIG. 29 depicts a partial bottom plan view of a staple cartridge including the sled of FIG. 28 and the cartridge body of FIG. 19, showing the sled in a distal fired position.

FIGS. 28-29 show another example of a wedge sled (E1510) that may be readily incorporated into staple cartridge (70) in place of wedge sled (82). Wedge sled (E1510) may be similar to wedge sled (82) described above, except as otherwise described below. In this regard, wedge sled (E1510) may be movably captured between cartridge body (72) and pan (76) and may be actuated longitudinally within staple cartridge (70) by distal knife portion (50) during a firing stroke. While wedge sled (E1510) is shown and described for incorporation into cartridge (70) along with pan (E110) and cartridge body (E1210), and as being used in conjunction with channel (E100), it will be appreciated that wedge sled (E1510) may be incorporated into any other suitable cartridge and/or may be used in conjunction with any other suitable channel. For example, wedge sled (E1510) may be incorporated into cartridge (70) while retaining pan (76) and/or cartridge body (72), or may be incorporated into cartridge (70) along with any of the other pans (E210, E310, E410, E510, E610, E710, E810, E910, E1010, E1110) described herein and/or along with cartridge body (E1310) described herein.

In the example shown, wedge sled (E1510) includes a base (E1512), a laterally-opposed pair of outer sled rails (E1514) extending upwardly from base (E1512), a laterally-opposed pair of inner sled rails (E1516) extending upwardly from base (E1512) between outer sled rails (E1514), and a central nose (E1518) extending upwardly and/or distally from base (E1512) between inner sled rails (E1516). Sled rails (E1514, E1516) may also be referred to as "cam ramps" or "cam wedges." In this regard, sled rails (E1514, E1516) present angled cam surfaces for camming staple drivers (84) vertically upwardly within cartridge pockets (80) to drive staples (86) upwardly above deck (74), thereby ejecting staples (86) from cartridge pockets (80) and toward anvil jaw (44) during longitudinal actuation of wedge sled (E1510). In some versions, wedge sled (E1510) may comprise a metal material. In addition, or alternatively, wedge sled (E1510) may have a substantially greater material stiffness than that of cartridge body (72).

In the example shown, each outer rail (E1514) has a respective laterally outer side surface (E1524), which may confront and/or slidingly engage the laterally inner surfaces of driver pocket supports (E1230a, E1230b) during longitudinal actuation of wedge sled (E1510). Inner rails (E1516) of the present example are substantially vertical, while outer rails (E1514) of the present example are each tilted or bent laterally outwardly from base (E1512), such that outer sled rails (E1514) are obliquely oriented relative to the horizontal plane and relative to a vertical-longitudinal plane. More particularly, each outer sled rail (E1514) is bent laterally outwardly at a same oblique angle ($\theta$) relative to the vertical-longitudinal plane (or to any plane parallel thereto), such that wedge sled (E1510) is substantially symmetric about the vertical-longitudinal plane, at least with respect to the configurations of sled rails (E1514, E1516). In this manner, each laterally outer side surface (E1524) may be tapered laterally inwardly and downwardly at the same oblique angle ($\theta$) relative to the vertical-longitudinal plane to provide sled (E1510) with a first, bottom width (W3) and a second, top width (W4) greater than the bottom width (W3). Each laterally outer side surface (E1524) may be at a substantially same position in the longitudinal direction as the corresponding distal driver pocket support (E1230b) when sled (82) is in the distal fired position.

Due to the varying widths (W3, W4) of sled (E1510), the laterally inner surfaces of driver pocket supports (E1230a, E1230b) may each be spaced apart from the respective tapered laterally outer side surface (E1524) by a gap that varies in the vertical direction when sled (82) is in the distal first position, as shown in FIG. 29. For example, the gap may be relatively large at or near base (E1512) and may be relatively small at or near the tops of outer rails (E1514) to promote proper deployment and forming of staples (86). Due to the configurations of angled cam surfaces presented by outer rails (E1514), this may result in an increased gap between each laterally outer rail (E1514) of sled (E1510) and the respective distal driver pocket support (E1230b). The increased gap between each laterally outer rail (E1514) of sled (E1510) and the respective distal driver pocket support (E1230b) may provide more space for staple cartridge (70) (e.g., cartridge body (E1210) and/or pan (E110)) to deflect laterally inwardly before contacting the laterally outer rails (E1514) of sled (E1510), such as during removal of staple cartridge (70) from channel (E100). Such additional space for staple cartridge (70) to deflect may reduce any resistance to laterally inward flexing of staple cartridge (70) that might otherwise be caused by sled (82) being in the distal fired position, thereby reducing the cartridge removal force. For example, the laterally inward flexing of staple cartridge (70) permitted by such additional space may assist with disengaging retention tab (E130) of lower pan (E110) from channel (E100) (e.g., from detent (E104) of channel (E100)).

While each laterally outer rail (E1514) of the present example tilted or bent to impart the respective laterally outer side surface (E1524) with a taper, it will be appreciated that laterally outer rails (E1514) may alternatively be substantially vertical and may have varying thicknesses to impart the respective laterally outer side surface (E1524) with a taper. While each laterally outer side surface (E1524) of the present example is tapered at a single angle ($\theta$) relative to the vertical-longitudinal plane, it will be appreciated that each laterally outer side surface (E1524) may alternatively be tapered at more than a single angle ($\theta$) relative to the vertical-longitudinal plane.

It will be understood that while the features shown and described above are presented in the context of staple cartridge (70) for surgical stapler (10), such features may also be applied to staple cartridges configured for use with various other types of surgical staplers, such as linear surgical staplers.

V. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A staple cartridge (70) for a surgical instrument (10), the staple cartridge (70) comprising: (a) a cartridge body (72, E1210, E1310) extending along a longitudinal axis and having an upper deck (74, E1212, E1312), wherein the upper deck (74, E1212, E1312) defines a stapling surface, wherein a plurality of pockets (80, E1216) extend through the upper deck (74, E1212, E1312) for receiving respective staples (86); and (b) a pan (E110, E210, E310, E410, E510, E610, E710, E810, E910, E1010, E1110) coupled to the cartridge body (72, E1210, E1310), wherein the pan (E110, E210, E310, E410, E510, E610, E710, E810, E910, E1010, E1110) includes: (i) a laterally-opposed pair of sidewalls (E112, E212, E312, E412, E512, E612, E712, E812, E912, E1012, E1112) spaced apart from each other to define a trough (E116), wherein the trough (E116) is sized and configured to receive the cartridge body (72, E1210, E1310), (ii) at least one retention tab (E130, E230a, E230b, E330, E430, E530, E630, E730, E830, E930, E1030, E1130) extending laterally outwardly from at least one sidewall (E112, E212, E312, E412, E512, E612, E712, E812, E912, E1012, E1112) of the laterally-opposed pair of sidewalls (E112, E212, E312, E412, E512, E612, E712, E812, E912, E1012, E1112), wherein the at least one retention tab (E130, E230a, E230b, E330, E430, E530, E630, E730, E830, E930, E1030, E1130) extends longitudinally between a proximal end (E132, E232, E332, E432, E532, E632, E732, E832, E932, E1032, E1132) and a distal end (E134, E234, E334, E434, E534, E634, E734, E834, E934, E1034, E1134), wherein the at least one retention tab (E130, E230a, E230b, E330, E430, E530, E630, E730, E830, E930, E1030, E1130) defines at least one recess (E146) extending laterally outwardly from the trough (E116), wherein the at least one recess (E146) opens through the at least one sidewall (E112, E212, E312, E412, E512, E612, E712, E812, E912, E1012, E1112) at at least one of the proximal end (E132, E232, E332, E432, E532, E632, E732, E832, E932, E1032, E1132) or the distal end (E134, E234, E334, E434, E534, E634, E734, E834, E934, E1034, E1134), and (iii) at least one relief slot (E160a, E160b, E260a, E260b, E260c, E360a, E360b, E460a, E460b, E460c, E560, E660a, E660b, E660c, E660d, E760, E860, E960a, E960b, E1060, E1160) extending through the at least one sidewall (E112, E212, E312, E412, E512, E612, E712, E812, E912, E1012, E1112), wherein the at least one relief slot (E160a, E160b, E260a, E260b, E260c, E360a, E360b, E460a, E460b, E460c, E560, E660a, E660b, E660c, E660d, E760, E860, E960a, E960b, E1060, E1160) is adjacent to the at least one of the proximal end (E132, E232, E332, E432, E532, E632, E732, E832, E932, E1032, E1132) or the distal end (E134, E234, E334, E434, E534, E634, E734, E834, E934, E1034, E1134) such that the at least one relief slot (E160a, E160b, E260a, E260b, E260c, E360a, E360b, E460a, E460b, E460c, E560, E660a, E660b, E660c, E660d, E760, E860, E960a, E960b, E1060, E1160) opens directly into the at least one recess (E146).

Example 2

The staple cartridge (70) of Example 1, wherein the at least one retention tab (E130, E230a, E230b, E330, E430, E530, E630, E730, E830, E930, E1030, E1130) has an upper ramp surface (E150, E250a, E250b, E350, E450, E550, E650, E750, E850, E950, E1050, E1150), a lower ramp surface (E154, E254a, E254b, E354, E454, E554, E654, E754, E854, E954, E1054, E1154), and a middle engagement surface (E152, E252a, E252b, E352, E452, E552, E652, E752, E852, E952, E1052, E1152) extending between the upper ramp surface (E150, E250a, E250b, E350, E450, E550, E650, E750, E850, E950, E1050, E1150) and the lower ramp surface (E154, E254a, E254b, E354, E454, E554, E654, E754, E854, E954, E1054, E1154).

Example 3

The staple cartridge (70) of Example 2, wherein the middle engagement surface (E152, E252a, E252b, E352, E452, E552, E652, E752, E852, E952, E1052, E1152) is substantially flat.

Example 4

The staple cartridge (70) of any of Examples 2 through 3, wherein the upper ramp surface (E150, E250a, E250b, E350, E450, E550, E650, E750, E850, E950, E1050, E1150) is oriented obliquely at a first angle ($\alpha 1$) relative to the at least one sidewall (E112, E212, E312, E412, E512, E612, E712, E812, E912, E1012, E1112).

Example 5

The staple cartridge (70) of Example 4, wherein the lower ramp surface (E154, E254a, E254b, E354, E454, E554, E654, E754, E854, E954, E1054, E1154) is oriented obliquely at a second angle ($\alpha 2$) relative to the at least one sidewall (E112, E212, E312, E412, E512, E612, E712, E812, E912, E1012, E1112), wherein the second angle ($\alpha 2$) is different from the first angle ($\alpha 1$).

Example 6

The staple cartridge (70) of any of Examples 1 through 5, wherein the at least one recess (E146) opens through the at least one sidewall (E112, E212, E312, E412, E512, E612, E712, E812, E912, E1012, E1112) at both the proximal end (E132, E232, E332, E432, E532, E632, E732, E832, E932, E1032, E1132) and the distal end (E134, E234, E334, E434, E534, E634, E734, E834, E934, E1034, E1134).

Example 7

The staple cartridge (70) of Example 6, wherein the at least one relief slot (E160a, E160b, E260a, E260b, E260c, E360a, E360b, E460a, E460b, E460c, E560, E660a, E660b, E660c, E660d, E760, E860, E960a, E960b, E1060, E1160) is adjacent to both the proximal end (E132, E232, E332, E432, E532, E632, E732, E832, E932, E1032, E1132) and the distal end (E134, E234, E334, E434, E534, E634, E734, E834, E934, E1034, E1134) such that the at least one relief slot (E160a, E160b, E260a, E260b, E260c, E360a, E360b, E460a, E460b, E460c, E560, E660a, E660b, E660c, E660d, E760, E860, E960a, E960b, E1060, E1160) opens directly into the at least one recess (E146) at both the proximal end (E132, E232, E332, E432, E532, E632, E732, E832, E932, E1032, E1132) and the distal end (E134, E234, E334, E434, E534, E634, E734, E834, E934, E1034, E1134).

Example 8

The staple cartridge (70) of any of Examples 1 through 7, wherein the pan (E110, E210, E310, E410, E510, E610, E710, E810, E910, E1010, E1110) further includes a bottom wall (E114, E214, E314, E414, E514, E614, E714, E814, E914, E1014, E1114), wherein the at least one relief slot (E160a, E160b, E260a, E260b, E260c, E360a, E360b, E460a, E460b, E460c, E560, E660a, E660b, E660c, E660d, E760, E860, E960a, E960b, E1060, E1160) further extends through the bottom wall (E114, E214, E314, E414, E514, E614, E714, E814, E914, E1014, E1114).

Example 9

The staple cartridge (70) of any of Examples 1 through 8, wherein the at least one retention tab (E130, E230a, E230b, E330, E430, E530, E630, E730, E830, E930, E1030, E1130) includes a pair of retention tabs (E230a, E230b) spaced apart from each other by the at least one relief slot (E260c).

Example 10

The staple cartridge (70) of any of Examples 1 through 9, wherein the at least one relief slot (E160a, E160b, E260a, E260b, E260c, E360a, E360b, E460a, E460b, E460c, E560, E660a, E660b, E660c, E660d, E760, E860, E960a, E960b, E1060, E1160) is at least one of substantially elongate, substantially T-shaped, substantially L-shaped, substantially C-shaped, or substantially U-shaped.

Example 11

The staple cartridge (70) of any of Examples 1 through 10, wherein each sidewall (E112, E212, E312, E412, E512, E612, E712, E812, E912, E1012, E1112) of the laterally-opposed pair of sidewalls (E112, E212, E312, E412, E512, E612, E712, E812, E912, E1012, E1112) has a laterally inner side surface (E118, E1118), wherein the cartridge body (72, E1210, E1310) has at least one laterally outer side surface (E1324) configured to frictionally engage the laterally inner side surface (E118, E1118) of the respective sidewall (E112, E212, E312, E412, E512, E612, E712, E812, E912, E1012, E1112).

Example 12

The staple cartridge (70) of Example 11, wherein the cartridge body (72, E1210, E1310) has at least one recessed laterally outer surface (E1326) that is recessed laterally inwardly relative to the at least one laterally outer side surface (E1324).

Example 13

The staple cartridge (70) of Example 12, wherein the at least one recessed laterally outer surface (E1326) is at a substantially same position in a longitudinal direction as the at least one retention tab (E130, E230a, E230b, E330, E430, E530, E630, E730, E830, E930, E1030, E1130).

Example 14

The staple cartridge (70) of any of Examples 1 through 13, further comprising a staple actuator (82, E1410, E1510) translatable distally through the staple cartridge (70) along the longitudinal axis from a proximal unfired position to a distal fired position, wherein the staple actuator (82, E1410, E1510) is at a substantially same position in a longitudinal direction as the at least one retention tab (E130, E230a, E230b, E330, E430, E530, E630, E730, E830, E930, E1030, E1130) when the staple actuator (82, E1410, E1510) is in the distal fired position.

Example 15

The staple cartridge (70) of Example 14, wherein the staple actuator (82, E1410, E1510) comprises a metal material.

Example 16

A staple cartridge (70) for a surgical instrument (10), the staple cartridge (70) comprising: (a) a cartridge body (72, E1210, E1310) extending along a longitudinal axis and having an upper deck (74, E1212, E1312), wherein the upper deck (74, E1212, E1312) defines a stapling surface, wherein a plurality of pockets (80, E1216) extend through the upper deck (74, E1212, E1312) for receiving respective staples (86), wherein the cartridge body (72, E1210, E1310) has: (i) at least one laterally outer side surface (E1324), and (ii) at least one recessed laterally outer surface (E1326) that is recessed laterally inwardly relative to the at least one laterally outer side surface (E1324); and (b) a pan (E110, E210, E310, E410, E510, E610, E710, E810, E910, E1010, E1110) coupled to the cartridge body (72, E1210, E1310), wherein the pan (E110, E210, E310, E410, E510, E610, E710, E810, E910, E1010, E1110) includes: (i) a laterally-opposed pair of sidewalls (E112, E212, E312, E412, E512, E612, E712, E812, E912, E1012, E1112) spaced apart from each other to define a trough (E116), wherein the trough (E116) is sized and configured to receive the cartridge body (72, E1210, E1310), wherein each sidewall (E112, E212, E312, E412, E512, E612, E712, E812, E912, E1012, E1112) of the laterally-opposed pair of sidewalls (E112, E212, E312, E412, E512, E612, E712, E812, E912, E1012, E1112) has a laterally inner side surface (E118, E1118) configured to frictionally engage the at least one laterally outer side surface (E1324), and (ii) at least one retention tab (E130, E230a, E230b, E330, E430, E530, E630, E730, E830, E930, E1030, E1130) extending laterally outwardly from at least one sidewall (E112, E212, E312, E412, E512, E612, E712, E812, E912, E1012, E1112) of the laterally-opposed pair of sidewalls (E112, E212, E312, E412, E512, E612, E712, E812, E912, E1012, E1112), wherein the at least one retention tab (E130, E230a, E230b, E330, E430, E530, E630, E730, E830, E930, E1030, E1130) is at a substantially same position in a longitudinal direction as the at least one recessed laterally outer surface (E1326).

Example 17

The staple cartridge (70) of Example 16, wherein the cartridge body (72, E1210, E1310) has an underside (E1313), wherein the at least one recessed laterally outer surface (E1326) extends upwardly from the underside (E1313).

Example 18

The staple cartridge (70) of any of Examples 16 through 17, wherein the at least one retention tab (E130, E230a, E230b, E330, E430, E530, E630, E730, E830, E930, E1030, E1130) has a length (L), wherein the at least one recessed laterally outer surface (E1326) has a length (LA) substantially equal to or greater than the length (L) of the at least one retention tab (E130, E230a, E230b, E330, E430, E530, E630, E730, E830, E930, E1030, E1130).

Example 19

The staple cartridge (70) of any of Examples 16 through 18, wherein the at least one retention tab (E130, E230a, E230b, E330, E430, E530, E630, E730, E830, E930, E1030, E1130) has a height (H1), wherein the at least one recessed laterally outer surface (E1326) has a height (H2) substantially equal to or greater than the height (H1) of the at least one retention tab (E130, E230a, E230b, E330, E430, E530, E630, E730, E830, E930, E1030, E1130).

Example 20

The staple cartridge (70) of any of Examples 16 through 19, wherein the at least one recessed laterally outer surface (E1326) has a length (LA) of about 0.185 in.

Example 21

The staple cartridge (70) of any of Examples 16 through 20, wherein the at least one recessed laterally outer surface (E1326) has a height (H2) of about 0.094 in.

Example 22

The staple cartridge (70) of any of Examples 16 through 21, wherein the cartridge body (72, E1210, E1310) has a sidewall (E1320) presenting the at least one laterally outer side surface (E1324), the at least one recessed laterally outer surface (E1326), and a laterally inner side surface (E1322), wherein the sidewall (E1320) has a first thickness (X1) defined between the laterally inner side surface (E1322) and the at least one laterally outer side surface (E1324), and a second thickness (X2) defined between the laterally inner side surface (E1322) and the at least one recessed laterally outer surface (E1326) that is substantially less than the first thickness (X1).

Example 23

The staple cartridge (70) of any of Examples 16 through 22, wherein the at least one recessed laterally outer surface (E1326) is recessed laterally inwardly relative to the at least one laterally outer side surface (E1324) by a depth (D1) of about 0.003 in.

Example 24

The staple cartridge (70) of any of Examples 16 through 23, further comprising a staple actuator (82, E1410, E1510) translatable distally through the staple cartridge (70) along the longitudinal axis from a proximal unfired position to a distal fired position, wherein the staple actuator (82, E1410, E1510) is at the substantially same position in the longitudinal direction as the at least one retention tab (E130, E230a, E230b, E330, E430, E530, E630, E730, E830, E930, E1030, E1130) and the at least one recessed laterally outer surface (E1326) when the staple actuator (82, E1410, E1510) is in the distal fired position.

Example 25

The staple cartridge (70) of Example 24, wherein the staple actuator (82, E1410, E1510) comprises a metal material.

Example 26

A staple cartridge (70) for a surgical instrument (10), the staple cartridge (70) comprising: (a) a cartridge body (72, E1210, E1310) extending along a longitudinal axis and having an upper deck (74, E1212, E1312), wherein the upper deck (74, E1212, E1312) defines a stapling surface, wherein a plurality of pockets (80, E1216) extend through the upper deck (74, E1212, E1312) for receiving respective staples (86) wherein the cartridge body (72, E1210, E1310) has: (i) at least one longitudinally-extending interior wall (E1224), and (ii) a longitudinal row of driver pocket supports (E1230a, E1230b) spaced apart from the at least one interior wall (E1224) to define a longitudinally-extending sled rail track (E1222), wherein the plurality of driver pocket supports (E1230a, E1230b) includes: (A) at least one proximal driver pocket support (E1230a) having a first thickness (Y1), and (B) at least one distal driver pocket support (E1230b) having a second thickness (Y2), wherein the second thickness (Y2) is less than the first thickness (Y1) such that the sled rail track (E1222) has a first width (W1) between the at least one interior wall (E1224) and the at least one proximal driver pocket support (E1230a), and a second width (W2) between the at least one interior wall (E1224) and the at least one distal driver pocket support (E1230b), the second width (W2) being greater than the first width (W1); and (b) a staple actuator (82, E1410, E1510) translatable distally through the staple cartridge (70) along the longitudinal axis from a proximal unfired position to a distal fired position, wherein the staple actuator (82, E1410, E1510) includes at least one outer sled rail (E1414, E1514) slidably received within the sled rail track (E1222).

Example 27

The staple cartridge (70) of Example 26, wherein the at least one outer sled rail (E1414, E1514) is laterally spaced farther apart from the at least one distal driver pocket support (E1230b) than the at least one proximal driver pocket support (E1230a).

Example 28

The staple cartridge (70) of any of Examples 26 through 27, wherein the first thickness (Y1) is about 0.007 in.

Example 29

The staple cartridge (70) of any of Examples 26 through 28, wherein the second thickness (Y2) is about 0.005 in.

Example 30

The staple cartridge (70) of any of Examples 26 through 29, wherein the second thickness (Y2) is less than the first thickness (Y1) by about 0.002 in.

Example 31

The staple cartridge (70) of any of Examples 26 through 30, wherein the second width (W2) is greater than the first width (W1) by about 0.002 in.

Example 32

The staple cartridge (70) of any of Examples 26 through 31, wherein the at least one outer sled rail (E1414, E1514) is spaced apart from the at least one distal driver pocket support (E1230b) by a gap (G1) of at least about 0.003 in when the staple actuator (82, E1410, E1510) is in the distal fired position.

Example 33

The staple cartridge (70) of any of Examples 26 through 32, wherein the at least one outer sled rail (E1414, E1514) has at least one recessed laterally outer surface (E1426) that is configured to confront the at least one distal driver pocket support (E1230b) when the staple actuator (82, E1410, E1510) is in the distal fired position.

Example 34

The staple cartridge (70) of any of Examples 26 through 33, wherein the at least one outer sled rail (E1414, E1514) has at least one tapered laterally outer surface (E1524) that is configured to confront the at least one distal driver pocket support (E1230b) when the staple actuator (82, E1410, E1510) is in the distal fired position, the at least one tapered laterally outer surface (E1524) being tapered laterally inwardly and downwardly.

Example 35

The staple cartridge (70) of any of Examples 26 through 34, wherein the staple actuator (82, E1410, E1510) comprises a metal material.

The following clauses also relate to various non-exhaustive ways in which the teachings herein may be combined or applied.

1. A staple cartridge for a surgical instrument, the staple cartridge comprising:
   (a) a cartridge body extending along a longitudinal axis and having an upper deck, wherein the upper deck defines a stapling surface, wherein a plurality of pockets extend through the upper deck for receiving respective staples; and
   (b) a pan coupled to the cartridge body, wherein the pan includes:
      (i) a laterally-opposed pair of sidewalls spaced apart from each other to define a trough, wherein the trough is sized and configured to receive the cartridge body,
      (ii) at least one retention tab extending laterally outwardly from at least one sidewall of the laterally-opposed pair of sidewalls, wherein the at least one retention tab extends longitudinally between a proximal end and a distal end, wherein the at least one retention tab defines at least one recess extending laterally outwardly from the trough, wherein the at least one recess opens through the at least one sidewall at at least one of the proximal end or the distal end, and
      (iii) at least one relief slot extending through the at least one sidewall, wherein the at least one relief slot is adjacent to the at least one of the proximal end or the distal end such that the at least one relief slot opens directly into the at least one recess.
2. The staple cartridge of Clause 1, wherein the at least one retention tab has an upper ramp surface, a lower ramp surface, and a middle engagement surface extending between the upper ramp surface and the lower ramp surface.
3. The staple cartridge of Clause 2, wherein the middle engagement surface is substantially flat.
4. The staple cartridge of Clause 2, wherein the upper ramp surface is oriented obliquely at a first angle relative to the at least one sidewall.
5. The staple cartridge of Clause 4, wherein the lower ramp surface is oriented obliquely at a second angle relative to the at least one sidewall, wherein the second angle is different from the first angle.
6. The staple cartridge of Clause 1, wherein the at least one recess opens through the at least one sidewall at both the proximal end and the distal end.
7. The staple cartridge of Clause 6, wherein the at least one relief slot is adjacent to both the proximal end and the distal end such that the at least one relief slot opens directly into the at least one recess at both the proximal end and the distal end.
8. The staple cartridge of Clause 1, wherein the pan further includes a bottom wall, wherein the at least one relief slot further extends through the bottom wall.
9. The staple cartridge of Clause 1, wherein the at least one retention tab includes a pair of retention tabs spaced apart from each other by the at least one relief slot.
10. The staple cartridge of Clause 1, wherein the at least one relief slot is at least one of substantially elongate, substantially T-shaped, substantially L-shaped, substantially C-shaped, or substantially U-shaped.
11. The staple cartridge of Clause 1, wherein each sidewall of the laterally-opposed pair of sidewalls has a laterally inner side surface, wherein the cartridge body has at least one laterally outer side surface configured to frictionally engage the laterally inner side surface of the respective sidewall.
12. The staple cartridge of Clause 11, wherein the cartridge body has at least one recessed laterally outer surface that is recessed laterally inwardly relative to the at least one laterally outer side surface.
13. The staple cartridge of Clause 12, wherein the at least one recessed laterally outer surface is at a substantially same position in a longitudinal direction as the at least one retention tab.
14. The staple cartridge of Clause 1, further comprising a staple actuator translatable distally through the staple cartridge along the longitudinal axis from a proximal unfired position to a distal fired position, wherein the staple actuator is at a substantially same position in a longitudinal direction as the at least one retention tab when the staple actuator is in the distal fired position.
15. The staple cartridge of Clause 14, wherein the staple actuator comprises a metal material.
16. A staple cartridge for a surgical instrument, the staple cartridge comprising:
   (a) a cartridge body extending along a longitudinal axis and having an upper deck, wherein the upper deck defines a stapling surface, wherein a plurality of pockets extend through the upper deck for receiving respective staples, wherein the cartridge body has:
      (i) at least one laterally outer side surface, and
      (ii) at least one recessed laterally outer surface that is recessed laterally inwardly relative to the at least one laterally outer side surface; and
   (b) a pan coupled to the cartridge body, wherein the pan includes:
      (i) a laterally-opposed pair of sidewalls spaced apart from each other to define a trough, wherein the trough is sized and configured to receive the cartridge body, wherein each sidewall of the laterally-opposed pair of sidewalls has a laterally inner side surface configured to frictionally engage the at least one laterally outer side surface, and (ii) at least one retention tab extending laterally outwardly from at least one sidewall of the laterally-opposed pair of sidewalls, wherein the at least one retention tab is at a substantially same position in a longitudinal direction as the at least one recessed laterally outer surface.

17. The staple cartridge of Clause 16, wherein the cartridge body has an underside, wherein the at least one recessed laterally outer surface extends upwardly from the underside.

18. The staple cartridge of Clause 16, wherein the at least one retention tab has a length, wherein the at least one recessed laterally outer surface has a length substantially equal to or greater than the length of the at least one retention tab.

19. A staple cartridge for a surgical instrument, the staple cartridge comprising:
   (a) a cartridge body extending along a longitudinal axis and having an upper deck, wherein the upper deck defines a stapling surface, wherein a plurality of pockets extend through the upper deck for receiving respective staples wherein the cartridge body has:
      (i) at least one longitudinally-extending interior wall, and
      (ii) a longitudinal row of driver pocket supports spaced apart from the at least one interior wall to define a longitudinally-extending sled rail track, wherein the plurality of driver pocket supports includes:
         (A) at least one proximal driver pocket support having a first thickness, and
         (B) at least one distal driver pocket support having a second thickness, wherein the second thickness is less than the first thickness such that the sled rail track has a first width between the at least one interior wall and the at least one proximal driver pocket support, and a second width between the at least one interior wall and the at least one distal driver pocket support, the second width being greater than the first width; and
   (b) a staple actuator translatable distally through the staple cartridge along the longitudinal axis from a proximal unfired position to a distal fired position, wherein the staple actuator includes at least one outer sled rail slidably received within the sled rail track.

20. The staple cartridge of Clause 19, wherein the at least one outer sled rail is laterally spaced farther apart from the at least one distal driver pocket support than the at least one proximal driver pocket support.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 18/588,147, entitled "Surgical Stapler Cartridge Having Intermediate Raised Tissue Engagement Protrusions," filed on Feb. 27, 2024, published as U.S. Pat. Pub. No. 2024/0382197 on Nov. 21, 2024; U.S. patent application Ser. No. 18/588,175, entitled "Surgical Stapler Cartridge Having Tissue Engagement Protrusions with Enlarged Engagement Surface," filed on Feb. 27, 2024, published as U.S. Pat. Pub. No. 2024/0382195 on Nov. 21, 2024; U.S. patent application Ser. No. 18/588,206, entitled "Surgical Stapler Cartridge Having Raised Surface to Promote Buttress Adhesion," filed on Feb. 27, 2024, published as U.S. Pat. Pub. No. 2024/0382202 on Nov. 21, 2024; U.S. patent application Ser. No. 18/588,269, entitled "Surgical Stapler Anvil Having Staple Forming Pockets with Laterally Varying Orientations," filed on Feb. 27, 2024, published as U.S. Pat. Pub. No. 2024/0341761 on Oct. 17, 2024; U.S. patent application Ser. No. 18/588,684, entitled "Method of Surgical Stapling," filed on Feb. 27, 2024, published as U.S. Pat. Pub. No. 2024/0350137 on Oct. 24, 2024; and/or U.S. patent application Ser. No. 18/588,094, entitled "Incompatible Staple Cartridge Use Prevention Features for Surgical Stapler," filed on Feb. 27, 2024, published as U.S. Pat. Pub. No. 2024/0382201 on Nov. 21, 2024. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A staple cartridge for a surgical instrument, the staple cartridge comprising:
   (a) a cartridge body extending along a longitudinal axis and having an upper deck, wherein the upper deck defines a stapling surface, wherein a plurality of pockets extend through the upper deck for receiving respective staples; and
   (b) a pan coupled to the cartridge body, wherein the pan includes:
      (i) a laterally-opposed pair of sidewalls spaced apart from each other to define a trough, wherein the trough is sized and configured to receive the cartridge body,
      (ii) at least one retention tab extending laterally outwardly from at least one sidewall of the laterally-opposed pair of sidewalls, wherein the at least one retention tab extends longitudinally between a proximal end and a distal end, wherein the at least one retention tab defines at least one recess extending laterally outwardly from the trough, wherein the at least one recess opens through the at least one sidewall at at least one of the proximal end or the distal end, and
      (iii) at least one relief slot extending through the at least one sidewall, wherein the at least one relief slot is adjacent to the at least one of the proximal end or the distal end such that the at least one relief slot opens directly into the at least one recess.

2. The staple cartridge of claim 1, wherein the at least one retention tab has an upper ramp surface, a lower ramp surface, and a middle engagement surface extending between the upper ramp surface and the lower ramp surface.

3. The staple cartridge of claim 2, wherein the middle engagement surface is substantially flat.

4. The staple cartridge of claim 2, wherein the upper ramp surface is oriented obliquely at a first angle relative to the at least one sidewall.

5. The staple cartridge of claim 4, wherein the lower ramp surface is oriented obliquely at a second angle relative to the at least one sidewall, wherein the second angle is different from the first angle.

6. The staple cartridge of claim 1, wherein the at least one recess opens through the at least one sidewall at both the proximal end and the distal end.

7. The staple cartridge of claim 6, wherein the at least one relief slot is adjacent to both the proximal end and the distal end such that the at least one relief slot opens directly into the at least one recess at both the proximal end and the distal end.

8. The staple cartridge of claim 1, wherein the pan further includes a bottom wall, wherein the at least one relief slot further extends through the bottom wall.

9. The staple cartridge of claim 1, wherein the at least one retention tab includes a pair of retention tabs spaced apart from each other by the at least one relief slot.

10. The staple cartridge of claim 1, wherein the at least one relief slot is at least one of substantially elongate, substantially T-shaped, substantially L-shaped, substantially C-shaped, or substantially U-shaped.

11. The staple cartridge of claim 1, wherein each sidewall of the laterally-opposed pair of sidewalls has a laterally inner side surface, wherein the cartridge body has at least one laterally outer side surface configured to frictionally engage the laterally inner side surface of the respective sidewall.

12. The staple cartridge of claim 11, wherein the cartridge body has at least one recessed laterally outer surface that is recessed laterally inwardly relative to the at least one laterally outer side surface.

13. The staple cartridge of claim 12, wherein the at least one recessed laterally outer surface is at a substantially same position in a longitudinal direction as the at least one retention tab.

14. The staple cartridge of claim 1, further comprising a staple actuator translatable distally through the staple cartridge along the longitudinal axis from a proximal unfired position to a distal fired position, wherein the staple actuator is at a substantially same position in a longitudinal direction as the at least one retention tab when the staple actuator is in the distal fired position.

15. The staple cartridge of claim 14, wherein the staple actuator comprises a metal material.

16. A staple cartridge for a surgical instrument, the staple cartridge comprising:
   (a) a cartridge body extending along a longitudinal axis and having an upper deck, wherein the upper deck defines a stapling surface, wherein a plurality of pockets extend through the upper deck for receiving respective staples, wherein the cartridge body has:
      (i) at least one laterally outer side surface, and
      (ii) at least one recessed laterally outer surface that is recessed laterally inwardly relative to the at least one laterally outer side surface; and
   (b) a pan coupled to the cartridge body, wherein the pan includes:
      (i) a laterally-opposed pair of sidewalls spaced apart from each other to define a trough, wherein the trough is sized and configured to receive the cartridge body, wherein each sidewall of the laterally-opposed pair of sidewalls has a laterally inner side surface configured to frictionally engage the at least one laterally outer side surface, and
      (ii) at least one retention tab extending laterally outwardly from at least one sidewall of the laterally-opposed pair of sidewalls, wherein the at least one retention tab is at a substantially same position in a longitudinal direction as the at least one recessed laterally outer surface.

17. The staple cartridge of claim 16, wherein the cartridge body has an underside, wherein the at least one recessed laterally outer surface extends upwardly from the underside.

18. The staple cartridge of claim 16, wherein the at least one retention tab has a length, wherein the at least one recessed laterally outer surface has a length substantially equal to or greater than the length of the at least one retention tab.

19. A staple cartridge for a surgical instrument, the staple cartridge comprising:
(a) a cartridge body extending along a longitudinal axis and having an upper deck, wherein the upper deck defines a stapling surface, wherein a plurality of pockets extend through the upper deck for receiving respective staples wherein the cartridge body has:
  (i) at least one longitudinally-extending interior wall, and
  (ii) a longitudinal row of driver pocket supports spaced apart from the at least one interior wall to define a longitudinally-extending sled rail track, wherein the plurality of driver pocket supports includes:
    (A) at least one proximal driver pocket support having a first thickness, and
    (B) at least one distal driver pocket support having a second thickness,
  wherein the second thickness is less than the first thickness such that the sled rail track has a first width between the at least one interior wall and the at least one proximal driver pocket support, and a second width between the at least one interior wall and the at least one distal driver pocket support, the second width being greater than the first width; and
(b) a staple actuator translatable distally through the staple cartridge along the longitudinal axis from a proximal unfired position to a distal fired position, wherein the staple actuator includes at least one outer sled rail slidably received within the sled rail track.

20. The staple cartridge of claim 19, wherein the at least one outer sled rail is laterally spaced farther apart from the at least one distal driver pocket support than the at least one proximal driver pocket support.

* * * * *